US009051358B2

(12) United States Patent
Huang et al.

(10) Patent No.: US 9,051,358 B2
(45) Date of Patent: Jun. 9, 2015

(54) NONNATURAL COLLAGEN-LIKE PROTEIN AND USE THEREOF

(75) Inventors: Yanshan Huang, Hangzhou (CN); Linfu Zhou, Hangzhou (CN); Zhi Chen, Hangzhou (CN)

(73) Assignee: ZHEJIANG UNIVERSITY, Hangzhou, Zhejiang (CN)

( * ) Notice: Subject to any disclaimer, the term of this patent is extended or adjusted under 35 U.S.C. 154(b) by 18 days.

(21) Appl. No.: 13/510,937

(22) PCT Filed: Nov. 19, 2009

(86) PCT No.: PCT/CN2009/075039
§ 371 (c)(1), (2), (4) Date: May 19, 2012

(87) PCT Pub. No.: WO2011/060583
PCT Pub. Date: May 26, 2011

(65) Prior Publication Data
US 2013/0203959 A1 Aug. 8, 2013

(51) Int. Cl.
*C07K 19/00* (2006.01)
*C07K 14/00* (2006.01)
*C12N 15/09* (2006.01)
*C12N 15/63* (2006.01)
*A61K 47/42* (2006.01)
*C07K 14/78* (2006.01)
*A61K 38/01* (2006.01)

(52) U.S. Cl.
CPC ............... *C07K 14/001* (2013.01); *A61K 47/42* (2013.01); *C07K 14/78* (2013.01); *A61K 38/014* (2013.01)

(58) Field of Classification Search
None
See application file for complete search history.

(56) References Cited

U.S. PATENT DOCUMENTS 5,801,045 A * 9/1998 Weber et al. ............... 435/252.3
7,288,214 B2 * 10/2007 Bergmans et al. ............ 252/194
8,263,084 B2 * 9/2012 Song et al. ............... 424/195.11
8,349,589 B2 * 1/2013 De Boer et al. .............. 435/69.1
2007/0065440 A1 * 3/2007 Tomlinson et al. ........ 424/145.1
2009/0093407 A1 * 4/2009 Hall et al. ...................... 514/12

FOREIGN PATENT DOCUMENTS

EP CN101302255 A * 7/2002
WO PCT/CN2009/075039 8/2010

OTHER PUBLICATIONS

Lynn et al ("Antigenicity and Immunogenicity of Collagen" (Jul. 16, 2004) J Biomed Mater Res Part B: Appl Biomater 71B: 343-354).*
Leikin et al ("Temperature-favoured assembly of collagen is driven by hydrophilic not hydrophobic interactions" (1995) Nature Structural Biology 2:205-210).*
Kyte et al ("A simple method for displaying the hydropathic character of a protein" (May 5, 1982) J Mol Biol 157(1):105-32).*
Ramshaw et al ("Gly-X-Y tripeptide frequencies in collagen: a context for host-guest triple-helical peptides" (1998) J Struct Biol 122(1-2):86-91).*
Lynn et al (J Biomed Mater Res Part B: Appl Biomater (Jul. 16, 2004) 71 B: 343-354).*
Kolaskar et al (FESB Lett (Dec. 10, 1990) 276(1-2):172-174).*
Langberg et al (J Physiol (Nov. 15, 1999) 521 Pt 1:299-306).*
Langberg et al ("Type I collagen synthesis and degradation in peritendinous tissue after exercise determined by microdialysis in humans" (Nov. 15, 1999) J Physiol 521 Pt 1:299-306).*
Ramshaw et al ("Gly-X-Y tripeptide frequencies in collagen: a context for host-guest triple-helical peptides" (1998) 122(1-2):86-91).*
Lynn et al ("Antigenicity and Immunogenicity of Collagen" (Jul. 16, 2004) J Biomed Mater Res Part B: Appl Biomater 71 B: 343-354).*
Kolaskar et al ("A semi-empirical method for prediction of antigenic determinants onprotein antigens" (Dec. 10, 1990) FESB Lett 276(1-2):172-174).*

* cited by examiner

*Primary Examiner* — Karlheinz R Skowronek
*Assistant Examiner* — Mindy Newman
(74) *Attorney, Agent, or Firm* — Tianhua Gu; Global IP Services

(57) ABSTRACT

This present invention relates to compositions comprising biological active proteins fused with extended recombinant gelatin-like protein (GLK), nucleic acids encoding the compositions and vectors containing the same, approaches involved in the preparation of the compositions and their pharmaceutical application in the treatment or prevention of diseases.

21 Claims, 16 Drawing Sheets

SEQUENCE LISTING

<160> NUMBER OF SEQ ID NOS: 31

<210> SEQ ID NO 1
<211> LENGTH: 383
<212> TYPE: DNA
<213> ORGANISM: Artificial sequence
<220> FEATURE:
<223> OTHER INFORMATION: Complementary DNA sequence that encodes GLK1161 monomer

<400> SEQUENCE: 1
ctcgagaaaa gagaggctga agctggtcca cccggtgaac aaggtaaacc aggaaaccag 60
ggtgagccag gtaacccagg ttcccctggt cagccaggta accctggtca accaggttct 120
ccaggtaatc caggtcaacc aggaaacgaa ggtccacaag gttctcaggg taaccctgga 180
caacctggtg agccaggttc caacggtcaa cctggtcaac ctggtcagaa cggaaagaat 240
ggtcaacctg gatccccagg ttcacaaggc tctccaggta accaaggatc tcctggtaac 300
caaggacagc ccggtaacaa gggtgaacaa ggtaaaccag gaaaccaggg tccagccggt 360
ggctctggtg gataatagaa ttc 383

<210> SEQ ID NO 2
<211> LENGTH: 116
<212> TYPE: PRT
<213> ORGANISM: Artificial sequence
<220> FEATURE:
<223> OTHER INFORMATION: rGLK116 monomer

<400> SEQUENCE: 2

Gly Pro Pro Gly Glu Gln Gly Lys Pro Gly Asn Gln Gly Glu Pro Gly
1 5 10 15

Asn Pro Gly Ser Pro Gly Gln Pro Gly Asn Pro Gly Gln Pro Gly Ser
20 25 30

Pro Gly Asn Pro Gly Gln Pro Gly Asn Glu Gly Pro Gln Gly Ser Gln
35 40 45

Gly Asn Pro Gly Gln Pro Gly Glu Pro Gly Ser Asn Gly Gln Pro Gly
50 55 60

Gln Pro Gly Gln Asn Gly Lys Asn Gly Gln Pro Gly Ser Pro Gly Ser
65 70 75 80

Gln Gly Ser Pro Gly Asn Gln Gly Ser Pro Gly Asn Gln Gly Gln Pro
85 90 95

Gly Asn Lys Gly Glu Gln Gly Lys Pro Gly Asn Gln Gly Pro Ala Gly
100 105 110

Gly Ser Gly Gly
115

<210> SEQ ID NO 3
<211> LENGTH: 1355
<212> TYPE: DNA
<213> ORGANISM: Artificial sequence
<220> FEATURE:
<223> OTHER INFORMATION: Complementary DNA sequence(CDS:1-1344) that encodes GLK1164

<400> SEQUENCE: 3
ctcgagaaaa gagaggctga agctggtcca cccggtgaac aaggtaaacc aggaaaccag 60
ggtgagccag gtaacccagg ttcccctggt cagccaggta accctggtca accaggttct 120
ccaggtaatc caggtcaacc aggaaacgaa ggtccacaag gttctcaggg taaccctgga 180
caacctggtg agccaggttc caacggtcaa cctggtcaac ctggtcagaa cggaaagaat 240

-continued

```
ggtcaacctg gatccccagg ttcacaaggc tctccaggta accaaggatc tcctggtaac    300

caaggacagc ccggtaacaa gggtgaacaa ggtaaaccag gaaaccaggg tccagccggt    360

gaacaaggta aaccaggaaa ccagggtgag ccaggtaacc caggttcccc tggtcagcca    420

ggtaaccctg gtcaaccagg ttctccaggt aatccaggtc aaccaggaaa cgaaggtcca    480

caaggttctc agggtaaccc tggacaacct ggtgagccag gttccaacgg tcaacctggt    540

caacctggtc agaacggaaa gaatggtcaa cctggatccc caggttcaca aggctctcca    600

ggtaaccaag gatctcctgg taaccaagga cagcccggta acaagggtga acaaggtaaa    660

ccaggaaacc agggtccagc cggtgaacaa ggtaaaccag gaaaccaggg tgagccaggt    720

aacccaggtt cccctggtca gccaggtaac cctggtcaac caggttctcc aggtaatcca    780

ggtcaaccag gaaacgaagg tccacaaggt tctcagggta accctggaca acctggtgag    840

ccaggttcca acggtcaacc tggtcaacct ggtcagaacg gaaagaatgg tcaacctgga    900

tccccaggtt cacaaggctc tccaggtaac caaggatctc ctggtaacca aggacagccc    960

ggtaacaagg gtgaacaagg taaaccagga aaccagggtc cagccggtga acaaggtaaa   1020

ccaggaaacc agggtgagcc aggtaaccca ggttcccctg gtcagccagg taaccctggt   1080

caaccaggtt ctccaggtaa tccaggtcaa ccaggaaacg aaggtccaca aggttctcag   1140

ggtaaccctg gacaacctgg tgagccaggt tccaacggtc aacctggtca acctggtcag   1200

aacggaaaga atggtcaacc tggatcccca ggttcacaag gctctccagg taaccaagga   1260

tctcctggta accaaggaca gcccggtaac aagggtgaac aaggtaaacc aggaaaccag   1320

ggtccagccg gtggctctgg tggataatag aattc                              1355
```

<210> SEQ ID NO 4
<211> LENGTH: 552
<212> TYPE: DNA
<213> ORGANISM: Artificial Sequence
<220> FEATURE:
<223> OTHER INFORMATION: Complementary DNA sequence(CDS:22-543) that encodes hG-CSF

<400> SEQUENCE: 4

```
ccacccggtg gctctggtgg aacaccatta ggccctgcca gctccctgcc ccagagcttc     60

ctgctcaagt gcttagagca agtgaggaag atccagggcg atggcgcagc gctccaggag    120

aagctgtgtg ccacctacaa gctgtgccac cccgaggagc tggtgctgct cggacactct    180

ctgggcatcc cctgggctcc cctgagcagc tgccccagcc aggccctgca gctggcaggc    240

tgcttgagcc aactccatag cggccttttc ctctaccagg ggctcctgca ggccctggaa    300

gggatctccc ccgagttggg tcccaccttg gacacactgc agctggacgt cgccgacttt    360

gccacaacca tctggcagca gatggaagaa ctgggaatgg cccctgccct gcagcccacc    420

cagggtgcca tgccggcctt cgcctctgct ttccagcgcc gggcaggagg ggtcctggtt    480

gcctcccatc tgcagagctt cctggaggtg tcgtaccgcg ttctacgcca ccttgcccag    540

ccctgagaat tc                                                        552
```

<210> SEQ ID NO 5
<211> LENGTH: 1875
<212> TYPE: DNA
<213> ORGANISM: Artificial sequence
<220> FEATURE:
<223> OTHER INFORMATION: Complementary DNA sequence(CDS:1-1866) that encodes GLK1164/G-CSF -continued

<400> SEQUENCE: 5
ctcgagaaaa gagaggctga agctggtcca cccggtgaac aaggtaaacc aggaaaccag 60
ggtgagccag gtaacccagg ttcccctggt cagccaggta accctggtca accaggttct 120
ccaggtaatc caggtcaacc aggaaacgaa ggtccacaag gttctcaggg taaccctgga 180
caacctggtg agccaggttc caacggtcaa cctggtcaac ctggtcagaa cggaaagaat 240
ggtcaacctg gatccccagg ttcacaaggc tctccaggta accaaggatc tcctggtaac 300
caaggacagc ccggtaacaa gggtgaacaa ggtaaaccag gaaaccaggg tccagccggt 360
gaacaaggta aaccaggaaa ccagggtgag ccaggtaacc caggttcccc tggtcagcca 420
ggtaaccctg gtcaaccagg ttctccaggt aatccaggtc aaccaggaaa cgaaggtcca 480
caaggttctc agggtaaccc tggacaacct ggtgagccag gttccaacgg tcaacctggt 540
caacctggtc agaacggaaa gaatggtcaa cctggatccc caggttcaca aggctctcca 600
ggtaaccaag gatctcctgg taaccaagga cagcccggta acaagggtga acaaggtaaa 660
ccaggaaacc agggtccagc cggtgaacaa ggtaaaccag gaaaccaggg tgagccaggt 720
aacccaggtt cccctggtca gccaggtaac cctggtcaac caggttctcc aggtaatcca 780
ggtcaaccag gaaacgaagg tccacaaggt tctcagggta accctggaca acctggtgag 840
ccaggttcca acggtcaacc tggtcaacct ggtcagaacg gaaagaatgg tcaacctgga 900
tccccaggtt cacaaggctc tccaggtaac caaggatctc ctggtaacca aggacagccc 960
ggtaacaagg gtgaacaagg taaaccagga aaccagggtc cagccggtga acaaggtaaa 1020
ccaggaaacc agggtgagcc aggtaaccca ggttcccctg gtcagccagg taaccctggt 1080
caaccaggtt ctccaggtaa tccaggtcaa ccaggaaacg aaggtccaca aggttctcag 1140
ggtaaccctg gacaacctgg tgagccaggt tccaacggtc aacctggtca acctggtcag 1200
aacggaaaga atggtcaacc tggatcccca ggttcacaag gctctccagg taaccaagga 1260
tctcctggta accaaggaca gcccggtaac aagggtgaac aaggtaaacc aggaaaccag 1320
ggtccagccg gtggctctgg tggaacacca ttaggccctg ccagctccct gccccagagc 1380
ttcctgctca agtgcttaga gcaagtgagg aagatccagg gcgatggcgc agcgctccag 1440
gagaagctgt gtgccaccta caagctgtgc caccccgagg agctggtgct gctcggacac 1500
tctctgggca tcccctgggc tcccctgagc agctgcccca gccaggccct gcagctggca 1560
ggctgcttga gccaactcca tagcggcctt ttcctctacc aggggctcct gcaggccctg 1620
gaagggatct cccccgagtt gggtcccacc ttggacacac tgcagctgga cgtcgccgac 1680
tttgccacca ccatctggca gcagatggaa gaactgggaa tggcccctgc cctgcagccc 1740
acccagggtg ccatgccggc cttcgcctct gctttccagc gccgggcagg aggggtcctg 1800
gttgcctccc atctgcagag cttcctggag gtgtcgtacc gcgttctacg ccaccttgcc 1860
cagccctgag aattc 1875

<210> SEQ ID NO 6
<211> LENGTH: 614
<212> TYPE: PRT
<213> ORGANISM: Artificial sequence
<220> FEATURE:
<223> OTHER INFORMATION: rGLK116 tetramer/G-CSF

<400> SEQUENCE: 6

Gly Pro Pro Gly Glu Gln Gly Lys Pro Gly Asn Gln Gly Glu Pro Gly
1 5 10 15

-continued

```
Asn Pro Gly Ser Pro Gly Gln Pro Gly Asn Pro Gly Gln Pro Gly Ser
            20                  25                  30

Pro Gly Asn Pro Gly Gln Pro Gly Asn Glu Gly Pro Gln Gly Ser Gln
        35                  40                  45

Gly Asn Pro Gly Gln Pro Gly Glu Pro Gly Ser Asn Gly Gln Pro Gly
    50                  55                  60

Gln Pro Gly Gln Asn Gly Lys Asn Gly Gln Pro Gly Ser Pro Gly Ser
65                  70                  75                  80

Gln Gly Ser Pro Gly Asn Gln Gly Ser Pro Gly Asn Gln Gly Gln Pro
                85                  90                  95

Gly Asn Lys Gly Glu Gln Gly Lys Pro Gly Asn Gln Gly Pro Ala Gly
            100                 105                 110

Glu Gln Gly Lys Pro Gly Asn Gln Gly Glu Pro Gly Asn Pro Gly Ser
        115                 120                 125

Pro Gly Gln Pro Gly Asn Pro Gly Gln Pro Gly Ser Pro Gly Asn Pro
    130                 135                 140

Gly Gln Pro Gly Asn Glu Gly Pro Gln Gly Ser Gln Gly Asn Pro Gly
145                 150                 155                 160

Gln Pro Gly Glu Pro Gly Ser Asn Gly Gln Pro Gly Gln Pro Gly Gln
                165                 170                 175

Asn Gly Lys Asn Gly Gln Pro Gly Ser Pro Gly Ser Gln Gly Ser Pro
            180                 185                 190

Gly Asn Gln Gly Ser Pro Gly Asn Gln Gly Gln Pro Gly Asn Lys Gly
        195                 200                 205

Glu Gln Gly Lys Pro Gly Asn Gln Gly Pro Ala Gly Glu Gln Gly Lys
    210                 215                 220

Pro Gly Asn Gln Gly Glu Pro Gly Asn Pro Gly Ser Pro Gly Gln Pro
225                 230                 235                 240

Gly Asn Pro Gly Gln Pro Gly Ser Pro Gly Asn Pro Gly Gln Pro Gly
                245                 250                 255

Asn Glu Gly Pro Gln Gly Ser Gln Gly Asn Pro Gly Gln Pro Gly Glu
            260                 265                 270

Pro Gly Ser Asn Gly Gln Pro Gly Gln Pro Gly Gln Asn Gly Lys Asn
        275                 280                 285

Gly Gln Pro Gly Ser Pro Gly Ser Gln Gly Ser Pro Gly Asn Gln Gly
    290                 295                 300

Ser Pro Gly Asn Gln Gly Gln Pro Gly Asn Lys Gly Glu Gln Gly Lys
305                 310                 315                 320

Pro Gly Asn Gln Gly Pro Ala Gly Glu Gln Gly Lys Pro Gly Asn Gln
                325                 330                 335

Gly Glu Pro Gly Asn Pro Gly Ser Pro Gly Gln Pro Gly Asn Pro Gly
            340                 345                 350

Gln Pro Gly Ser Pro Gly Asn Pro Gly Gln Pro Gly Asn Glu Gly Pro
        355                 360                 365

Gln Gly Ser Gln Gly Asn Pro Gly Gln Pro Gly Glu Pro Gly Ser Asn
    370                 375                 380

Gly Gln Pro Gly Gln Pro Gly Gln Asn Gly Lys Asn Gly Gln Pro Gly
385                 390                 395                 400

Ser Pro Gly Ser Gln Gly Ser Pro Gly Asn Gln Gly Ser Pro Gly Asn
                405                 410                 415

Gln Gly Gln Pro Gly Asn Lys Gly Glu Gln Gly Lys Pro Gly Asn Gln
            420                 425                 430

Gly Pro Ala Gly Gly Ser Gly Gly Thr Pro Leu Gly Pro Ala Ser Ser
```

-continued

```
        435                 440                 445

Leu Pro Gln Ser Phe Leu Leu Lys Cys Leu Glu Gln Val Arg Lys Ile
    450                 455                 460

Gln Gly Asp Gly Ala Ala Leu Gln Glu Lys Leu Cys Ala Thr Tyr Lys
465                 470                 475                 480

Leu Cys His Pro Glu Glu Leu Val Leu Leu Gly His Ser Leu Gly Ile
                485                 490                 495

Pro Trp Ala Pro Leu Ser Ser Cys Pro Ser Gln Ala Leu Gln Leu Ala
            500                 505                 510

Gly Cys Leu Ser Gln Leu His Ser Gly Leu Phe Leu Tyr Gln Gly Leu
        515                 520                 525

Leu Gln Ala Leu Glu Gly Ile Ser Pro Glu Leu Gly Pro Thr Leu Asp
    530                 535                 540

Thr Leu Gln Leu Asp Val Ala Asp Phe Ala Thr Thr Ile Trp Gln Gln
545                 550                 555                 560

Met Glu Glu Leu Gly Met Ala Pro Ala Leu Gln Pro Thr Gln Gly Ala
                565                 570                 575

Met Pro Ala Phe Ala Ser Ala Phe Gln Arg Arg Ala Gly Gly Val Leu
            580                 585                 590

Val Ala Ser His Leu Gln Ser Phe Leu Glu Val Ser Tyr Arg Val Leu
        595                 600                 605

Arg His Leu Ala Gln Pro
    610


<210> SEQ ID NO 7
<211> LENGTH: 1295
<212> TYPE: DNA
<213> ORGANISM: Homo sapiens
<220> FEATURE:
<221> NAME/KEY: sig_peptide
<222> LOCATION: (1)..(24)
<223> OTHER INFORMATION: Complementary DNA sequence(CDS:1-1284) that
      encodes GLK420

<400> SEQUENCE: 7

ctcgagaaaa gagaggctga agctggtccc cctggagaag acggagataa gggagagatc      60

ggggagccgg ggcagaaagg aagcaagggg gacaaaggag aacagggtcc tcctgggcct     120

acaggtcctc aaggccccat cggacagcca ggcccctctg gagctgacgg cgagccgggg     180

cctcggggcc agcagggcct tttcgggcag aaaggtgatg aaggtcccag aggctttcct     240

ggacccccctg ggccagtggg gctgcagggt ttgccaggac ctccaggcga gaagggtgag     300

acaggagacg tgggccagat gggcccccg ggtcccccctg gcccccgagg accctccgga     360

gctccaggtg ctgatggccc acaaggtccc ccaggtggaa taggaaaccc tggtgcagtg     420

ggagagaagg gcgagcctgg cgaagcaggt gagcctggcc ttccgggaga aggcggcccc     480

ccgggaccca aaggagaaag gggagagaag ggcgagtcag gcccttcagg tgctgccgga     540

ccccctggac ccaaaggccc tcccggagat gatggtccca aaggcagccc tggcccagtg     600

ggttttcctg gagatcctgg cccccccgga gagcctggcc ccgcgggtca agatggtccc     660

cctggtgaca aaggagatga tggtgaaccc gggcagacgg gatcccccgg ccctactggt     720

gaaccaggtc catcggggcc tccaggaaaa aggggtcccc caggccccgc aggccccgaa     780

ggcagacagg gagagaaagg ggccaaggga gaagccggct tggaaggccc tcctgggaag     840

actggcccca tcggccccca gggggcccct gggaagcccg gaccggatgg ccttcgaggg     900

atccctggcc ctgtgggaga acaaggtctc ccaggatccc caggcccgga cggtcccccc     960
```

-continued

```
ggccccatgg gtcccccagg acttcccggc ctcaaaggag attctggtcc caaaggtgaa   1020

aagggtcatc caggcctgat cgggctcatc ggtcctccgg gtgaacaggg tgagaagggc   1080

gaccgtggtc tccctggccc ccagggctcc tccggtccta agggagaaca gggtatcact   1140

ggtccttctg gcccgattgg gcctcctggg ccccctggcc tgccgggtcc gcctggtcca   1200

aaaggtgcta agggctcctc gggtccaact ggcccgaagg gtgaggcagg ccacccagga   1260

cccccaggcc ccccgggccc cccgtaatag aattc                              1295


<210> SEQ ID NO 8
<211> LENGTH: 420
<212> TYPE: PRT
<213> ORGANISM: Homo sapiens
<220> FEATURE:
<221> NAME/KEY: mat_peptide
<222> LOCATION: (1)..(420)
<223> OTHER INFORMATION: GLK420

<400> SEQUENCE: 8

Gly Pro Pro Gly Glu Asp Gly Asp Lys Gly Glu Ile Gly Glu Pro Gly
1               5                   10                  15

Gln Lys Gly Ser Lys Gly Asp Lys Gly Glu Gln Gly Pro Pro Gly Pro
            20                  25                  30

Thr Gly Pro Gln Gly Pro Ile Gly Gln Pro Gly Pro Ser Gly Ala Asp
        35                  40                  45

Gly Glu Pro Gly Pro Arg Gly Gln Gln Gly Leu Phe Gly Gln Lys Gly
    50                  55                  60

Asp Glu Gly Pro Arg Gly Phe Pro Gly Pro Pro Gly Pro Val Gly Leu
65                  70                  75                  80

Gln Gly Leu Pro Gly Pro Pro Gly Glu Lys Gly Glu Thr Gly Asp Val
                85                  90                  95

Gly Gln Met Gly Pro Pro Gly Pro Pro Gly Pro Arg Gly Pro Ser Gly
            100                 105                 110

Ala Pro Gly Ala Asp Gly Pro Gln Gly Pro Pro Gly Gly Ile Gly Asn
        115                 120                 125

Pro Gly Ala Val Gly Glu Lys Gly Glu Pro Gly Glu Ala Gly Glu Pro
    130                 135                 140

Gly Leu Pro Gly Glu Gly Gly Pro Pro Gly Pro Lys Gly Glu Arg Gly
145                 150                 155                 160

Glu Lys Gly Glu Ser Gly Pro Ser Gly Ala Ala Gly Pro Pro Gly Pro
                165                 170                 175

Lys Gly Pro Pro Gly Asp Asp Gly Pro Lys Gly Ser Pro Gly Pro Val
            180                 185                 190

Gly Phe Pro Gly Asp Pro Gly Pro Pro Gly Glu Pro Gly Pro Ala Gly
        195                 200                 205

Gln Asp Gly Pro Pro Gly Asp Lys Gly Asp Asp Gly Glu Pro Gly Gln
    210                 215                 220

Thr Gly Ser Pro Gly Pro Thr Gly Glu Pro Gly Pro Ser Gly Pro Pro
225                 230                 235                 240

Gly Lys Arg Gly Pro Pro Gly Pro Ala Gly Pro Glu Gly Arg Gln Gly
                245                 250                 255

Glu Lys Gly Ala Lys Gly Glu Ala Gly Leu Glu Gly Pro Pro Gly Lys
            260                 265                 270

Thr Gly Pro Ile Gly Pro Gln Gly Ala Pro Gly Lys Pro Gly Pro Asp
        275                 280                 285
```

-continued

Gly Leu Arg Gly Ile Pro Gly Pro Val Gly Glu Gln Gly Leu Pro Gly
    290                 295                 300

Ser Pro Gly Pro Asp Gly Pro Pro Gly Pro Met Gly Pro Pro Gly Leu
305                 310                 315                 320

Pro Gly Leu Lys Gly Asp Ser Gly Pro Lys Gly Glu Lys Gly His Pro
                325                 330                 335

Gly Leu Ile Gly Leu Ile Gly Pro Pro Gly Glu Gln Gly Glu Lys Gly
            340                 345                 350

Asp Arg Gly Leu Pro Gly Pro Gln Gly Ser Ser Gly Pro Lys Gly Glu
        355                 360                 365

Gln Gly Ile Thr Gly Pro Ser Gly Pro Ile Gly Pro Pro Gly Pro Pro
    370                 375                 380

Gly Leu Pro Gly Pro Pro Gly Pro Lys Gly Ala Lys Gly Ser Ser Gly
385                 390                 395                 400

Pro Thr Gly Pro Lys Gly Glu Ala Gly His Pro Gly Pro Pro Gly Pro
                405                 410                 415

Pro Gly Pro Pro
            420

<210> SEQ ID NO 9
<211> LENGTH: 1815
<212> TYPE: DNA
<213> ORGANISM: Artificial sequence
<220> FEATURE:
<223> OTHER INFORMATION: Complementary DNA sequence(CDS:1-1806) that
      encodes GLK420/G-CSF

<400> SEQUENCE: 9
ctcgagaaaa gagaggctga agctggtccc cctggagaag acggagataa gggagagatc     60
ggggagccgg ggcagaaagg aagcaagggg gacaaaggag aacagggtcc tcctgggcct    120
acaggtcctc aaggccccat cggacagcca ggcccctctg gagctgacgg cgagccgggg    180
cctcggggcc agcagggcct tttcgggcag aaaggtgatg aaggtcccag aggctttcct    240 ggacccccctg ggccagtggg gctgcagggt ttgccaggac ctccaggcga gaagggtgag    300
acaggagacg tgggccagat gggcccccccg ggtcccccctg gcccccgagg accctccgga    360
gctccaggtg ctgatggccc acaaggtccc ccaggtggaa taggaaaccc tggtgcagtg    420
ggagagaagg gcgagcctgg cgaagcaggt gagcctggcc ttccgggaga aggcggcccc    480
ccgggaccca aaggagaaag gggagagaag ggcgagtcag gcccttcagg tgctgccgga    540
ccccctggac ccaaaggccc tcccggagat gatggtccca aaggcagccc tggcccagtg    600
ggttttcctg gagatcctgg cccccccgga gagcctggcc ccgcgggtca agatggtccc    660
cctggtgaca aaggagatga tggtgaaccc gggcagacgg gatcccccgg ccctactggt    720
gaaccaggtc catcggggcc tccaggaaaa aggggtcccc caggccccgc aggccccgaa    780
ggcagacagg gagagaaagg ggccaaggga gaagccggct tggaaggccc tcctgggaag    840
actggcccca tcggccccca gggggcccct gggaagcccg gaccggatgg ccttcgaggg    900
atccctggcc ctgtgggaga acaaggtctc ccaggatccc caggcccgga cggtcccccc    960
ggccccatgg gtcccccagg acttcccggc ctcaaaggag attctggtcc caaaggtgaa   1020
aagggtcatc caggcctgat cggggctcatc ggtcctccgg gtgaacaggg tgagaagggc   1080
gaccgtggtc tccctggccc ccaggggctcc tccggtccta agggagaaca gggtatcact   1140
ggtccttctg gcccgattgg gcctcctggg ccccctggcc tgccgggtcc gcctggtcca   1200
aaaggtgcta agggctcctc gggtccaact ggcccgaagg gtgaggcagg ccacccagga   1260

```
cccccaggcc ccccgggccc cccgacacca ttaggccctg ccagctccct gccccagagc   1320

ttcctgctca agtgcttaga gcaagtgagg aagatccagg gcgatggcgc agcgctccag   1380

gagaagctgt gtgccaccta caagctgtgc caccccgagg agctggtgct gctcggacac   1440

tctctgggca tcccctgggc tcccctgagc agctgcccca gccaggccct gcagctggca   1500

ggctgcttga gccaactcca tagcggcctt ttcctctacc aggggctcct gcaggccctg   1560

gaagggatct cccccgagtt gggtcccacc ttggacacac tgcagctgga cgtcgccgac   1620

tttgccacca ccatctggca gcagatggaa gaactgggaa tggcccctgc cctgcagccc   1680

acccagggtg ccatgccggc cttcgcctct gctttccagc gccgggcagg aggggtcctg   1740

gttgcctccc atctgcagag cttcctggag gtgtcgtacc gcgttctacg ccaccttgcc   1800

cagccctgag aattc                                                    1815
```

```
<210> SEQ ID NO 10
<211> LENGTH: 594
<212> TYPE: PRT
<213> ORGANISM: Artificial sequence
<220> FEATURE:
<223> OTHER INFORMATION: GLK420/G-CSF, fusion protein

<400> SEQUENCE: 10

Gly Pro Pro Gly Glu Asp Gly Asp Lys Gly Glu Ile Gly Glu Pro Gly
1               5                   10                  15

Gln Lys Gly Ser Lys Gly Asp Lys Gly Glu Gln Gly Pro Pro Gly Pro
            20                  25                  30

Thr Gly Pro Gln Gly Pro Ile Gly Gln Pro Gly Pro Ser Gly Ala Asp
        35                  40                  45

Gly Glu Pro Gly Pro Arg Gly Gln Gln Gly Leu Phe Gly Gln Lys Gly
    50                  55                  60

Asp Glu Gly Pro Arg Gly Phe Pro Gly Pro Pro Gly Pro Val Gly Leu
65                  70                  75                  80

Gln Gly Leu Pro Gly Pro Pro Gly Glu Lys Gly Glu Thr Gly Asp Val
                85                  90                  95

Gly Gln Met Gly Pro Pro Gly Pro Pro Gly Pro Arg Gly Pro Ser Gly
            100                 105                 110

Ala Pro Gly Ala Asp Gly Pro Gln Gly Pro Pro Gly Gly Ile Gly Asn
        115                 120                 125

Pro Gly Ala Val Gly Glu Lys Gly Glu Pro Gly Glu Ala Gly Glu Pro
    130                 135                 140

Gly Leu Pro Gly Glu Gly Gly Pro Pro Gly Pro Lys Gly Glu Arg Gly
145                 150                 155                 160

Glu Lys Gly Glu Ser Gly Pro Ser Gly Ala Ala Gly Pro Pro Gly Pro
                165                 170                 175

Lys Gly Pro Pro Gly Asp Asp Gly Pro Lys Gly Ser Pro Gly Pro Val
            180                 185                 190

Gly Phe Pro Gly Asp Pro Gly Pro Pro Gly Glu Pro Gly Pro Ala Gly
        195                 200                 205

Gln Asp Gly Pro Pro Gly Asp Lys Gly Asp Asp Gly Glu Pro Gly Gln
    210                 215                 220

Thr Gly Ser Pro Gly Pro Thr Gly Glu Pro Gly Pro Ser Gly Pro Pro
225                 230                 235                 240

Gly Lys Arg Gly Pro Pro Gly Pro Ala Gly Pro Glu Gly Arg Gln Gly
                245                 250                 255
```

-continued

```
Glu Lys Gly Ala Lys Gly Glu Ala Gly Leu Glu Gly Pro Pro Gly Lys
            260                 265                 270

Thr Gly Pro Ile Gly Pro Gln Gly Ala Pro Gly Lys Pro Gly Pro Asp
        275                 280                 285

Gly Leu Arg Gly Ile Pro Gly Pro Val Gly Glu Gln Gly Leu Pro Gly
    290                 295                 300

Ser Pro Gly Pro Asp Gly Pro Pro Gly Pro Met Gly Pro Pro Gly Leu
305                 310                 315                 320

Pro Gly Leu Lys Gly Asp Ser Gly Pro Lys Gly Glu Lys Gly His Pro
                325                 330                 335

Gly Leu Ile Gly Leu Ile Gly Pro Pro Gly Glu Gln Gly Glu Lys Gly
            340                 345                 350

Asp Arg Gly Leu Pro Gly Pro Gln Gly Ser Ser Gly Pro Lys Gly Glu
        355                 360                 365

Gln Gly Ile Thr Gly Pro Ser Gly Pro Ile Gly Pro Pro Gly Pro Pro
    370                 375                 380

Gly Leu Pro Gly Pro Pro Gly Pro Lys Gly Ala Lys Gly Ser Ser Gly
385                 390                 395                 400

Pro Thr Gly Pro Lys Gly Glu Ala Gly His Pro Gly Pro Pro Gly Pro
                405                 410                 415

Pro Gly Pro Pro Thr Pro Leu Gly Pro Ala Ser Ser Leu Pro Gln Ser
            420                 425                 430

Phe Leu Leu Lys Cys Leu Glu Gln Val Arg Lys Ile Gln Gly Asp Gly
        435                 440                 445

Ala Ala Leu Gln Glu Lys Leu Cys Ala Thr Tyr Lys Leu Cys His Pro
    450                 455                 460

Glu Glu Leu Val Leu Leu Gly His Ser Leu Gly Ile Pro Trp Ala Pro
465                 470                 475                 480

Leu Ser Ser Cys Pro Ser Gln Ala Leu Gln Leu Ala Gly Cys Leu Ser
                485                 490                 495

Gln Leu His Ser Gly Leu Phe Leu Tyr Gln Gly Leu Leu Gln Ala Leu
            500                 505                 510

Glu Gly Ile Ser Pro Glu Leu Gly Pro Thr Leu Asp Thr Leu Gln Leu
        515                 520                 525

Asp Val Ala Asp Phe Ala Thr Thr Ile Trp Gln Gln Met Glu Glu Leu
    530                 535                 540

Gly Met Ala Pro Ala Leu Gln Pro Thr Gln Gly Ala Met Pro Ala Phe
545                 550                 555                 560

Ala Ser Ala Phe Gln Arg Arg Ala Gly Gly Val Leu Val Ala Ser His
                565                 570                 575

Leu Gln Ser Phe Leu Glu Val Ser Tyr Arg Val Leu Arg His Leu Ala
            580                 585                 590

Gln Pro


<210> SEQ ID NO 11
<211> LENGTH: 525
<212> TYPE: DNA
<213> ORGANISM: Homo sapiens
<220> FEATURE:
<221> NAME/KEY: misc_feature
<222> LOCATION: (1)..(21)
<223> OTHER INFORMATION: Complementary DNA sequence(CDS:22-516) that
      encodes Interferon 2b

<400> SEQUENCE: 11

ccacccggtg gctctggtgg atgtgatctg cctcaaaccc acagcctggg tagcaggagg      60
```

-continued accttgatgc tcctggcaca gatgaggaga atctctcttt tctcctgctt gaaggacaga 120
catgactttg gatttcccca ggaggagttt ggcaaccagt tccaaaaggc tgaaaccatc 180
cctgtcctcc atgagatgat ccagcagatc ttcaatctct tcagcacaaa ggactcatct 240
gctgcttggg atgagaccct cctagacaaa ttctacactg aactctacca gcagctgaat 300
gacctggaag cctgtgtgat acagggggtg ggggtgacag agactcccct gatgaaggag 360
gactccattc tggctgtgag gaaatacttc caaagaatca ctctctatct gaaagagaag 420
aaatacagcc cttgtgcctg ggaggttgtc agagcagaaa tcatgagatc tttttctttg 480
tcaacaaact tgcaagaaag tttaagaagt aaggaataag aattc 525

<210> SEQ ID NO 12
<211> LENGTH: 1848
<212> TYPE: DNA
<213> ORGANISM: Artificial sequence
<220> FEATURE:
<223> OTHER INFORMATION: Complementary DNA sequence(CDS:1-1839) that
encodes GLK1164/IFN

<400> SEQUENCE: 12
ctcgagaaaa gagaggctga agctggtcca cccggtgaac aaggtaaacc aggaaaccag 60
ggtgagccag gtaacccagg ttcccctggt cagccaggta accctggtca accaggttct 120
ccaggtaatc caggtcaacc aggaaacgaa ggtccacaag gttctcaggg taaccctgga 180
caacctggtg agccaggttc caacggtcaa cctggtcaac ctggtcagaa cggaaagaat 240
ggtcaacctg gatccccagg ttcacaaggc tctccaggta accaaggatc tcctggtaac 300
caaggacagc ccggtaacaa gggtgaacaa ggtaaaccag gaaaccaggg tccagccggt 360
gaacaaggta aaccaggaaa ccagggtgag ccaggtaacc caggttcccc tggtcagcca 420
ggtaaccctg gtcaaccagg ttctccaggt aatccaggtc aaccaggaaa cgaaggtcca 480
caaggttctc agggtaaccc tggacaacct ggtgagccag gttccaacgg tcaacctggt 540
caacctggtc agaacggaaa gaatggtcaa cctggatccc caggttcaca aggctctcca 600
ggtaaccaag gatctcctgg taaccaagga cagcccggta acaagggtga acaaggtaaa 660
ccaggaaacc agggtccagc cggtgaacaa ggtaaaccag gaaaccaggg tgagccaggt 720
aacccaggtt cccctggtca gccaggtaac cctggtcaac caggttctcc aggtaatcca 780
ggtcaaccag gaaacgaagg tccacaaggt tctcagggta accctggaca acctggtgag 840
ccaggttcca acggtcaacc tggtcaacct ggtcagaacg gaaagaatgg tcaacctgga 900
tccccaggtt cacaaggctc tccaggtaac caaggatctc ctggtaacca aggacagccc 960
ggtaacaagg gtgaacaagg taaaccagga aaccagggtc cagccggtga acaaggtaaa 1020
ccaggaaacc agggtgagcc aggtaaccca ggttcccctg gtcagccagg taaccctggt 1080
caaccaggtt ctccaggtaa tccaggtcaa ccaggaaacg aaggtccaca aggttctcag 1140
ggtaaccctg gacaacctgg tgagccaggt tccaacggtc aacctggtca acctggtcag 1200
aacggaaaga atggtcaacc tggatcccca ggttcacaag gctctccagg taaccaagga 1260
tctcctggta accaaggaca gcccggtaac aagggtgaac aaggtaaacc aggaaaccag 1320
ggtccagccg gtggctctgg tggatgtgat ctgcctcaaa cccacagcct gggtagcagg 1380
aggaccttga tgctcctggc acagatgagg agaatctctc ttttctcctg cttgaaggac 1440
agacatgact ttggatttcc ccaggaggag tttggcaacc agttccaaaa ggctgaaacc 1500
atccctgtcc tccatgagat gatccagcag atcttcaatc tcttcagcac aaaggactca 1560

```
tctgctgctt gggatgagac cctcctagac aaattctaca ctgaactcta ccagcagctg   1620

aatgacctgg aagcctgtgt gatacagggg gtgggggtga cagagactcc cctgatgaag   1680

gaggactcca ttctggctgt gaggaaatac ttccaaagaa tcactctcta tctgaaagag   1740

aagaaataca gcccttgtgc ctgggaggtt gtcagagcag aaatcatgag atctttttct   1800

ttgtcaacaa acttgcaaga aagtttaaga agtaaggaat aagaattc                1848


<210> SEQ ID NO 13
<211> LENGTH: 605
<212> TYPE: PRT
<213> ORGANISM: Artificial sequence
<220> FEATURE:
<223> OTHER INFORMATION: rGLK1164/IFNa, fusion protein

<400> SEQUENCE: 13

Gly Pro Pro Gly Glu Gln Gly Lys Pro Gly Asn Gln Gly Glu Pro Gly
1               5                   10                  15

Asn Pro Gly Ser Pro Gly Gln Pro Gly Asn Pro Gly Gln Pro Gly Ser
            20                  25                  30

Pro Gly Asn Pro Gly Gln Pro Gly Asn Glu Gly Pro Gln Gly Ser Gln
        35                  40                  45

Gly Asn Pro Gly Gln Pro Gly Glu Pro Gly Ser Asn Gly Gln Pro Gly
    50                  55                  60

Gln Pro Gly Gln Asn Gly Lys Asn Gly Gln Pro Gly Ser Pro Gly Ser
65                  70                  75                  80

Gln Gly Ser Pro Gly Asn Gln Gly Ser Pro Gly Asn Gln Gly Gln Pro
                85                  90                  95

Gly Asn Lys Gly Glu Gln Gly Lys Pro Gly Asn Gln Gly Pro Ala Gly
            100                 105                 110

Glu Gln Gly Lys Pro Gly Asn Gln Gly Glu Pro Gly Asn Pro Gly Ser
        115                 120                 125

Pro Gly Gln Pro Gly Asn Pro Gly Gln Pro Gly Ser Pro Gly Asn Pro
    130                 135                 140

Gly Gln Pro Gly Asn Glu Gly Pro Gln Gly Ser Gln Gly Asn Pro Gly
145                 150                 155                 160

Gln Pro Gly Glu Pro Gly Ser Asn Gly Gln Pro Gly Gln Pro Gly Gln
                165                 170                 175

Asn Gly Lys Asn Gly Gln Pro Gly Ser Pro Gly Ser Gln Gly Ser Pro
            180                 185                 190

Gly Asn Gln Gly Ser Pro Gly Asn Gln Gly Gln Pro Gly Asn Lys Gly
        195                 200                 205

Glu Gln Gly Lys Pro Gly Asn Gln Gly Pro Ala Gly Glu Gln Gly Lys
    210                 215                 220

Pro Gly Asn Gln Gly Glu Pro Gly Asn Pro Gly Ser Pro Gly Gln Pro
225                 230                 235                 240

Gly Asn Pro Gly Gln Pro Gly Ser Pro Gly Asn Pro Gly Gln Pro Gly
                245                 250                 255

Asn Glu Gly Pro Gln Gly Ser Gln Gly Asn Pro Gly Gln Pro Gly Glu
            260                 265                 270

Pro Gly Ser Asn Gly Gln Pro Gly Gln Pro Gly Gln Asn Gly Lys Asn
        275                 280                 285

Gly Gln Pro Gly Ser Pro Gly Ser Gln Gly Ser Pro Gly Asn Gln Gly
    290                 295                 300

Ser Pro Gly Asn Gln Gly Gln Pro Gly Asn Lys Gly Glu Gln Gly Lys
```

-continued

```
305                 310                 315                 320

Pro Gly Asn Gln Gly Pro Ala Gly Glu Gln Gly Lys Pro Gly Asn Gln
                325                 330                 335

Gly Glu Pro Gly Asn Pro Gly Ser Pro Gly Gln Pro Gly Asn Pro Gly
            340                 345                 350

Gln Pro Gly Ser Pro Gly Asn Pro Gly Gln Pro Gly Asn Glu Gly Pro
        355                 360                 365

Gln Gly Ser Gln Gly Asn Pro Gly Gln Pro Gly Glu Pro Gly Ser Asn
    370                 375                 380

Gly Gln Pro Gly Gln Pro Gly Gln Asn Gly Lys Asn Gly Gln Pro Gly
385                 390                 395                 400

Ser Pro Gly Ser Gln Gly Ser Pro Gly Asn Gln Gly Ser Pro Gly Asn
                405                 410                 415

Gln Gly Gln Pro Gly Asn Lys Gly Glu Gln Gly Lys Pro Gly Asn Gln
            420                 425                 430

Gly Pro Ala Gly Gly Ser Gly Gly Cys Asp Leu Pro Gln Thr His Ser
        435                 440                 445

Leu Gly Ser Arg Arg Thr Leu Met Leu Leu Ala Gln Met Arg Arg Ile
    450                 455                 460

Ser Leu Phe Ser Cys Leu Lys Asp Arg His Asp Phe Gly Phe Pro Gln
465                 470                 475                 480

Glu Glu Phe Gly Asn Gln Phe Gln Lys Ala Glu Thr Ile Pro Val Leu
                485                 490                 495

His Glu Met Ile Gln Gln Ile Phe Asn Leu Phe Ser Thr Lys Asp Ser
            500                 505                 510

Ser Ala Ala Trp Asp Glu Thr Leu Leu Asp Lys Phe Tyr Thr Glu Leu
        515                 520                 525

Tyr Gln Gln Leu Asn Asp Leu Glu Ala Cys Val Ile Gln Gly Val Gly
    530                 535                 540

Val Thr Glu Thr Pro Leu Met Lys Glu Asp Ser Ile Leu Ala Val Arg
545                 550                 555                 560

Lys Tyr Phe Gln Arg Ile Thr Leu Tyr Leu Lys Glu Lys Lys Tyr Ser
                565                 570                 575

Pro Cys Ala Trp Glu Val Val Arg Ala Glu Ile Met Arg Ser Phe Ser
            580                 585                 590

Leu Ser Thr Asn Leu Gln Glu Ser Leu Arg Ser Lys Glu
        595                 600                 605


<210> SEQ ID NO 14
<211> LENGTH: 389
<212> TYPE: PRT
<213> ORGANISM: Artificial sequence
<220> FEATURE:
<223> OTHER INFORMATION: rGLK1162/IFNa, fusion protein

<400> SEQUENCE: 14

Gly Pro Pro Gly Glu Gln Gly Lys Pro Gly Asn Gln Gly Glu Pro Gly
1               5                   10                  15

Asn Pro Gly Ser Pro Gly Gln Pro Gly Asn Pro Gly Gln Pro Gly Ser
            20                  25                  30

Pro Gly Asn Pro Gly Gln Pro Gly Asn Glu Gly Pro Gln Gly Ser Gln
        35                  40                  45

Gly Asn Pro Gly Gln Pro Gly Glu Pro Gly Ser Asn Gly Gln Pro Gly
    50                  55                  60

Gln Pro Gly Gln Asn Gly Lys Asn Gly Gln Pro Gly Ser Pro Gly Ser
```

-continued

```
65                  70                  75                  80

Gln Gly Ser Pro Gly Asn Gln Gly Ser Pro Gly Asn Gln Gly Gln Pro
                85                  90                  95

Gly Asn Lys Gly Glu Gln Gly Lys Pro Gly Asn Gln Gly Pro Ala Gly
            100                 105                 110

Glu Gln Gly Lys Pro Gly Asn Gln Gly Glu Pro Gly Asn Pro Gly Ser
        115                 120                 125

Pro Gly Gln Pro Gly Asn Pro Gly Gln Pro Gly Ser Pro Gly Asn Pro
    130                 135                 140

Gly Gln Pro Gly Asn Glu Gly Pro Gln Gly Ser Gln Gly Asn Pro Gly
145                 150                 155                 160

Gln Pro Gly Glu Pro Gly Ser Asn Gly Gln Pro Gly Gln Pro Gly Gln
                165                 170                 175

Asn Gly Lys Asn Gly Gln Pro Gly Ser Pro Gly Ser Gln Gly Ser Pro
            180                 185                 190

Gly Asn Gln Gly Ser Pro Gly Asn Gln Gly Gln Pro Gly Asn Lys Gly
        195                 200                 205

Glu Gln Gly Lys Pro Gly Asn Gln Gly Pro Ala Gly Gly Ser Gly Gly
    210                 215                 220

Cys Asp Leu Pro Gln Thr His Ser Leu Gly Ser Arg Arg Thr Leu Met
225                 230                 235                 240

Leu Leu Ala Gln Met Arg Arg Ile Ser Leu Phe Ser Cys Leu Lys Asp
                245                 250                 255

Arg His Asp Phe Gly Phe Pro Gln Glu Glu Phe Gly Asn Gln Phe Gln
            260                 265                 270

Lys Ala Glu Thr Ile Pro Val Leu His Glu Met Ile Gln Gln Ile Phe
        275                 280                 285

Asn Leu Phe Ser Thr Lys Asp Ser Ser Ala Ala Trp Asp Glu Thr Leu
    290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Thr Glu Thr Pro Leu Met Lys
                325                 330                 335

Glu Asp Ser Ile Leu Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380

Leu Arg Ser Lys Glu
385


<210> SEQ ID NO 15
<211> LENGTH: 389
<212> TYPE: PRT
<213> ORGANISM: Artificial sequence
<220> FEATURE:
<223> OTHER INFORMATION: rGLK1162/IFNa, fusion protein

<400> SEQUENCE: 15

Gly Ser Ser Gly Glu Gln Gly Lys Ser Gly Asn Gln Gly Glu Ser Gly
1               5                   10                  15

Asn Ser Gly Ser Ser Gly Gln Ser Gly Asn Ser Gly Gln Ser Gly Ser
            20                  25                  30

Ser Gly Asn Ser Gly Gln Ser Gly Asn Glu Gly Ser Gln Gly Ser Gln
```

-continued

```
        35                  40                  45

Gly Asn Ser Gly Gln Ser Gly Glu Ser Gly Ser Asn Gly Gln Ser Gly
    50                  55                  60

Gln Ser Gly Gln Asn Gly Lys Asn Gly Gln Ser Gly Ser Ser Gly Ser
65                  70                  75                  80

Gln Gly Ser Ser Gly Asn Gln Gly Ser Ser Gly Asn Gln Gly Gln Ser
                85                  90                  95

Gly Asn Lys Gly Glu Gln Gly Lys Ser Gly Asn Gln Gly Ser Ala Gly
            100                 105                 110

Glu Gln Gly Lys Ser Gly Asn Gln Gly Glu Ser Gly Asn Ser Gly Ser
        115                 120                 125

Ser Gly Gln Ser Gly Asn Ser Gly Gln Ser Gly Ser Ser Gly Asn Ser
    130                 135                 140

Gly Gln Ser Gly Asn Glu Gly Ser Gln Gly Ser Gln Gly Asn Ser Gly
145                 150                 155                 160

Gln Ser Gly Glu Ser Gly Ser Asn Gly Gln Ser Gly Gln Ser Gly Gln
                165                 170                 175

Asn Gly Lys Asn Gly Gln Ser Gly Ser Ser Gly Ser Gln Gly Ser Ser
            180                 185                 190

Gly Asn Gln Gly Ser Ser Gly Asn Gln Gly Gln Ser Gly Asn Lys Gly
        195                 200                 205

Glu Gln Gly Lys Ser Gly Asn Gln Gly Ser Ala Gly Gly Ser Gly Gly
    210                 215                 220

Cys Asp Leu Pro Gln Thr His Ser Leu Gly Ser Arg Arg Thr Leu Met
225                 230                 235                 240

Leu Leu Ala Gln Met Arg Arg Ile Ser Leu Phe Ser Cys Leu Lys Asp
                245                 250                 255

Arg His Asp Phe Gly Phe Pro Gln Glu Glu Phe Gly Asn Gln Phe Gln
            260                 265                 270

Lys Ala Glu Thr Ile Pro Val Leu His Glu Met Ile Gln Gln Ile Phe
        275                 280                 285

Asn Leu Phe Ser Thr Lys Asp Ser Ser Ala Ala Trp Asp Glu Thr Leu
    290                 295                 300

Leu Asp Lys Phe Tyr Thr Glu Leu Tyr Gln Gln Leu Asn Asp Leu Glu
305                 310                 315                 320

Ala Cys Val Ile Gln Gly Val Gly Val Thr Glu Thr Pro Leu Met Lys
                325                 330                 335

Glu Asp Ser Ile Leu Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380

Leu Arg Ser Lys Glu
385


<210> SEQ ID NO 16
<211> LENGTH: 467
<212> TYPE: PRT
<213> ORGANISM: Artificial sequence
<220> FEATURE:
<223> OTHER INFORMATION: rGLK302S/IFNa, fusion protein

<400> SEQUENCE: 16

Gly Gly Ser Gly Gly Ser Gly Gly Ser Gly Gly Ser Gly Gly Ser Gly
```

-continued

```
1               5                   10                  15

Gly Ser Gly Gly Ser Gly Gly Ser Gly Gly Ser Gly Gly Ser Gly Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser Gly
            100                 105                 110

Gly Ser Gly Gly Ser Gly Gly Ser Gly Gly Ser Gly Gly Ser Gly Gly
        115                 120                 125

Ser Gly Gly Ser Gly Gly Ser Gly Gly Ser Gly Gly Ser Gly Gly Ser
    130                 135                 140

Gly Gly Ser Gly Gly Ser Gly Gly Ser Gly Gly Ser Gly Gly Ser Gly
145                 150                 155                 160

Gly Ser Gly Gly Ser Gly Gly Ser Gly Gly Ser Gly Gly Ser Gly Gly
                165                 170                 175

Ser Gly Gly Ser Gly Gly Ser Gly Gly Ser Gly Gly Ser Gly Gly Ser
            180                 185                 190

Gly Gly Ser Gly Gly Ser Gly Gly Ser Gly Gly Ser Gly Gly Ser Gly
        195                 200                 205

Gly Ser Gly Gly Ser Gly Gly Ser Gly Gly Ser Gly Gly Ser Gly Gly
    210                 215                 220

Ser Gly Gly Ser Gly Gly Ser Gly Gly Ser Gly Gly Ser Gly Gly Ser
225                 230                 235                 240

Gly Gly Ser Gly Gly Ser Gly Gly Ser Gly Gly Ser Gly Gly Ser Gly
                245                 250                 255

Gly Ser Gly Gly Ser Gly Gly Ser Gly Gly Ser Gly Gly Ser Gly Gly
            260                 265                 270

Ser Gly Gly Ser Gly Gly Ser Gly Gly Ser Gly Gly Ser Gly Gly Ser
        275                 280                 285

Gly Gly Ser Gly Gly Ser Gly Gly Ser Gly Gly Ser Gly Gly Cys Asp
    290                 295                 300

Leu Pro Gln Thr His Ser Leu Gly Ser Arg Arg Thr Leu Met Leu Leu
305                 310                 315                 320

Ala Gln Met Arg Arg Ile Ser Leu Phe Ser Cys Leu Lys Asp Arg His
                325                 330                 335

Asp Phe Gly Phe Pro Gln Glu Glu Phe Gly Asn Gln Phe Gln Lys Ala
            340                 345                 350

Glu Thr Ile Pro Val Leu His Glu Met Ile Gln Gln Ile Phe Asn Leu
        355                 360                 365

Phe Ser Thr Lys Asp Ser Ser Ala Ala Trp Asp Glu Thr Leu Leu Asp
    370                 375                 380

Lys Phe Tyr Thr Glu Leu Tyr Gln Gln Leu Asn Asp Leu Glu Ala Cys
385                 390                 395                 400

Val Ile Gln Gly Val Gly Val Thr Glu Thr Pro Leu Met Lys Glu Asp
                405                 410                 415

Ser Ile Leu Ala Val Arg Lys Tyr Phe Gln Arg Ile Thr Leu Tyr Leu
            420                 425                 430
```

Lys Glu Lys Lys Tyr Ser Pro Cys Ala Trp Glu Val Val Arg Ala Glu
435 440 445

Ile Met Arg Ser Phe Ser Leu Ser Thr Asn Leu Gln Glu Ser Leu Arg
450 455 460

Ser Lys Glu
465

<210> SEQ ID NO 17
<211> LENGTH: 389
<212> TYPE: PRT
<213> ORGANISM: Artificial sequence
<220> FEATURE:
<223> OTHER INFORMATION: rGLK1162N-/IFNa, fusion protein

<400> SEQUENCE: 17

Gly Pro Pro Gly Glu Gln Gly Lys Pro Gly Glu Gln Gly Glu Pro Gly
1 5 10 15

Glu Pro Gly Ser Pro Gly Gln Pro Gly Glu Pro Gly Gln Pro Gly Ser
20 25 30

Pro Gly Glu Pro Gly Gln Pro Gly Glu Glu Gly Pro Gln Gly Ser Gln
35 40 45

Gly Glu Pro Gly Gln Pro Gly Glu Pro Gly Ser Glu Gly Gln Pro Gly
50 55 60

Gln Pro Gly Gln Glu Gly Lys Glu Gly Gln Pro Gly Ser Pro Gly Ser
65 70 75 80

Gln Gly Ser Pro Gly Glu Gln Gly Ser Pro Gly Glu Gln Gly Gln Pro
85 90 95

Gly Glu Lys Gly Glu Gln Gly Lys Pro Gly Glu Gln Gly Pro Ala Gly
100 105 110

Glu Gln Gly Lys Pro Gly Glu Gln Gly Glu Pro Gly Glu Pro Gly Ser
115 120 125

Pro Gly Gln Pro Gly Glu Pro Gly Gln Pro Gly Ser Pro Gly Glu Pro
130 135 140

Gly Gln Pro Gly Glu Glu Gly Pro Gln Gly Ser Gln Gly Glu Pro Gly
145 150 155 160

Gln Pro Gly Glu Pro Gly Ser Glu Gly Gln Pro Gly Gln Pro Gly Gln
165 170 175

Glu Gly Lys Glu Gly Gln Pro Gly Ser Pro Gly Ser Gln Gly Ser Pro
180 185 190

Gly Glu Gln Gly Ser Pro Gly Glu Gln Gly Gln Pro Gly Glu Lys Gly
195 200 205

Glu Gln Gly Lys Pro Gly Glu Gln Gly Pro Ala Gly Gly Ser Gly Gly
210 215 220

Cys Asp Leu Pro Gln Thr His Ser Leu Gly Ser Arg Arg Thr Leu Met
225 230 235 240

Leu Leu Ala Gln Met Arg Arg Ile Ser Leu Phe Ser Cys Leu Lys Asp
245 250 255

Arg His Asp Phe Gly Phe Pro Gln Glu Glu Phe Gly Asn Gln Phe Gln
260 265 270

Lys Ala Glu Thr Ile Pro Val Leu His Glu Met Ile Gln Gln Ile Phe
275 280 285

Asn Leu Phe Ser Thr Lys Asp Ser Ser Ala Ala Trp Asp Glu Thr Leu
290 295 300

Leu Asp Lys Phe Tyr Thr Glu Leu Tyr Gln Gln Leu Asn Asp Leu Glu
305 310 315 320

```
Ala Cys Val Ile Gln Gly Val Gly Val Thr Glu Thr Pro Leu Met Lys
                325                 330                 335

Glu Asp Ser Ile Leu Ala Val Arg Lys Tyr Phe Gln Arg Ile Thr Leu
            340                 345                 350

Tyr Leu Lys Glu Lys Lys Tyr Ser Pro Cys Ala Trp Glu Val Val Arg
        355                 360                 365

Ala Glu Ile Met Arg Ser Phe Ser Leu Ser Thr Asn Leu Gln Glu Ser
    370                 375                 380

Leu Arg Ser Lys Glu
385


<210> SEQ ID NO 18
<211> LENGTH: 347
<212> TYPE: DNA
<213> ORGANISM: Artificial sequence
<220> FEATURE:
<223> OTHER INFORMATION: Complementary DNA sequence(CDS:1-336) that
      encodesGLK1041 monomer

<400> SEQUENCE: 18

ctcgagaaaa gagaggctga agctggtcca cccggtgagc caggtaaccc aggatctcct      60

ggtaaccaag gacagcccgg taacaagggt tctccaggta atccaggtca accaggaaac     120

gaaggtcaac ctggtcaacc tggtcagaac ggacaacctg gtgagccagg ttccaacggt     180

ccacaaggtt ctcagggtaa ccctggaaag aatggtcaac ctggatcccc aggttcacaa     240

ggctctccag gtaaccaagg ttcccctggt cagccaggta accctggtca accaggtgaa     300

caaggtaaac caggaaacca gggtccagcc ggtggctaat agaattc                  347


<210> SEQ ID NO 19
<211> LENGTH: 104
<212> TYPE: PRT
<213> ORGANISM: Artificial sequence
<220> FEATURE:
<223> OTHER INFORMATION: rGLK1041 monomer

<400> SEQUENCE: 19

Gly Pro Pro Gly Glu Pro Gly Asn Pro Gly Ser Pro Gly Asn Gln Gly
1               5                   10                  15

Gln Pro Gly Asn Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
        35                  40                  45

Gly Ser Asn Gly Pro Gln Gly Ser Gln Gly Asn Pro Gly Lys Asn Gly
    50                  55                  60

Gln Pro Gly Ser Pro Gly Ser Gln Gly Ser Pro Gly Asn Gln Gly Ser
65                  70                  75                  80

Pro Gly Gln Pro Gly Asn Pro Gly Gln Pro Gly Glu Gln Gly Lys Pro
                85                  90                  95

Gly Asn Gln Gly Pro Ala Gly Gly
            100


<210> SEQ ID NO 20
<211> LENGTH: 356
<212> TYPE: DNA
<213> ORGANISM: Homo sapiens
<220> FEATURE:
<221> NAME/KEY: misc_feature
<222> LOCATION: (1)..(24)
<223> OTHER INFORMATION: Complementary DNA sequence(CDS:1-345) that
```

encodes GLK1071 monomer

<400> SEQUENCE: 20

```
ctcgagaaaa gagaggctga agctggtcca cctggtgaag acggagataa gggagagatc     60

ggggagccgg ggcagaaagg aagcaagggg gacaaaggag aacagggtcc tcctgggcct    120

acaggtcctc aaggccccat cggacagcca ggcccctctg gagctgacgg cgagccgggg    180

cctcggggcc agcagggcct tttcgggcag aaaggtgatg aaggtcccag aggctttcct    240

ggacccccctg ggccagtggg gctgcagggt ttgccaggac ctccaggcga gaagggtgag    300

acaggagacg tgggccagat gggcccccccg ggtccacctg gtggataata gaattc        356
```

<210> SEQ ID NO 21
<211> LENGTH: 107
<212> TYPE: PRT
<213> ORGANISM: Homo sapiens
<220> FEATURE:
<221> NAME/KEY: mat_peptide
<222> LOCATION: (1)..(107)
<223> OTHER INFORMATION: GLK107 monomer

<400> SEQUENCE: 21

```
Gly Pro Pro Gly Glu Asp Gly Asp Lys Gly Glu Ile Gly Glu Pro Gly
1               5                   10                  15

Gln Lys Gly Ser Lys Gly Asp Lys Gly Glu Gln Gly Pro Pro Gly Pro
            20                  25                  30

Thr Gly Pro Gln Gly Pro Ile Gly Gln Pro Gly Pro Ser Gly Ala Asp
        35                  40                  45

Gly Glu Pro Gly Pro Arg Gly Gln Gln Gly Leu Phe Gly Gln Lys Gly
    50                  55                  60

Asp Glu Gly Pro Arg Gly Phe Pro Gly Pro Pro Gly Pro Val Gly Leu
65                  70                  75                  80

Gln Gly Leu Pro Gly Pro Pro Gly Glu Lys Gly Glu Thr Gly Asp Val
                85                  90                  95

Gly Gln Met Gly Pro Pro Gly Pro Pro Gly Gly
            100                 105
```

<210> SEQ ID NO 22
<211> LENGTH: 154
<212> TYPE: DNA
<213> ORGANISM: Heloderma suspectum
<220> FEATURE:
<221> NAME/KEY: sig_peptide
<222> LOCATION: (1)..(24)
<223> OTHER INFORMATION: Complementary DNA sequence(CDS:1-141) that
encodes Exendin-4

<400> SEQUENCE: 22

```
ctcgagaaaa gagaggctga agctcacggt gagggtactt tcacttctga cttgtctaag     60

caaatggagg aggaggctgt tagattgttc attgagtggt tgaagaacgg tggtccatct    120

tctggtgctc caccaccatc tggtccaccc ggtg                                154
```

<210> SEQ ID NO 23
<211> LENGTH: 1949
<212> TYPE: DNA
<213> ORGANISM: Artificial sequence
<220> FEATURE:
<223> OTHER INFORMATION: Complementary DNA sequence(CDS:1-1938) that
encodes Exendin-4/GLK1046

<400> SEQUENCE: 23

-continued

```
ctcgagaaaa gagaggctga agctcacggt gagggtactt tcacttctga cttgtctaag     60
caaatggagg aggaggctgt tagattgttc attgagtggt tgaagaacgg tggtccatct    120
tctggtgctc caccaccatc tggtccaccc ggtgagccag gtaacccagg atctcctggt    180
aaccaaggac agcccggtaa caagggttct ccaggtaatc caggtcaacc aggaaacgaa    240
ggtcaacctg gtcaacctgg tcagaacgga caacctggtg agccaggttc caacggtcca    300
caaggttctc agggtaaccc tggaaagaat ggtcaacctg gatccccagg ttcacaaggc    360
tctccaggta accaaggttc ccctggtcag ccaggtaacc ctggtcaacc aggtgaacaa    420
ggtaaaccag gaaaccaggg tccagccggt gagccaggta acccaggatc tcctggtaac    480
caaggacagc ccggtaacaa gggttctcca ggtaatccag gtcaaccagg aaacgaaggt    540
caacctggtc aacctggtca gaacggacaa cctggtgagc caggttccaa cggtccacaa    600
ggttctcagg gtaaccctgg aaagaatggt caacctggat ccccaggttc acaaggctct    660
ccaggtaacc aaggttcccc tggtcagcca ggtaaccctg gtcaaccagg tgaacaaggt    720
aaaccaggaa accagggtcc agccggtgag ccaggtaacc caggatctcc tggtaaccaa    780
ggacagcccg gtaacaaggg ttctccaggt aatccaggtc aaccaggaaa cgaaggtcaa    840
cctggtcaac ctggtcagaa cggacaacct ggtgagccag gttccaacgg tccacaaggt    900
tctcagggta accctggaaa gaatggtcaa cctggatccc caggttcaca aggctctcca    960
ggtaaccaag gttcccctgg tcagccaggt aaccctggtc aaccaggtga acaaggtaaa   1020
ccaggaaacc agggtccagc cggtgagcca ggtaacccag gatctcctgg taaccaagga   1080
cagcccggta acaagggttc tccaggtaat ccaggtcaac caggaaacga aggtcaacct   1140
ggtcaacctg gtcagaacgg acaacctggt gagccaggtt ccaacggtcc acaaggttct   1200
cagggtaacc ctggaaagaa tggtcaacct ggatccccag gttcacaagg ctctccaggt   1260
aaccaaggtt cccctggtca gccaggtaac cctggtcaac caggtgaaca aggtaaacca   1320
ggaaaccagg gtccagccgg tgagccaggt aacccaggat ctcctggtaa ccaaggacag   1380
cccggtaaca agggttctcc aggtaatcca ggtcaaccag gaaacgaagg tcaacctggt   1440
caacctggtc agaacggaca acctggtgag ccaggttcca acggtccaca aggttctcag   1500
ggtaaccctg gaaagaatgg tcaacctgga tccccaggtt cacaaggctc tccaggtaac   1560
caaggttccc ctggtcagcc aggtaaccct ggtcaaccag gtgaacaagg taaaccagga   1620
aaccagggtc cagccggtga gccaggtaac ccaggatctc ctggtaacca aggacagccc   1680
ggtaacaagg gttctccagg taatccaggt caaccaggaa acgaaggtca acctggtcaa   1740
cctggtcaga acggacaacc tggtgagcca ggttccaacg gtccacaagg ttctcagggt   1800
aaccctggaa agaatggtca acctggatcc ccaggttcac aaggctctcc aggtaaccaa   1860
ggttcccctg gtcagccagg taaccctggt caaccaggtg aacaaggtaa accaggaaac   1920
cagggtccag ccggtggcta atagaattc                                     1949
```

<210> SEQ ID NO 24
<211> LENGTH: 638
<212> TYPE: PRT
<213> ORGANISM: Artificial sequence
<220> FEATURE:
<223> OTHER INFORMATION: rExendin-4/GLK1046

<400> SEQUENCE: 24

```
His Gly Glu Gly Thr Phe Thr Ser Asp Leu Ser Lys Gln Met Glu Glu
1               5                   10                  15
```

-continued

```
Glu Ala Val Arg Leu Phe Ile Glu Trp Leu Lys Asn Gly Gly Pro Ser
            20                  25                  30

Ser Gly Ala Pro Pro Pro Ser Gly Pro Pro Gly Glu Pro Gly Asn Pro
        35                  40                  45

Gly Ser Pro Gly Asn Gln Gly Gln Pro Gly Asn Lys Gly Ser Pro Gly
    50                  55                  60

Asn Pro Gly Gln Pro Gly Asn Glu Gly Gln Pro Gly Gln Pro Gly Gln
65                  70                  75                  80

Asn Gly Gln Pro Gly Glu Pro Gly Ser Asn Gly Pro Gln Gly Ser Gln
                85                  90                  95

Gly Asn Pro Gly Lys Asn Gly Gln Pro Gly Ser Pro Gly Ser Gln Gly
            100                 105                 110

Ser Pro Gly Asn Gln Gly Ser Pro Gly Gln Pro Gly Asn Pro Gly Gln
        115                 120                 125

Pro Gly Glu Gln Gly Lys Pro Gly Asn Gln Gly Pro Ala Gly Glu Pro
    130                 135                 140

Gly Asn Pro Gly Ser Pro Gly Asn Gln Gly Gln Pro Gly Asn Lys Gly
145                 150                 155                 160

Ser Pro Gly Asn Pro Gly Gln Pro Gly Asn Glu Gly Gln Pro Gly Gln
                165                 170                 175

Pro Gly Gln Asn Gly Gln Pro Gly Glu Pro Gly Ser Asn Gly Pro Gln
            180                 185                 190

Gly Ser Gln Gly Asn Pro Gly Lys Asn Gly Gln Pro Gly Ser Pro Gly
        195                 200                 205

Ser Gln Gly Ser Pro Gly Asn Gln Gly Ser Pro Gly Gln Pro Gly Asn
    210                 215                 220

Pro Gly Gln Pro Gly Glu Gln Gly Lys Pro Gly Asn Gln Gly Pro Ala
225                 230                 235                 240

Gly Glu Pro Gly Asn Pro Gly Ser Pro Gly Asn Gln Gly Gln Pro Gly
                245                 250                 255

Asn Lys Gly Ser Pro Gly Asn Pro Gly Gln Pro Gly Asn Glu Gly Gln
            260                 265                 270

Pro Gly Gln Pro Gly Gln Asn Gly Gln Pro Gly Glu Pro Gly Ser Asn
        275                 280                 285

Gly Pro Gln Gly Ser Gln Gly Asn Pro Gly Lys Asn Gly Gln Pro Gly
    290                 295                 300

Ser Pro Gly Ser Gln Gly Ser Pro Gly Asn Gln Gly Ser Pro Gly Gln
305                 310                 315                 320

Pro Gly Asn Pro Gly Gln Pro Gly Glu Gln Gly Lys Pro Gly Asn Gln
                325                 330                 335

Gly Pro Ala Gly Glu Pro Gly Asn Pro Gly Ser Pro Gly Asn Gln Gly
            340                 345                 350

Gln Pro Gly Asn Lys Gly Ser Pro Gly Asn Pro Gly Gln Pro Gly Asn
        355                 360                 365

Glu Gly Gln Pro Gly Gln Pro Gly Gln Asn Gly Gln Pro Gly Glu Pro
    370                 375                 380

Gly Ser Asn Gly Pro Gln Gly Ser Gln Gly Asn Pro Gly Lys Asn Gly
385                 390                 395                 400

Gln Pro Gly Ser Pro Gly Ser Gln Gly Ser Pro Gly Asn Gln Gly Ser
                405                 410                 415

Pro Gly Gln Pro Gly Asn Pro Gly Gln Pro Gly Glu Gln Gly Lys Pro
            420                 425                 430

Gly Asn Gln Gly Pro Ala Gly Glu Pro Gly Asn Pro Gly Ser Pro Gly
```

-continued

```
        435                 440                 445

Asn Gln Gly Gln Pro Gly Asn Lys Gly Ser Pro Gly Asn Pro Gly Gln
    450                 455                 460

Pro Gly Asn Glu Gly Gln Pro Gly Gln Pro Gly Gln Asn Gly Gln Pro
465                 470                 475                 480

Gly Glu Pro Gly Ser Asn Gly Pro Gln Gly Ser Gln Gly Asn Pro Gly
                485                 490                 495

Lys Asn Gly Gln Pro Gly Ser Pro Gly Ser Gln Gly Ser Pro Gly Asn
            500                 505                 510

Gln Gly Ser Pro Gly Gln Pro Gly Asn Pro Gly Gln Pro Gly Glu Gln
        515                 520                 525

Gly Lys Pro Gly Asn Gln Gly Pro Ala Gly Glu Pro Gly Asn Pro Gly
    530                 535                 540

Ser Pro Gly Asn Gln Gly Gln Pro Gly Asn Lys Gly Ser Pro Gly Asn
545                 550                 555                 560

Pro Gly Gln Pro Gly Asn Glu Gly Gln Pro Gly Gln Pro Gly Gln Asn
                565                 570                 575

Gly Gln Pro Gly Glu Pro Gly Ser Asn Gly Pro Gln Gly Ser Gln Gly
            580                 585                 590

Asn Pro Gly Lys Asn Gly Gln Pro Gly Ser Pro Gly Ser Gln Gly Ser
        595                 600                 605

Pro Gly Asn Gln Gly Ser Pro Gly Gln Pro Gly Asn Pro Gly Gln Pro
    610                 615                 620

Gly Glu Gln Gly Lys Pro Gly Asn Gln Gly Pro Ala Gly Gly
625                 630                 635
```

<210> SEQ ID NO 25
<211> LENGTH: 2003
<212> TYPE: DNA
<213> ORGANISM: Artificial sequence
<220> FEATURE:
<223> OTHER INFORMATION: Complementary DNA sequence(CDS:1-1992) that encodes Exendin-4/GLK1076

<400> SEQUENCE: 25

```
ctcgagaaaa gagaggctga agctcacggt gagggtactt tcacttctga cttgtctaag      60

caaatggagg aggaggctgt tagattgttc attgagtggt tgaagaacgg tggtccatct     120

tctggtgctc caccaccatc tggtccacct ggtgaagacg gagataaggg agagatcggg     180

gagccggggc agaaaggaag caagggggac aaaggagaac agggtcctcc tgggcctaca     240

ggtcctcaag gccccatcgg acagccaggc ccctctggag ctgacggcga gccggggcct     300

cggggccagc agggcctttt cgggcagaaa ggtgatgaag gtcccagagg ctttcctgga     360

ccccctgggc cagtggggct gcagggtttg ccaggacctc caggcgagaa gggtgagaca     420

ggagacgtgg gccagatggg ccccccgggt ccacctggag aagacggaga taagggagag     480

atcggggagc cggggcagaa aggaagcaag ggggacaaag gagaacaggg tcctcctggg     540

cctacaggtc ctcaaggccc catcggacag ccaggcccct ctggagctga cggcgagccg     600

gggcctcggg gccagcaggg ccttttcggg cagaaaggtg atgaaggtcc cagaggcttt     660

cctggacccc ctgggccagt ggggctgcag ggtttgccag gacctccagg cgagaagggt     720

gagacaggag acgtgggcca gatgggcccc ccgggtccac ctggagaaga cggagataag     780

ggagagatcg gggagccggg gcagaaagga agcaaggggg acaaaggaga acagggtcct     840

cctgggccta caggtcctca aggccccatc ggacagccag gcccctctgg agctgacggc     900
```

-continued

```
gagccggggc ctcggggcca gcagggcctt ttcgggcaga aaggtgatga aggtcccaga    960
ggctttcctg gaccccctgg gccagtgggg ctgcagggtt tgccaggacc tccaggcgag   1020
aagggtgaga caggagacgt gggccagatg ggcccccegg gtccacctgg agaagacgga   1080
gataagggag agatcgggga gccggggcag aaaggaagca agggggacaa aggagaacag   1140
ggtcctcctg ggcctacagg tcctcaaggc cccatcggac agccaggccc ctctggagct   1200
gacggcgagc cggggcctcg ggccagcag ggcctttteg ggcagaaagg tgatgaaggt   1260
cccagaggct ttcctggacc ccctgggcca gtggggctgc agggtttgcc aggacctcca   1320
ggcgagaagg gtgagacagg agacgtgggc cagatgggcc ccccgggtcc acctggagaa   1380
gacggagata agggagagat cggggagccg gggcagaaag gaagcaaggg ggacaaagga   1440
gaacagggtc ctcctgggcc tacaggtcct caaggcccca tcggacagcc aggcccctct   1500
ggagctgacg gcgagccggg gcctcggggc cagcagggcc ttttcgggca gaaaggtgat   1560
gaaggtccca gaggctttcc tggacccct gggccagtgg ggctgcaggg tttgccagga   1620
cctccaggcg agaagggtga gacaggagac gtgggccaga tgggcccccc gggtccacct   1680
ggagaagacg gagataaggg agagatcggg gagccggggc agaaaggaag caagggggac   1740
aaaggagaac agggtcctcc tgggcctaca ggtcctcaag gccccatcgg acagccaggc   1800
ccctctggag ctgacggcga gccggggcct cggggccagc agggcctttt cgggcagaaa   1860
ggtgatgaag gtcccagagg ctttcctgga ccccctgggc cagtggggct gcagggtttg   1920
ccaggacctc caggcgagaa gggtgagaca ggagacgtgg gccagatggg ccccccgggt   1980
ccacctggtg gataatagaa ttc                                           2003
```

<210> SEQ ID NO 26
<211> LENGTH: 656
<212> TYPE: PRT
<213> ORGANISM: Artificial sequence
<220> FEATURE:
<223> OTHER INFORMATION: Exendin-4/GLK1076

<400> SEQUENCE: 26

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Pro Pro Gly Glu Asp Gly Asp Lys
        35                  40                  45

Gly Glu Ile Gly Glu Pro Gly Gln Lys Gly Ser Lys Gly Asp Lys Gly
    50                  55                  60

Glu Gln Gly Pro Pro Gly Pro Thr Gly Pro Gln Gly Pro Ile Gly Gln
65                  70                  75                  80

Pro Gly Pro Ser Gly Ala Asp Gly Glu Pro Gly Pro Arg Gly Gln Gln
                85                  90                  95

Gly Leu Phe Gly Gln Lys Gly Asp Glu Gly Pro Arg Gly Phe Pro Gly
            100                 105                 110

Pro Pro Gly Pro Val Gly Leu Gln Gly Leu Pro Gly Pro Pro Gly Glu
        115                 120                 125

Lys Gly Glu Thr Gly Asp Val Gly Gln Met Gly Pro Pro Gly Pro Pro
    130                 135                 140

Gly Glu Asp Gly Asp Lys Gly Glu Ile Gly Glu Pro Gly Gln Lys Gly
145                 150                 155                 160

Ser Lys Gly Asp Lys Gly Glu Gln Gly Pro Pro Gly Pro Thr Gly Pro
```

-continued

```
                165                 170                 175

Gln Gly Pro Ile Gly Gln Pro Gly Pro Ser Gly Ala Asp Gly Glu Pro
            180                 185                 190

Gly Pro Arg Gly Gln Gln Gly Leu Phe Gly Gln Lys Gly Asp Glu Gly
        195                 200                 205

Pro Arg Gly Phe Pro Gly Pro Pro Gly Pro Val Gly Leu Gln Gly Leu
    210                 215                 220

Pro Gly Pro Pro Gly Glu Lys Gly Glu Thr Gly Asp Val Gly Gln Met
225                 230                 235                 240

Gly Pro Pro Gly Pro Pro Gly Glu Asp Gly Asp Lys Gly Glu Ile Gly
                245                 250                 255

Glu Pro Gly Gln Lys Gly Ser Lys Gly Asp Lys Gly Glu Gln Gly Pro
            260                 265                 270

Pro Gly Pro Thr Gly Pro Gln Gly Pro Ile Gly Gln Pro Gly Pro Ser
        275                 280                 285

Gly Ala Asp Gly Glu Pro Gly Pro Arg Gly Gln Gln Gly Leu Phe Gly
    290                 295                 300

Gln Lys Gly Asp Glu Gly Pro Arg Gly Phe Pro Gly Pro Pro Gly Pro
305                 310                 315                 320

Val Gly Leu Gln Gly Leu Pro Gly Pro Pro Gly Glu Lys Gly Glu Thr
                325                 330                 335

Gly Asp Val Gly Gln Met Gly Pro Pro Gly Pro Pro Gly Glu Asp Gly
            340                 345                 350

Asp Lys Gly Glu Ile Gly Glu Pro Gly Gln Lys Gly Ser Lys Gly Asp
        355                 360                 365

Lys Gly Glu Gln Gly Pro Pro Gly Pro Thr Gly Pro Gln Gly Pro Ile
    370                 375                 380

Gly Gln Pro Gly Pro Ser Gly Ala Asp Gly Glu Pro Gly Pro Arg Gly
385                 390                 395                 400

Gln Gln Gly Leu Phe Gly Gln Lys Gly Asp Glu Gly Pro Arg Gly Phe
                405                 410                 415

Pro Gly Pro Pro Gly Pro Val Gly Leu Gln Gly Leu Pro Gly Pro Pro
            420                 425                 430

Gly Glu Lys Gly Glu Thr Gly Asp Val Gly Gln Met Gly Pro Pro Gly
        435                 440                 445

Pro Pro Gly Glu Asp Gly Asp Lys Gly Glu Ile Gly Glu Pro Gly Gln
    450                 455                 460

Lys Gly Ser Lys Gly Asp Lys Gly Glu Gln Gly Pro Pro Gly Pro Thr
465                 470                 475                 480

Gly Pro Gln Gly Pro Ile Gly Gln Pro Gly Pro Ser Gly Ala Asp Gly
                485                 490                 495

Glu Pro Gly Pro Arg Gly Gln Gln Gly Leu Phe Gly Gln Lys Gly Asp
            500                 505                 510

Glu Gly Pro Arg Gly Phe Pro Gly Pro Pro Gly Pro Val Gly Leu Gln
        515                 520                 525

Gly Leu Pro Gly Pro Pro Gly Glu Lys Gly Glu Thr Gly Asp Val Gly
    530                 535                 540

Gln Met Gly Pro Pro Gly Pro Pro Gly Glu Asp Gly Asp Lys Gly Glu
545                 550                 555                 560

Ile Gly Glu Pro Gly Gln Lys Gly Ser Lys Gly Asp Lys Gly Glu Gln
                565                 570                 575

Gly Pro Pro Gly Pro Thr Gly Pro Gln Gly Pro Ile Gly Gln Pro Gly
            580                 585                 590
```

```
Pro Ser Gly Ala Asp Gly Glu Pro Gly Pro Arg Gly Gln Gln Gly Leu
        595                 600                 605

Phe Gly Gln Lys Gly Asp Glu Gly Pro Arg Gly Phe Pro Gly Pro Pro
    610                 615                 620

Gly Pro Val Gly Leu Gln Gly Leu Pro Gly Pro Pro Gly Glu Lys Gly
625                 630                 635                 640

Glu Thr Gly Asp Val Gly Gln Met Gly Pro Pro Gly Pro Pro Gly Gly
                645                 650                 655


<210> SEQ ID NO 27
<211> LENGTH: 604
<212> TYPE: DNA
<213> ORGANISM: Artificial sequence
<220> FEATURE:
<223> OTHER INFORMATION: Complementary DNA sequence(CDS:13-591) that
      encodes EPO

<400> SEQUENCE: 27

gctagcgcca ccatgggggt gcacgaatgt cctgcctggc tgtggcttct cctgtccctg     60

ctgtcgctcc ctctgggcct cccagtcctg ggcgccccac cacgcctcat ctgtgacagc    120

cgagtcctgg agaggtacct cttggaggcc aaggaggccg agaatatcac gacgggctgt    180

gctgaacact gcagcttgaa tgagaatatc actgtcccag acaccaaagt taatttctat    240

gcctggaaga ggatggaggt cgggcagcag gccgtagaag tctggcaggg cctggccctg    300

ctgtcggaag ctgtcctgcg gggccaggcc ctgttggtca actcttccca gccgtgggag    360

cccctgcagc tgcatgtgga taaagccgtc agtggccttc gcagcctcac cactctgctt    420

cgggctctgg gagcccagaa ggaagccatc tcccctccag atgcggcctc agctgctcca    480

ctccgaacaa tcactgctga cactttccgc aaactcttcc gagtctactc caatttcctc    540

cggggaaagc tgaagctgta cacaggggag gcctgcagga caggggacag aggtccaccc    600

ggtg                                                                 604


<210> SEQ ID NO 28
<211> LENGTH: 20
<212> TYPE: DNA
<213> ORGANISM: Artificial sequence
<220> FEATURE:
<223> OTHER INFORMATION: Forward primer of GLK1074

<400> SEQUENCE: 28

ggtccacctg gtgaagacgg                                                 20


<210> SEQ ID NO 29
<211> LENGTH: 28
<212> TYPE: DNA
<213> ORGANISM: Artificial sequence
<220> FEATURE:
<223> OTHER INFORMATION: Reverse primer of GLK1074

<400> SEQUENCE: 29

gcggccgcct attatccacc aggtggac                                        28


<210> SEQ ID NO 30
<211> LENGTH: 1841
<212> TYPE: DNA
<213> ORGANISM: Artificial sequence
<220> FEATURE:
<223> OTHER INFORMATION: Complementary DNA sequence(CDS:13-1830) that
      encodes EPO/GLK1074
```

<400> SEQUENCE: 30

```
gctagcgcca ccatgggggt gcacgaatgt cctgcctggc tgtggcttct cctgtccctg     60
ctgtcgctcc ctctgggcct cccagtcctg ggcgccccac cacgcctcat ctgtgacagc    120
cgagtcctgg agaggtacct cttggaggcc aaggaggccg agaatatcac gacgggctgt    180
gctgaacact gcagcttgaa tgagaatatc actgtcccag acaccaaagt taatttctat    240
gcctggaaga ggatggaggt cgggcagcag gccgtagaag tctggcaggg cctggccctg    300
ctgtcggaag ctgtcctgcg gggccaggcc ctgttggtca actcttccca gccgtgggag    360
cccctgcagc tgcatgtgga taaagccgtc agtggccttc gcagcctcac cactctgctt    420
cgggctctgg gagcccagaa ggaagccatc tcccctccag atgcggcctc agctgctcca    480
ctccgaacaa tcactgctga cactttccgc aaactcttcc gagtctactc caatttcctc    540
cggggaaagc tgaagctgta cacaggggag gcctgcagga caggggacag aggtccacct    600
ggtgaagacg gagataaggg agagatcggg gagccggggc agaaaggaag caagggggac    660
aaaggagaac agggtcctcc tggcctaca ggtcctcaag gccccatcgg acagccaggc    720
ccctctggag ctgacggcga gccggggcct cggggccagc agggcctttt cgggcagaaa    780
ggtgatgaag gtcccagagg ctttcctgga ccccctgggc cagtggggct gcagggtttg    840
ccaggacctc caggcgagaa gggtgagaca ggagacgtgg gccagatggg ccccccgggt    900
ccacctggag aagacggaga taagggagag atcggggagc cggggcagaa aggaagcaag    960
ggggacaaag gagaacaggg tcctcctggg cctacaggtc ctcaaggccc catcggacag   1020
ccaggcccct ctggagctga cggcgagccg gggcctcggg gccagcaggg ccttttcggg   1080
cagaaaggtg atgaaggtcc cagaggcttt cctggacccc ctgggccagt ggggctgcag   1140
ggtttgccag gacctccagg cgagaagggt gagacaggag acgtgggcca gatgggcccc   1200
ccgggtccac ctggagaaga cggagataag ggagagatcg gggagccggg gcagaaagga   1260
agcaaggggg acaaaggaga acagggtcct cctgggccta caggtcctca aggccccatc   1320
ggacagccag gcccctctgg agctgacggc gagccggggc ctcggggcca gcagggcctt   1380
ttcgggcaga aaggtgatga aggtcccaga ggctttcctg gaccccctgg gccagtgggg   1440
ctgcagggtt tgccaggacc tccaggcgag aagggtgaga caggagacgt gggccagatg   1500
ggccccccgg gtccacctgg agaagacgga gataagggag agatcgggga gccggggcag   1560
aaaggaagca agggggacaa aggagaacag ggtcctcctg ggcctacagg tcctcaaggc   1620
cccatcggac agccaggccc ctctggagct gacggcgagc cggggcctcg gggccagcag   1680
ggccttttcg ggcagaaagg tgatgaaggt cccagaggct ttcctggacc ccctgggcca   1740
gtggggctgc agggtttgcc aggacctcca ggcgagaagg gtgagacagg agacgtgggc   1800
cagatgggcc ccccgggtcc acctggtgga taatagaatt c                       1841
```

<210> SEQ ID NO 31
<211> LENGTH: 579
<212> TYPE: PRT
<213> ORGANISM: Artificial sequence
<220> FEATURE:
<223> OTHER INFORMATION: rEPO/GLK1074, fusion protein

<400> SEQUENCE: 31

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30
```

-continued

```
Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg Gly Pro Pro Gly Glu Asp Gly Asp Lys Gly
                165                 170                 175

Glu Ile Gly Glu Pro Gly Gln Lys Gly Ser Lys Gly Asp Lys Gly Glu
            180                 185                 190

Gln Gly Pro Pro Gly Pro Thr Gly Pro Gln Gly Pro Ile Gly Gln Pro
        195                 200                 205

Gly Pro Ser Gly Ala Asp Gly Glu Pro Gly Pro Arg Gly Gln Gln Gly
    210                 215                 220

Leu Phe Gly Gln Lys Gly Asp Glu Gly Pro Arg Gly Phe Pro Gly Pro
225                 230                 235                 240

Pro Gly Pro Val Gly Leu Gln Gly Leu Pro Gly Pro Pro Gly Glu Lys
                245                 250                 255

Gly Glu Thr Gly Asp Val Gly Gln Met Gly Pro Pro Gly Pro Pro Gly
            260                 265                 270

Glu Asp Gly Asp Lys Gly Glu Ile Gly Glu Pro Gly Gln Lys Gly Ser
        275                 280                 285

Lys Gly Asp Lys Gly Glu Gln Gly Pro Pro Gly Pro Thr Gly Pro Gln
    290                 295                 300

Gly Pro Ile Gly Gln Pro Gly Pro Ser Gly Ala Asp Gly Glu Pro Gly
305                 310                 315                 320

Pro Arg Gly Gln Gln Gly Leu Phe Gly Gln Lys Gly Asp Glu Gly Pro
                325                 330                 335

Arg Gly Phe Pro Gly Pro Pro Gly Pro Val Gly Leu Gln Gly Leu Pro
            340                 345                 350

Gly Pro Pro Gly Glu Lys Gly Glu Thr Gly Asp Val Gly Gln Met Gly
        355                 360                 365

Pro Pro Gly Pro Pro Gly Glu Asp Gly Asp Lys Gly Glu Ile Gly Glu
    370                 375                 380

Pro Gly Gln Lys Gly Ser Lys Gly Asp Lys Gly Glu Gln Gly Pro Pro
385                 390                 395                 400

Gly Pro Thr Gly Pro Gln Gly Pro Ile Gly Gln Pro Gly Pro Ser Gly
                405                 410                 415

Ala Asp Gly Glu Pro Gly Pro Arg Gly Gln Gln Gly Leu Phe Gly Gln
            420                 425                 430

Lys Gly Asp Glu Gly Pro Arg Gly Phe Pro Gly Pro Pro Gly Pro Val
        435                 440                 445
```

-continued

```
Gly Leu Gln Gly Leu Pro Gly Pro Pro Gly Glu Lys Gly Glu Thr Gly
    450                 455                 460

Asp Val Gly Gln Met Gly Pro Pro Gly Pro Pro Gly Glu Asp Gly Asp
465                 470                 475                 480

Lys Gly Glu Ile Gly Glu Pro Gly Gln Lys Gly Ser Lys Gly Asp Lys
                485                 490                 495

Gly Glu Gln Gly Pro Pro Gly Pro Thr Gly Pro Gln Gly Pro Ile Gly
            500                 505                 510

Gln Pro Gly Pro Ser Gly Ala Asp Gly Glu Pro Gly Pro Arg Gly Gln
        515                 520                 525

Gln Gly Leu Phe Gly Gln Lys Gly Asp Glu Gly Pro Arg Gly Phe Pro
    530                 535                 540

Gly Pro Pro Gly Pro Val Gly Leu Gln Gly Leu Pro Gly Pro Pro Gly
545                 550                 555                 560

Glu Lys Gly Glu Thr Gly Asp Val Gly Gln Met Gly Pro Pro Gly Pro
                565                 570                 575

Pro Gly Gly
```

NONNATURAL COLLAGEN-LIKE PROTEIN AND USE THEREOF

CROSS REFERENCE TO RELATED PATENT APPLICATION

The present application is the US national stage of PCT/CN2009/075039 filed on Nov. 19, 2009 and claims the priority of the same PCT application No. PCT/CN2009/075039 filed on Nov. 19, 2009, which PCT application is incorporated herein by reference.

FIELD OF THE INVENTION

The present invention relates to the field of protein, in particular the preparation and application of a kind of innovative long-acting biologically active recombinant fusion proteins.

BACKGROUND OF THE INVENTION

On account of the clearance by kidney, liver and other unclear factors, most of the therapeutic bioactive peptides/proteins are often rapidly cleared in body, and their half-life generally ranges from only a few minutes to several hours. During therapeutic treatment, larger dosage and frequent injections are required to maintain effective drug concentration, which does not only mean a lot of pain to patients, but also decreases curative effect and increases the toxicity due to the fluctuation of plasma concentration.

Today, there are several ways have been reported to extend the half-life of bioactive peptides/proteins in vivo. Such as modifying bioactive peptides/proteins with water-soluble polymers (e.g., polyethylene glycol, dextran, etc.), which has been successfully applied, like PEG-ADA, PEG-IFNα and so on. The modification could prolong the half-life in vivo, increase stability and solubility, reduce immunogenicity and so on. But still there've been lots of problems with these modifications. First of all, the bioactivity of the proteins/peptides modified with chemical are generally decreased significantly or even inactivated (Veronese F M, Biomaterials, 22:405-417, 2001). Second, the way the polymers connecting to proteins/peptides is generally by forming covalent bond with amidogen, hydroxyl radical, imidazolyl radical and/or other chemical groups located on the surface of the proteins/peptides. However, most of the proteins/peptides have large molecule weight and complex structure. There would be multiple potential groups that may reactive with activated PEG. So the stability, bioactivity and/or other characters of the product varied if different sites are linked to PEG. What is more, most of the chemical synthetic polymers, such as PEG, can not be degraded by organisms. For example, it has been found that long-term and high-dose injection of PEG-interferon (PEG-IFNα2a) would accumulate in the kidney (Conover C D et al., Artificial Organs., 21:369-3 78,1997; Bendele A et al., Toxicol Sci., 42:152-157, 1998). From drug design perspective, drugs without accumulation would clearly be more secure. On the other hand, PEG-modified proteins have been found to produce a PEG antibodies (defined as multivalent hapten) which consequently affect the half-life of the drugs (Caliceti P & Veronese F M, Adv Drug Deliv Rev., 55:1261-1277, 2003).

Because of these technical problems, although it has been available to improve the pharmacokinetic profile of proteins/peptides in vivo by chemical modification for a long time, there are few chemical modified proteins/peptides been used in clinical practice.

It's also available to improve the stability of proteins/peptides in vitro and to prolong its half-life in vivo by fusion with some specific carrier protein. As described in the U.S. Pat. Nos. 5,876,969 and 5,766,88 and 7,176,278, the half-life of bioactive peptides/protein was improved after fusion with albumin, Fc fragment of antibody, transferrin (fragment/mutant of transferrin). The mechanism why these fusion proteins can extend the half-life is attributing to carrier protein's long in vivo half-life. To be a perfect carrier protein should have the following characteristics: 1. longer half-life in vivo; 2. Non-immunogenicity; 3. without biological function that unrelated to extending the half-life; 4. Not affect the bioactivity of the fused therapeutic proteins. However, there are no any solutions in public that may meet all of the above requirements until now. The first problem is the increase of immunogenicity, such as Fc fragment, of which the structure is not conservative. It is easy to cause the immune response because of the diverse sequence and structure. In addition, these carrier proteins usually have some biological effects, for example, Fc fragment can bind to complement (Fc receptor) to cause allergy, phagocytosis regulation, cell damage effect, etc. HSA usually partakes in the transport and metabolism of many substances. For a carrier protein, the existence of these biological characteristics is negative. Moreover, these carrier proteins themselves have complex spatial structure, which would decrease the activity of the fused bioactive protein due to the steric effect (Baggio L L et al., Diabetes., 53: 2492-2500, 2004; Huang Y S et al., Eur J Pharm Biopharm., 67:301-308, 2007).

In summary, the existing technology to extend the in vivo half-life of therapeutic proteins have the following drawbacks: 1. heterogeneous products, complex technological requirements; 2. what used to modify the protein cannot be degraded by organism, and would accumulate in vivo; 3. to increase the immunogenicity; 4. resulting in a significant reduction or even complete loss of the bioactivity of fused proteins; 5. may bring in unneeded side biological effect. Neither chemical modifications, nor fusion with carrier protein can completely avoid the above disadvantages.

In order to avoid the disadvantages of these natural carrier protein like albumin or Fc fragment, the artificial amino acid sequences has been tried as a carrier protein. David W. Leung etc. artificially synthesized poly-glutamate as a fusion carrier to prolong the half-life of protein drugs (US 20080176288). Synthetic poly-glycine has also been tried as a fusion vector (Schlapschy M et al., Protein Eng Des Sel., 20:273-284, 2007). There are other fusion vectors artificially synthesized with hydrophilic amino acids(like Gly, Asp, Glu, Ser, etc al) in alternative to extend the half-life of protein drugs as well. However, it's complicated to predict actual effects of the completely artificially synthetic fusion carriers. There would be many problems. For example, 1. Due to the complex relation between structure and the function of protein, it is difficult to predict the actual high order structure (such as secondary and tertiary structure) of the one synthesized exactly to be the one designed, and so it is difficult to predict the potential biological activity and immunogenicity; 2. Artificially designed repetitive sequences, especially those highly repetitive ones, are often different from the natural developed ones and are hard to be expressed because the actual expression levels are often too low to apply in practice. The inventor have tried to construct a recombinant poly-Glu as a fusion carrier to extend the half-life of protein drugs according to David W. Leung, etc. (US20080176288), but it was impracticable actually.

Therefore, it's urgently needed to develop a simple and effective technological solution that can improve the residence time of protein/peptides both in vitro and in vivo and with little or none side effects.

SUMMARY OF THE INVENTION

The present disclosure is directed to compositions and approaches that can be more useful for enhancing the biological, pharmaceutical, safety and/or therapeutic properties of biologically active proteins compared to the existing technology. The compositions and approaches are particularly useful for enhancing the pharmacokinetic properties, such as half-life, and simplifying the production process of such a biologically active protein.

In the first aspect, the present invention provides compositions of extended gelatin-like recombinant protein (GLK), that when linked to a biologically active protein enhances the pharmacokinetic properties of the resulting fusion protein in the configuration of formula I (Gly-X-Y) n Wherein, Gly is glycine residues;

X and Y are selected from the 20 kinds of natural amino acid residues except for cysteine residue, respectively;

n=20-300;

wherein, the gelatin-like units as described has the following characteristics:

(a) the sum of Asn, Asp, Gln, Glu, Lys, Pro, Ser, Hyp and Arg is 40% to ⅔ (66.7%);

(b) the ratio of total Pro and Hyp to n is ≥0.6;

(c) the ratio of total Gly to n is ≤1.15 (preferably ≤1.05);

In addition, the gelatin-like units as described aren't natural gelatin.

In one preferred embodiment, the gelatin-like units as described also have the following characteristics:

(d) the isoelectric point is 3-7 (preferably ranging from 3.2 to 6, more preferably ranging from 3.2 to 5.5);

(e) in line with the Kolaskar-Tongaonkar calculation method, the average antigenic propensity is not higher than 0.98;

(f) the hydrophilic indicator GRAVY value calculated by ProtParam, is less than −1.1 (preferably less than −1.4, more preferably less than −1.5).

In one embodiment, the sequences of the gelatin-like units as described derive from the sequence of gelatin. For example, the hydrophobic amino acids (e.g. Ile, Leu, Met, Phe, Val) in gelatin corresponding to X, Y may be partially or completely substituted by hydrophilic amino acids, which are preferred to be one and/or several of the following ones, Ala, Asn, Gln, Glu, Lys, Pro, Ser, Hyp, Arg, that could make the GRAVY value of the re-designed sequence is less than −1.4.

In another embodiment, the molecular weight of the gelatin-like units as described is 10-100 kDa.

In the second aspect of the present invention, it provides a series of polynucleotide which could encode the gelatin-like units as described in the first aspect of the present invention.

In the third aspect of the present invention, it provides a kind of recombinant fusion proteins characterized in that it's formed by fusing the biologically active proteins/peptides and the gelatin-like units as described in the first aspect of the present invention.

In some embodiments, the improved pharmacokinetic property of resulting fusion protein encompasses an increase in terminal half-life of at least two fold, or at least three-fold, or at least four-fold, or at least five-fold, or at least six-fold, or at least ten-fold, compared to the corresponding biologically active protein/peptide not fused with GLK.

In one embodiment, the ratio of the apparent molecular weight (gel filtration analysis) of the recombinant fusion protein as described to the theoretical one is ≥1.25, preferably ≥1.5, more preferably ≥2.

In some embodiments, the molecular weight of the biologically active proteins/peptides as described is 0.5-70 Kda, preferably 1-66 Kda.

In some embodiments, the gelatin-like units as described are located beside either or both, or between the amino terminal and the C-terminus of the fusion proteins.

In some embodiments, the recombinant fusion protein as described is monomer or multi-polymer.

In some embodiments, the recombinant fusion protein as described is monomer or multi-polymer of formula (I), {GLK}p-R-{GLK}q (I)

Wherein,

GLK refers to the gelatin-like units as described in the first aspect of the present invention;

p and q is independently 0 or 1, and p and q should not both be 0;

R represents some kind of biologically active protein except for gelatin or gelatin-like units as described above; and "—" represents the peptide bond.

In one embodiment, the number of (Gly-X-Y) fragment contained in the recombinant fusion protein as described is greater than 20, and less than 300.

In another embodiment, the molecular weight of the recombinant fusion proteins as described is 20-500 Kda.

In some cases, recombinant fusion proteins as described in formula (I) are multi-polymers, wherein each R and GLK may either be the same or be different.

In the fourth aspect of the present invention, it provides a variety of polynucleotide, which encodes the recombinant fusion protein as described in the third aspect of the present invention.

In the fifth aspect of the present invention, it provides a variety of expression vectors into which the polynucleotide as described in fourth aspect of the present invention were inserted.

In the sixth aspect of the present invention, it provides a variety of recombinant host cells, which are transformed with the expression vectors as described in the fifth aspect of the present invention, or of which the chromosome is integrated with the polynucleotide as described in fourth aspect of the present invention.

In the seventh aspect of the present invention, it provides an approach to prepare the recombinant fusion protein of any of the foregoing embodiments, of which the process includes steps of:

providing a host cell, which can comprise an expression vector disclosed in the foregoing paragraph and the approaches of production of the foregoing fusion proteins.

DETAILED DESCRIPTION OF THE EMBODIMENTS

Figure 1:
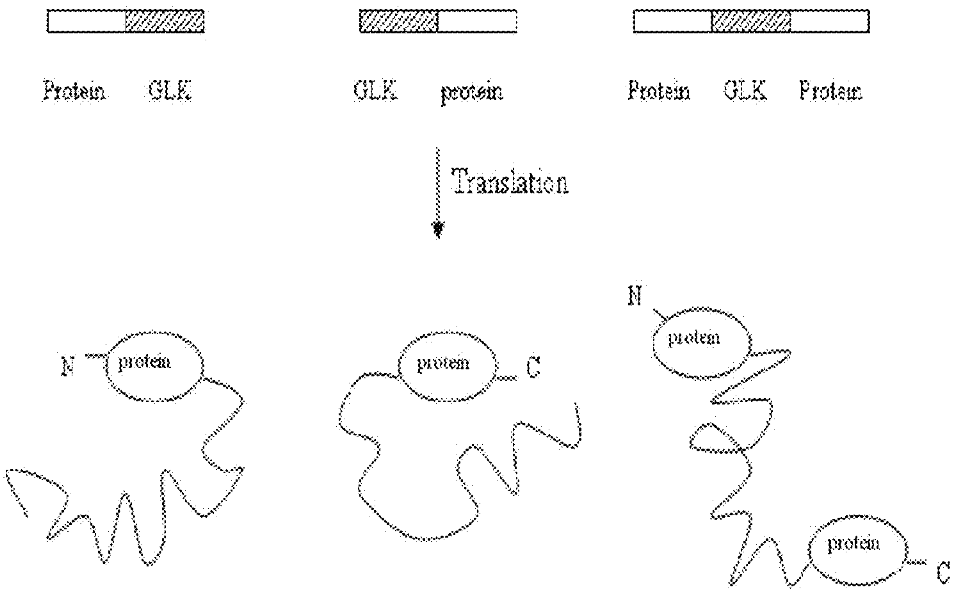
FIG. 1 shows several typical structures of the recombinant fusion protein linked with gelatin-like units.

It was the first time that the present inventor found that the recombinant gelatin-like protein (gelatin like protein, GLK) is a kind of perfect fusion carrier based on a mass of research and screening. The present inventor used gelatin-like protein as fusion carrier and fused with bioactive peptides/proteins, which did significantly extend the half-life of bioactive peptides/proteins in vivo.

In detail, experiments demonstrated that fusion with the gelatin-like protein would significantly improve the stability of bioactive protein in vitro, and more importantly, would prolong its half-life in vivo through reducing the clearance rate and changing the pharmacokinetic distribution.

It's not difficult to understand that the present invention includes but is not limited to those specific methods, procedures, cell lines, vectors and reagents being described following. In addition, the terminologies used herein are only to describe a particular embodiment, but not to deliberately limit the scope of the present invention. Unless otherwise limited, the technology and the terminologies used herein are just what they mean to a general technician in this technological field. There are only some preferred methods, devices and materials described in the present invention, and other methods and materials, which are similar or equivalent to the description in this invention, could also be used to practice or test the invention.

Definitions

Gelatin-Like Units

As used herein, the term "gelatin-like units", "gelatin-like protein", or "GLK (gelatin-like protein)" are used interchangeably.

Natural derived gelatin is a kind of protein derived from collagen, and it's the product of the degradation of collagen. There are many repetitive Gly-X-Y triplets in natural gelatin and it has a general formula of $(Gly\text{-}X\text{-}Y)_n$, wherein X and Y are often proline and hydroxyproline residues. The amino acid composition of X and Y would affect the polarity, isoelectric point, secondary structure, immunogenicity and other features of gelatin.

Gelatin can be prepared from the bones and fur of animals. However, usually there would be invasive virus remained in gelatin derived from animals. In addition, there are still biocompatibility issues with the application of animal-derived gelatin in human beings.

Because of the development of molecular biology, it became possible to obtain human sequence derived gelatin with high homogeneity by using recombinant DNA technology. Currently, there were a lot of reports about expression of recombinant human-derived collagen or gelatin by microorganisms, animal cells or plants (U.S. Pat. Nos. 5,593,859; 6,428,978; 6,617,431; Werten M W et al., Yeast, 15: 1087-1096, 1999). The biochemical property of recombinant gelatin varies with the collagenic gene fragment used to encoding it. And it showed that the *pichia pastoris* expression system can be used to produce recombinant gelatin or gelatin-like protein that from different source and with unique biochemical properties (Olsen D et al., Adv Drug Deliv Rev., 55:1547-1567, 2003). Recombinant gelatin has the same ability to stabilize protein as the natural gelatin does, and has been used as a vaccine stabilizer (US 2006/0204511 A1).

In the present invention, gelatin-like units refers to the peptides expressed by recombinant DNA technologies and with the sequence derived from natural gelatin, as well as the re-designed ones that are characterized by the (Gly-X-Y)n structure similar to natural gelatin.

In the present invention, there is no particular limit to the molecular weight and the length of gelatin-like units. By the term of length, each unit usually contains 60-1500 amino acid residues, preferably 200-1000 amino acid residues; by the term of molecular weight, each unit is usually 6-150 KDa, preferably 20-80 KDa.

Recombinant Fusion Protein with Gelatin-Like Units

The present invention relates to a new class of recombinant fusion protein with gelatin-like units, which consist of one or more natural/artificial bioactive proteins and gelatin-like units, and which has diagnostic/therapeutic/targeting function. Recombinant fusion protein with gelatin-like units is a monomer/polymer with the following basic structure: {GLK}p-R-{GLK}q, wherein, GLK refers to the gelatin-like units; p and q is independently 0 or 1, and p and q should not be both 0; R represents some kind of bioactive protein other than gelatin, and which is free of gelatin-like units as described; when the recombinant fusion protein is a polymer, the structure could be {$GLK_1$}p-$R_1$-{$GLK_2$}q-{$GLK_3$}p-$R_2$, {$GLK_1$}p-$R_1$-{$GLK_2$}q-{$GLK_3$}p-$R_2$-{$GLK_4$}q, {$GLK_1$}p-$R_1$-{$GLK_2$}q-{$GLK_3$}p-$R_2$-{$GLK_4$}q-{$GLK_5$}p-$R_3$-{$GLK_6$}q, et al., wherein $R_{1-3}$ can be the same or different, and $GLK_{1-6}$ can be the same or different, but there should be one GLK and one bioactive protein (such as R1 or R2) at least. FIG. 1 shows several typical basic structures of the recombinant fusion protein with gelatin-like units.

The present invention provides a recombinant fusion protein consisting of one or more bioactive proteins/peptides and one or more gelatin-like units(GLK) with specific molecular weights, wherein GLK does not have any immunogenicity, and has excellent water-solubility under physiological conditions. The recombinant fusion protein as described does not only show better stability in vitro and longer half-life in vivo, but also the homogenous structure and higher biological activity unexpectedly compared with the fusion protein produced trough the existing chemical modification technology or other fusion protein technology. What's more, as a kind of fusion carrier for therapeutic purpose, the advantages of GLK include good biocompatibility, non-immunogenicity, non-accumulation in vivo for it can be degraded by organism, and so on.

Herein, the "recombinant fusion protein with gelatin-like units" refers to a protein with the following basic structure: {GLK}p-R-{GLK}q, wherein protein/peptide R and GLK are connected by peptide bond, or further more, by a spacer. By the term of "spacer", it refers to one or more molecules, such as amino acids, nucleic acids or chemical molecules like polyethylene glycol (PEG), and so on. Spacer can be used to provide the target site of the necessary components to facilitate the operation; also it can be used to maintain the space structure of the active protein, or to the benefit of the interaction between the active protein and the target. For the present invention, it's most suitable for short linker peptides to be spacers, such as peptides rich in Gly and Ser, like $(GlyGlyGlyGlySer)_n$, wherein n ranges between 1 and 10; and peptides that already wildly used in connecting, like the peptides that Daming Shan had mentioned (Shan D et al., J Immunol., 162:6589-6595, 1999). Of course, GLK itself can also be used as a linker peptide. It's not difficult to understand that the portion of bioactive protein/peptide can also be repeated to act as a spacer as well, which would produce a fusion protein with one of the following structures: $R_1$-$R_1$-GLK, $R_1$-$R_1$-GLK-$R_2$, GLK-$R_1$-$R_1$, $R_1$-GLK-$R_2$ -$R_2$, $R_1$-$R_1$-GLK-$R_2$-$R_2$. FIG. 1 shows several typical basic structures of the recombinant fusion protein as described, and the structures are not limited to FIG. 1 according to the spirit of this invention.

GLK, the fusion carrier, has a highly repetitive gelatin-like domain (Gly-X-Y), of which the sequence can be completely or partially derived from natural gelatin, or be a simple repetition of the segmental sequences from natural gelatin, or be a optimized artificial re-designed sequence with the featured structure Gly-X-Y. Because it's similar among the sequences of gelatins derived from different species, the sequence of GLK can derived from human beings as well as non-human beings. Just like the segmental sequence of collagen α1 (I) as David Olsen mentioned in the article (Olsen D et al., Adv Drug Deliv Rev., 55:1547-1567, 2003). The sequence of GLK can be completely consistent with the natural sequence, or be a simple repetition (to match the size that the present invention required) of selected segment of a natural sequence. The GLK that may be used can come from a very wide range of sources. It can be used to prepare the recombinant fusion protein as described no matter it is derived from a natural one or it is a synthetic one with a featured structure $(Gly-X-Y)_n$ like the gelatin fragments referred in U.S. Pat. Nos. 5,801,045, 6,150,081, 6,428,978, WO01/34646A2, so long as it is soluble in water at <40° C. and does not elicit immunogenicity Furthermore, in order to better achieve the goal of the present invention, the inventor also re-designed a class of recombinant gelatin-like units based on the natural gelatin according to the following principles: 1. To select the (Gly-X-Y) units that higher abundant in natural gelatin, such as Gly-Pro-Hyp, Gly-Pro-Ala, Gly-Ala-Hyp, Gly-Glu-Lys, Gly-Pro-Lys, Gly -Glu-Hyp, Gly-Ser-Hyp, Gly-Gln-Hyp, Gly-Glu-Arg, Gly-Pro-Arg and so on, and then, to recombine them;

2. To select the (Gly-X-Y) units that rich in hydrophilic amino acids and to recombine them, wherein X, Y is preferred to be hydrophilic amino acids, and it will be better that they are one or more of the following amino acid residues: Ala, Asn, Gln, Glu, Lys, Pro, Ser, Hyp and Arg;

3. To avoid the sequence containing know immunogenic sequences as far as possible, such as the immunogenic ones that has already been disclosed in openly published technical documentation, like Ile-Pro-Gly-Glu-Phe-Gly-Leu-Pro-Gly-Pro (Hori H et al., J. Allergy Clin Immunol., 110:652-657, 2002);

4. To avoid the sequence containing know action site of protease as far as possible, such as signal peptidase KEX-2 site;

5. According to the Kolaskar-Tongaonkar calculation method, the average antigenic propensity of the re-designed gelatin-like units should not be higher than 0.98.

The artificially re-designed gelatin-like units are rich in hydrophilic amino acids, and the typical sequences of them are included but not limited to SEQ ID NO: 2,19,21 and so on.

The molecular weight of GLK changes with the number of the repetitive structure unit Gly-X-Y. In order to achieve the goal of the present invention, first of all, the molecular size of recombinant fusion protein must be appropriate to ensure that the fusion protein would not be eliminated through the filtration of the kidneys. The molecular weight of recombinant fusion protein is co-determined by proteins/peptides R and GLK. For a recombinant fusion protein with given activity, the molecular weight of bioactive protein R is certain and the molecular weight of the recombinant fusion protein will be determined by the size and number of GLK if the number of R is certain too,. When the molecular weight of protein/peptide R is small(such as <20 KD), the molecular weight of GLK should be at least between the 15-70 KD in order to avoid being cleared by renal glomerulus filtration. However, a higher molecular weight may not be more effective to extend the half-life of fusion protein in vivo and maybe harder to be prepared for it will be easier to be degraded by proteases and possibly be more immunogenic. Therefore, the appropriate molecular weight of GLK is 6-150 KD and it will be better to be 20-80 KD. When the size of proteins/peptides R is relatively large, or R can form dimer or polymer, the molecular weight of GLK can within the range of 1 kDa-150 KDa, for example, approximately 1000-2000 Da, 2-20 kDa, 20-50 kDa, 50-100 kDa, 100-150 kDa, 150-200 kDa.

There is no special limit in the molecular weight of the recombinant fusion protein with gelatin-like units. The molecular weight is usually 20-500 KDa, and it would be better to be 25-300 KDa.

Physiologically Active Proteins/Peptides

The term "physiologically active proteins/peptides" refers to proteins, antibodies, peptides and fragments or variants of, having one or more pharmacological and/or biological activity, or targeting guidance, polymerization and other functions. It can be naturally existed or artificially constructed. As a non-limiting embodiment, "Bioactive proteins/peptides" include enzymes, enzyme inhibitors, antigens, antibodies, hormones, coagulation factors, interferons, cytokines, growth factors, differentiation factors, bone growth-related factors, and factors related to bone absorption factors, chemotactic factors, cell motility factors, migration factors the mobile factor, cytostatic factors, bactericidal factors, antifungal factors, adhesion molecules in plasma, interstitial adhesion molecules and extracellular matrix, receptor ligands and their clips.

The biological activity of proteins/peptides of the invention, more specifically refers to the performance of a "therapeutic activity" of proteins/peptides, or "therapeutically active" of the protein/peptide, the protein/peptide with one or more already known biological and/or therapeutic activity. These activities are related to one or more therapeutic protein described here or other known therapeutic protein.

As a non-limiting embodiment, "therapeutic protein" refers to a protein used for treatment, prevention or improving disease, condition, or functional disorder. As a non-limiting embodiment, "therapeutic protein" may be one that binds specifically to a specific cell type (normal (eg, lymphocytes) or abnormal (eg cancer cells)) and therefor maybe used to target a compound (drugs, or cytotoxic agents) to that cell type specifically.

In another non-limiting embodiment, the "therapeutic protein" is a protein that has biological activities and in particular, is used for treating, preventing and improving a disease. Non-inclusive list of therapeutic activities that may be possessed by a therapeutic protein includes: increasing angiogenesis, inhibiting angiogenesis, regulating hematopoietic functions, stimulating nerve growth, enhancing the immune response, inhabiting an immune response.

As mentioned above in the same, "therapeutic activity" or "activity" can refer to an activity whose effect is consistent with desirable therapeutic outcome in humans, non-human mammals or other species of organisms. Therapeutic activity can be measured in vivo or in vitro.

In the present invention, embodiments of the mentioned therapeutic proteins include, but are not limited to: VEGF receptor, TNF receptor, HER-2/nerve membrane receptors, secreted form of human ErbB3 receptor isomers, transforming growth factor b III receptor extracellular domain, transforming growth factor b II receptor extracellular domain, IL-1 receptor, IL-4 receptor, urokinase, β-glucocerebroside lipase, arginine deiminase enzyme, Arginase, herstatin, epidermal growth factor, FGF-1, fibroblast growth factor-2, general fibroblast growth factor, nerve growth factor, platelet-derived growth factor, VEGF-1, IL-1, IL-2, IL-3, IL-4, IL-6, IL-8, IL-10, IL-11, IL-12, IL-18, IL-21, IL-24, IL-1RA, RANKL, RANK, OPG, LEPTIN, interferon α, interferon β, interferon γ, interferon-Ω, TGF-β, TGF-β-1, TGF-β-3, TNF α, atrial natriuretic peptide, B-natriuretic peptide, gonadotropin, human luteinizing hormone, follicle-stimulating hormone, human growth hormone, EPO, G-CSF, GM-CSF, TPO, M-CSF, SCF, VEGF, EPO mimetic peptide, TPO mimetic peptide, FLT3 ligands, Apo2 ligand, inhibit bone cell factor, BMP-2, BMP-7, GLP-1 and its analogs, Exendin-3, Exendin-4, insulin and its analogs, GIP, glucagon, endothelial inhibin (endostatin), plasminogen kringle 1 domain, plasminogen kringle 5 domain, angiostatin and so on. Therapeutic proteins can also be the antibodies and antibody fragments, single chain antibody scFv and so on. These proteins and nucleic acid sequences encoding these proteins are well-known, and can be found in public databases such as Chemical Abstracts Services Databases (eg CAS Registry), GenBank, and GenSeq. That most proteins, whose biological activity has already been found, are applicable to this invention for those skilled in the art. Of course, the same may be understood that this newly discovered biologically active proteins/peptides after the invention, also applies to the present invention.

In the invention, bioactive proteins fusion with the recombinant gelatin-like protein can be glycosylated or non-glycosylated. For example, some cytokines, cell surface proteins and secreted proteins, are often modified by the attachment of one or more oligosaccharide groups. There are generally two main types of glycosylation: glycosylation characterized by O-linked glycosylation, which is attached to serine or threonine residues; and glycosylation characterized by N-linked glycosylation, which is attached to asparagine residue in an Asn-X-Ser/Thr sequences, where X can be any amino acid except proline.

Glycosylated isomers can be produced by removing or introducing glycosylation sites, e.g., the substitution or deletion of amino acid residues, such as glutamate substitution for asparagine, or expression of unglycosylated proteins in host cells that will not glycosylated them, e.g., in *E. coli* or glycosylation-defection yeast.

Mechanism

Several mechanisms are involved in clearance of peptide/protein drugs from circulation including renal filtration, receptor-mediated endocytosis, proteolysis degradation, lymphatic elimination system, liver elimination and so on. As FcRn has been found to salve albumin and IgG form intracellular degradation by FcRn-mediated cycling system, active protein fusion with the Fc fragment of IgG or albumin can be maintained longer half-life.

The exact mechanisms of extending the half-life of the protein after fusion with gelatin have been not clear. There has no similar receptors been found to play a role so far. GLK sequence itself does not combine with FcRn. GLK/G-CSF fusion protein (in both G-CSF as a negative control) are added in human serum-coated 96 well microplates, washed after incubation, bound with G-CSF Antibody labeled with biotin (Abcam plc.), and colored by avidin-HRP system, The results shows that GLK fusion proteins don't not combine with the serum components, thus excluding the possibility that the GLK fusion protein may bind with some component in the serum. Additionally, there is no correlation between half life in vivo and molecular weight. Recent studies have shown that simply increasing molecular of the fusion protein does not prolong their half-life in vivo, e.g., Carlos A. (Buscaglia C A et al., Blood., 93:2025-2032, 1999) found that the half-life of large molecular weight TSac protein (76 KD) in vivo (about a few hours) is far less than the smaller molecular weight GST-Ag 36 (60 KD) (about 30 hours). Embodiment 7 also shows that the peptides, with gelatin-like proteins as fusion part, which have different sequence and the closely molecular weight, have different half-life in vivo.

It should be understood that the protective range of the present invention is not restrict to the mechanism of action. The present invention is to provide the following mechanisms which facilitate a better understanding of the present invention. The possible reasons that Recombinant gelatin-like fusion protein can increase the stability and half-life of the bioactive protein in vivo and in vitro, including:

(1) Y is often Pro (Hyp) in Gly-X-Y triplets, maintain a loose structure in the physical environment, protect the active proteins from degraded by in vivo protease.

(2) GLK structure is rich in hydrophilic amino acids, which forms very large hydrated molecular radius, and avoids elimination from kidney filtration. The rGLK$116_4$/G-CSF fusion protein whose theoretical molecular weight is about 55 KD, the apparent molecular weight is about 154 KD (apparent MW: Theory MW=2.8) with size exclusion chromatography analysis.

(3) The specific charge characteristic of GLK fusion protein led to the longer half-life in vivo. GLK in present invention has lower isoelectric point and a negative charge in normal physiological conditions. As many plasma proteins with mostly negative charge have a transport function, the gelatin-like recombinant fusion protein with negative charge reduced the possibility of combing with plasma protein, and can be retained in the plasma for longer time.

(4) The surface polysaccharide-protein complexes in vessel wall endothelial cells (glycocalyx) reduce the clearance of recombinant gelatin-like fusion protein. The vessel wall polysaccharide—protein controls the transport between blood vessels and surrounding matrix material (Simionescu M, Simionescu N, Annu. Rev. Physiol., 48: 279-293, 1986). Polysaccharide—protein complexes in the normal physiological conditions is negatively charged, while the gelatin-like fusion protein is also negatively charged, due to the rejection of the same charge, the fusion protein of recombinant gelatin-like reduce interaction with the glycocalyx, thereby reducing the recombinant gelatin-like fusion proteins penetrate from the blood to the tissue.

Preparation of Recombinant Gelatin-Like Fusion Protein

Fusion protein of the invention can be synthesized by direct solid-phase technology. The protein fragments of the invention can also be chemically synthesized, respectively, and then be connected chemically to produce full-length molecule. In the preferred embodiment, the fusion protein of the invention is prepared by recombinant methods.

Preparations of Gelatin-like fusion protein by recombinant methods in prokaryotic host, eukaryotic host, plant or animal include the expression and purification process. Any system which can express recombinant protein, including prokaryotic, eukaryotic, genetically modified plant and animal systems, can be used in the present invention. For example, U.S. Pat. No. 6,548,653 mentioned all the methods which used to express the fusion protein, are suitable for this present invention.

Explaining in details, in order to get the target recombinant gelatin-like fusion protein, we firstly need to obtain the required nucleotides coding recombinant gelatin-like fusion protein, the target nucleotide sequence can be prepared by a variety of conventional methods. In addition, in order to get the sequence of derivative or variants, nucleotide sequence can be modified or altered, for example, by genetic engineering techniques.

More preferably, in the present invention, the nucleotide sequences as part of the expression cassette contain the transcription initiation region (promoter sequences), which controls the expression of the nucleotide sequences in the host cell, and encode the polypeptide in the present invention. This region could be from highly expressed, constitutive or regulated-type gene promoter region in the used host. For example, for yeast, they can be promoters of methanol oxidase (AOX), phosphoglycerate kinase (PGK) and other similar gene. Expression cassette can also include functional transcription termination regions in the used host, which are closely connected to the downstream of coded nucleotides of polypeptide in the invention.

In a preferred scenario, there is a nucleotide sequence of a signal peptide prior to the nucleotide sequence encoding the peptides of the invention, which is used to guide the nascent polypeptide into the secretory pathway in its host.

In addition to the expression cassette, one or several tags can be added to screen recombinant host cell, such as the URA3 gene from yeast *S. cerevisiae*, G418 resistance gene from *pichia* yeast, or any other selective tag. Expression cassette with Selection marker unit can be directly introduced into the host cell, or pre-inserted into the expression vector with functional self-replicating The expression vector can be used very wide range of sources, including but not limited to: the expression plasmid pKD1 commonly used in *Kluyveromyces* yeast; the preferred plasmid is 2μ in yeast *Saccharomyces*; the expression plasmid pPIC9, pPIC9K, pPICZα used in pichia system and so on.

After the above mentioned recombinant expression plasmid was constructed, the recombinant plasmids was introduced into the selected host cells, and the host cell integrated with recombinant plasmid successfully was screened, according to common molecular biology literature, such as "Molecular Cloning A Laboratory Manual" third edition (Sambrook J, Russell D W, Molecular cloning: A laboratory manual. 3rd edition, New York: Cold Spring Harkbor Laboratory Press, 2001) or any conventional technology supplied by commercial company. Any conventional methods which can introduce the foreign DNA into the cells, such as transformation, electroporation, conjugation, etc, can be used. Any system which can express recombinant protein, including prokaryotic, eukaryotic, plant and animal transformation systems, can be used in the present invention.

After Screening, the transformed cells which express the fusion proteins would be inoculated and incubated. Fusion protein was harvested in the growth phase or in late growth stage during continuous culture, depending on the host cell expression characteristics. Fusion protein can be expressed in the host, such as most of the prokaryotic expression system, and can also be secreted in the medium, such as yeast, animal cell expression systems which are generally extracellular secretion systems). By combination of centrifugations, breaking strains, ultrafiltration, precipitation, chromatography and other methods, recombinant gelatin-like protein or recombinant gelatin-like active protein fusion protein can be highly purified. The purified fusion protein can be used for structural identification, in vivo biological activity determination, pharmacokinetics, or other purposes.

As differences of the expression vector and host strains, when recombinant gelatin-like protein is produced in some eukaryotic systems, the Pro amino acid may be partially or completely converted into Hyp, which does not affect the present invention results. Although in general there is no prolyl-4-hydroxylase (P4H) in yeast, by some special methods, the yeast system also allows some or all of Pro to convert into Hyp, for example, Vuorela (Vuorela et al., EMBO J., 16:6702-6712, 1997) and Vaughan (Vaughan et al., DNA cell Biol., 17:511-518, 1998) researches show that co-expression of gelatin and P4H gene can get the hydroxylated gelatin in *Saccharomyces cerevisiae* or *Pichia pastoris*.

Properties of the Recombinant Fusion Protein with Gelatin-Like Units (a) Physico-Chemical Properties the gelatin-like elements (Gly-X-Y) n of fusion protein described in the invention has the following partial or all of the physico-chemical properties:

(1) The percentages of sum of hydrophilic amino acids Asn, Asp, Gln, Glu, Lys, Pro, Ser, Hyp and Arg are high, total of 40% to ⅔ (66.7%);

(2) The ratio between the sum of Pro, Hyp and n is ≥0.6;

(3) The ratio between the sum of Gly and n is ≤1.15 (preferably ≤1.05);

(4) The isolectric point is 3-7 (preferably of 3.2-6, more preferably of 3.2-5.5);

(5) The average antigen index is not higher than 0.98, according to Kolaskar-Tongaonkar method;

(6) Calculated according to ProtParam, GRAVY value representing hydrophilic is less than −1.1 (better of less than −1.4, the better is less than −1.5).

40° C., after 48 hours shocking, rhG-CSF molecular was found to form a large number of polymer samples by size exclusion chromatography analysis and total protein content also decreased significantly, but rGLK116$_4$/G-CSF fusion protein changed little, indicating that fusion with the GLK significantly improved in vitro biological protein stability.

Recombinant gelatin-like fusion proteins improve protein biological activity and stability in vitro. The mechanism may be: gelatin sequences reacted with the exposed part of unfolding protein, which avoid the biological protein folding together. Fusion proteins improved stability in vitro, and reduced the protein to aggregates during preparation and storage thereby reduced the therapeutic protein immunogenicity which shows great clinical significance.

As the activity protein increased stability in vitro significantly after fusion with gelatin, and avoid the addition of HSA and other stabilizers, which reduced the risk of adding HSA, such as producing antibodies or neutralizing antibodies.

TABLE 1

Properties of GLKs involved in Example 1-12

| | Molecular weight (KD) | Hydrophilic amino acids composition (%) | GRAVY value [a] | Isoelectric point | SGly/n [b] | S(Pro + Hyp)/n [c] | The average antigen index [d] |
|---|---|---|---|---|---|---|---|
| GLK116$_4$ | 40.6 | 65.2 | −1.808 | 5.06 | 1.02 | 0.64 | 0.9393 |
| GLK104$_6$ | 55.0 | 65.4 | −1.777 | 4.93 | 1.01 | 0.67 | 0.9412 |
| GLK107$_6$ | 58.4 | 54.0 | −1.238 | 4.41 | 1.01 | 0.65 | 0.9640 |
| GLK420 | 38.4 | 53.6 | −1.121 | 4.78 | 1.01 | 0.78 | 0.9682 |

[a] GRAVY value: the average value of all hydrophilic value of amino acid in peptide or protein (the number of hydrophilic amino acids divided by the sum of amino acids) (Kyte J, Doolittle R F, J Mol Biol., 157: 105-132, 1982).

[b] SGly/n is the ratio between sum of Gly and n in GLK sequence.

[c] S (Pro + Hyp)/n: is the ratio between sum of Pro, Hyp and n in GLK sequence.

[d] Calculating the probability of each amino acid in a partial known epitope. The minimum number of predicted residues is 8. According to reports, the predictive accuracy is about 75% (Kolaskar A S, Tongaonkar P C reported method (FEBS Lett., 276: 172-174, 1990)).

(b) Biological Activity

In the past, it is usually to extend the protein stability in vitro through fusion protein expression protocol at the expense of protein biological activity. As the carrier proteins such as albumin, Fc fragments, often has large molecular weight and great steric hindrance. The interaction between the bioactive protein and its effective ligand would be hindered after fusion. Such as Huang Y S, etc. (Huang Y S et al., Eur J Pharm Biopharm., 67:301-308, 2007) reports that the HSA/IFNα fusion protein, retained only the original activity of IFNα1.7% (molar ratio calculation). However, the recombinant gelatin-like fusion protein in the present invention, surprisingly retained a high biological activity. As described in Example 3, The invitro activity of the rGLK1164/G-CSF fusion protein was 146% of the G-CSF. In addition, rGLK116$_4$/IFNα protein of the present invention in vitro activity seven times higher than the existing "albumin-IFN" fusion protein Better activity in vitro means the smaller clinical doses, which results in improvements of cost and therapeutic effect. Recombinant gelatin-like fusion protein was able to retain more in vitro activity, but the mechanism has not been studied. This may attribute to the loose structure in the physiological state without the formation of complex structure, which has smaller steric hindrances.

(c) in vitro Stability

The recombinant gelatin-like fusion protein in the present invention not only improved in vivo half-life, but also improved in vitro stability of biological protein. As described in Example 3, both rhG-CSF without fusion protein and rGLK116$_4$/G-CSF fusion protein solution was incubated in (d) Immunogenicity For carrier protein which used to extend the half-life of fusion proteins, must has no immunogenicity. Otherwise, produced antibodies against the carrier protein which form antibodies—immune complex fusion protein accelerate the removal of fusion protein in the body, and bring other adverse reactions. Gelatin has been widely used in preparation of materials, which has proved to be immunogenic, Example 4 has proved both recombinants gelatin-like itself, or gelatin fusion protein will not induce the body to produce antibodies. As the gelatin has no species differences in the sequence itself, and compared with the programs of the previous fusion protein which shows more efficacy and safety in a variety of animal models in the evaluation phase.

(e) in vivo Biological Activity and Half-Life

Recombinant gelatin-like fusion protein prepared according to the present invention improved in vivo half-life significantly. Embodiment 5 compares the in vivo pharmacokinetics and pharmacodynamics of rhG-CSF, rHSA/G-CSF and rGLK116$_4$/G-CSF three proteins in SD rats. Given a single subcutaneous doses of rGLK116$_4$/G-CSF, a significant increase in white blood cells to promote the effect, and its in vivo half-life far more than rhG-CSF, and rHSA/G-CSF is basically the same. Embodiment 10 also shows that in vivo half-life of Exendin-4 was significantly increased after fusion with collagen in rhesus monkeys.

Usage of the Recombinant Fusion Protein with Gelatin-Like Units

As part of the fusion protein prepared according to the invention, the gelatin itself does not have biological or pharmacological activity, while the non-collagenous part of the recombinant gelatin-like proteins determined the clinical use, that means that biological function is determined by R in the fusion protein {recombinant gelatin-like GLK}p-R-{GLK}q, GLK part simply change its stability in vitro and in vivo clearance rate. Usage and dose of recombinant gelatin-like fusion protein are determined by the nature of R of Bioactive proteins/peptides. Such as blood factors EPO, G-CSF, IL-11, M-CSF which were used for proliferation of red blood cells, neutrophils, platelets and stem cell respectively, EPO/GLK, GLK/G-CSF, GLK/GM-CSF, GLK/M-CSF prepared by fusion with the GLK also has these effects. These are obvious for those skilled in the art.

Pharmaceutical Composition

Although the gelatin-like protein has good stability, in order to facilitate the storage, transport and clinical applications, the present invention includes the pharmaceutical composition of recombinant gelatin-like fusion protein and the pharmaceutically acceptable carrier. The pharmaceutical compositions can also contain conventional additives, such as diluents, protectant, preservative compositions obtained for medicinal treatment, prevention, mitigation or diagnosis of the body, especially the body's disease or symptoms. In order to improve the medicinal effect, fusion protein of this invention can also be used together with other drugs to achieve better therapeutic effect.

The main advantages of the present invention include:

1. Gelatin fusion protein prepared by recombinant expression, which is different from the polymers (such as PEG) modified methods, has the homogenous structure and simple method of preparation and can be degraded by the body, thereby not aggregat in the body.

2. Gelatin-like proteins has the increased hydrophilicity, lower isoelectric point, little or no immunogenicity and no additional biological activity, which is different from the carrier protein (such as Fc or albumin) integration solutions, 3. GLK does not have a complex structure, and has a linear structure similar with linear polymers (such as PEG, etc.). the GLK fusion proteins have small steric hindrance. Compared with the previous fusion methods, recombinant gelatin-like fusion protein retained more biological activity.

The present invention has the advantages of both fusion proteins and polymer modification, and avoids their shortcomings, which shows a better way to improve in-vivo half-life of recombinant protein drugs.

We further clarify the invention with specific embodiments. It should be understood that these embodiments only illustrate the invention, but not to limit the scope of the present invention. Unless otherwise described, the implementation of the present invention will use the conventional technology of molecular biology, microbiology, recombinant DNA and immunology, which are known to the skilled technicians. These technologies have the complete description in the literature: for example, "Molecular Cloning A Laboratory Manual," third edition (Sambrook J, Russell D W, Molecular cloning: A laboratory manual. 3rd edition, New York: Cold Spring Harkbor Laboratory Press, 2001); "protein Purification: Principles and practice," 3rd edition (Scopes R K, Protein Purification: Principles and Practice, 3rd edition, New York: Springer-Verlag, 1994), or, in accordance with instructions provided by the manufacturer of reagents 's. the operation of *Pichia pastors*, if not specifically, follow the instructions of Invitrogen Corporation, *Pichia* Expression Kit and *Pichia* Fermentation Process Guidelines. In addition, all of the following sequence, If no special explanations, the underlined parts are the restriction enzyme recognition sites, the italics parts are signal peptide sequences.

Example 1

Expression and Purification of the rGLK116$_4$ Protein

1. Cloning of the GLK116$_4$ Gene

The GLK1164 gene comprises tetrameric monomers (SEQ ID NO: 1), and the monomer named as GLK116$_1$ encoding 116 amino acids (SEQ ID NO: 2) was synthesized by Invitrogen Technology Co., Ltd. in the present invention. Synthesis process involved the insertion of a partial yeast α-factor prepro secretory signal followed by the DraIII site to the 5'-end (the first 24 bases of SEQ ID NO: 1, with XhoI site) and the Van9II and EcoRI sites at the 3'-end into the vector pMD18-T (TaKaRa) to form the plasmid pGLK116$_1$-T.

In order to obtain dimeric gene GLK116$_2$, the plasmid pGLK116$_1$-T was double digested with Van91I/DraIII, and the resulting 330 bp fragment (GLK116$_1$) was isolated from an 1% agarose gel, purified with Gel purification Kit(Shanghai Huashun Bio-engineering Co., Ltd.) and stored at −20° C. In a separate reaction the plasmid was linearized with Van91I, purified the same as the fragment, and dephosphorylated by Alkaline Phosphatase(Takara). The Van91I/DraIII fragment was then inserted into this linearized vector using the molar ratio of 1:10 by T4 DNA ligatase and the resulting products was transformed into *E.coli* DH5α competent cells.

The transformants was picked into the LB liquid medium containing ampicillin and cultured. The plasmids were then extracted by the conventional method and identified by digestion with XhoI/EcoRI. The positive clone was confirmed by DNA sequencing.

As described above, the GLK116$_2$ was inserted into the pGLK116$_2$-T to form the tetrameric gene GLK116$_4$ (SEQ ID NO: 3)

2. Construction of the Expression Plasmid pPIC-GLK116$_4$

Figure 2:
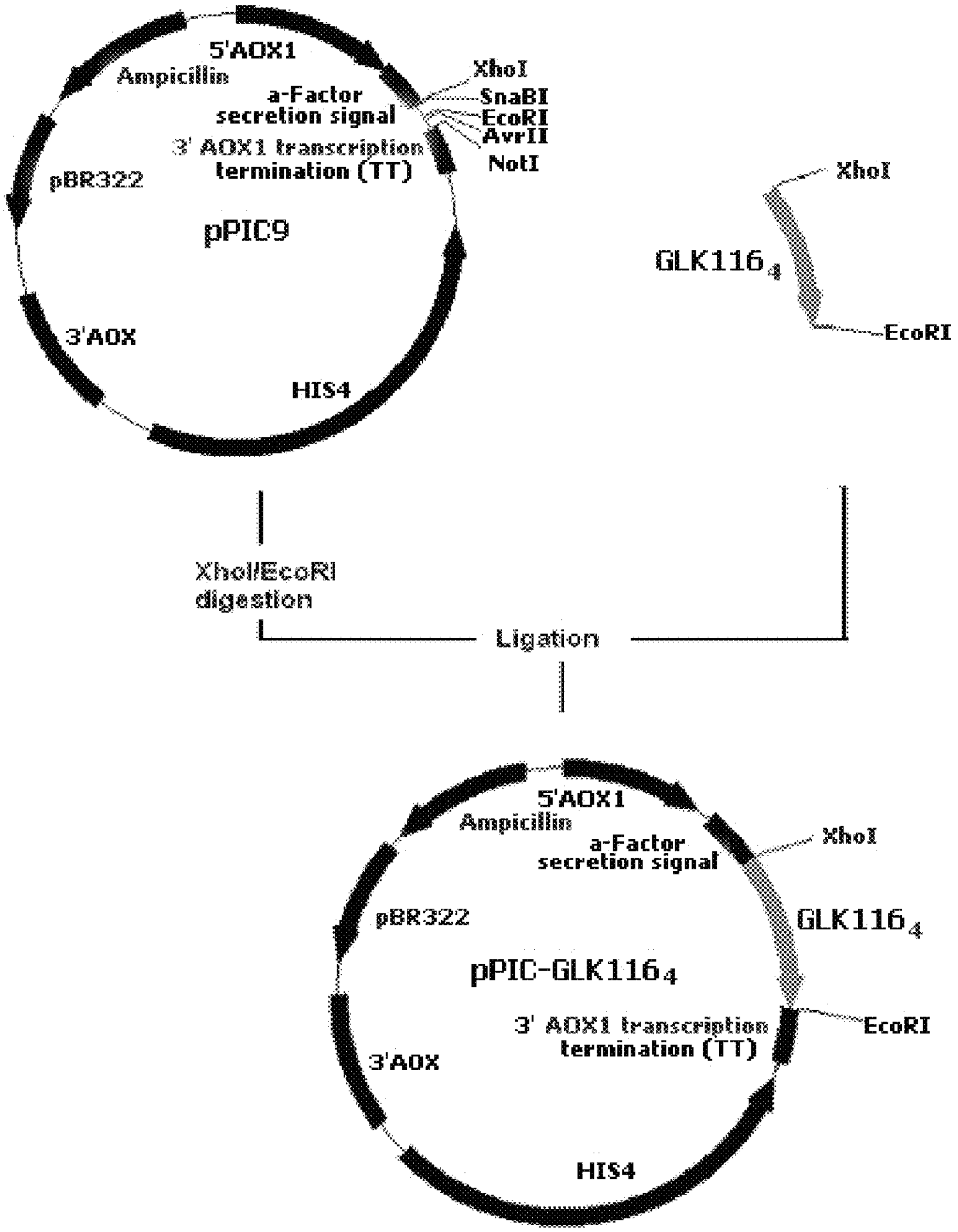
FIG. 2 shows the flow diagram showing the construction of the expression plasmid of pPIC-GLK116$_4$.

See FIG. 2. The expression plasmid pPIC9(Invitrogen) was double digested with XhoI/EcoRI, isolated from 1% agarose gel, and purified with Gel purification Kit. The gene GLK116$_4$ was released by digesting pGLK116$_4$-T with XhoI/EcoRI, and the resulting 1200 bp fragment was purified and ligated to the digested pPIC9 with T4 DNA ligatase, followed by transformation into *E.coli* DH5α and identification of the transformants.

3. Construction of *P. pastoris* Strains Expressing the Protein rGLK116$_4$

Plasmid pPIC-GLK116$_4$ was linearized and transformed into the expression strain *Pichia pastor* GS115(His$^-$) by electroporation. Cells were spread on the screening plates and cultured at 30° C. for 3 days to yield single colonies.

4. Screening for High Expression of the Protein rGLK116$_4$

The transformants were grown in the 10 ml BMGY medium at 30° C. in a shaking incubator (250 rpm) for 24 hours, decant the supernatant after standing overnight, and resuspend cell pellet in 10 ml BMMY medium at 30° C. in a shaking incubator(250 rpm) with methanol being added to 1% every day for expression. The high expression transformant was selected to be the expression stain.

5. Fermentation and Purification of the Protein rGLK116$_4$

The strain obtained in step4 was grown in YPD liquid medium at 30° C. in a shaking incubator (250 rpm) until the value of $OD_{600}$ of the culture reached 20 which used as the seed culture, followed by transfer to B. BRAUN BIOSTAT C-10 fermenter. The fermentation medium was prepared according to Invitrogen's *Pichia* Fermentation Process Guidelines. Fermentation conditions were listed as follows. The seed culture was 10% of the initial fermentation medium. The temperature was set at 30° C. The pH was adjusted to pH 5.0. A methanol feed was initiated to induce the protein expression after the glycerol was completely consumed. The induction period last for 72 h at 25° C.

Cells were removed by centrifugation and 1 L supernatant was added ice-cold acetone to a final concentration of 40% at 4° C., stirred for 30 minutes and centrifuged to remove the precipitate. The supernatant was again added ice-cold acetone to a final concentration of 80% at 4° C., stirred for 30 minutes and centrifuged to collect precipitate. The recombinant gelatin-like fusion protein precipitate was resuspended in 100 ml purified water and dialyzed into 20 mM PB, pH7.0 at 4° C. overnight.

The dialyzed product was loaded onto a Q Sepharose FF column(GE Healthcare, XK26/20, 50 ml of column volume) which was pre-equilibrated with buffer A (20 mM PB, pH7.0). The Q column was washed with 2 column volumes of buffer A to remove the unbound proteins and the target protein was eluted by a linear gradient from 0 to 100% buffer B(20 mM PB, 0.5M NaCl, pH7.0) over 10 column volumes.

The eluted protein $rGLK116_4$ was concentrated to a final protein concentration of about 10 mg/ml by ultrafiltration (Millipore, MWCO 10 KD), desalted by Sephadex G25 column(GE Healthcare, XK26/20; 50 ml of column volume) with 10 mM PB buffer, pH7.0, and freeze-dried.

The protein concentration was determined by Bradford method. The rGLK1164 could be obtained 40 mg per liter fermentation broth, the purification yield was about 20% and the purity was 98% by RP-HPLC analysis.

Example 2

Expression, Purification and Identification of the Fusion Protein $rGLK116_4$/G-CSF 1. Synthesis of the Gene hG-CSF The gene hG-CSF (SEQ ID NO: 4) was synthesized by shanghai Zeheng Biotechnology Co., Ltd., with DraIII site at the 5 'end and EcoRI site at 3' end, and cloned into pMD18-T vector to yield plasmid pG-CSF-T.

2. Construction of Expression Plasmid pPIC-$GLK116_4$/G-CSF

Figure 3:
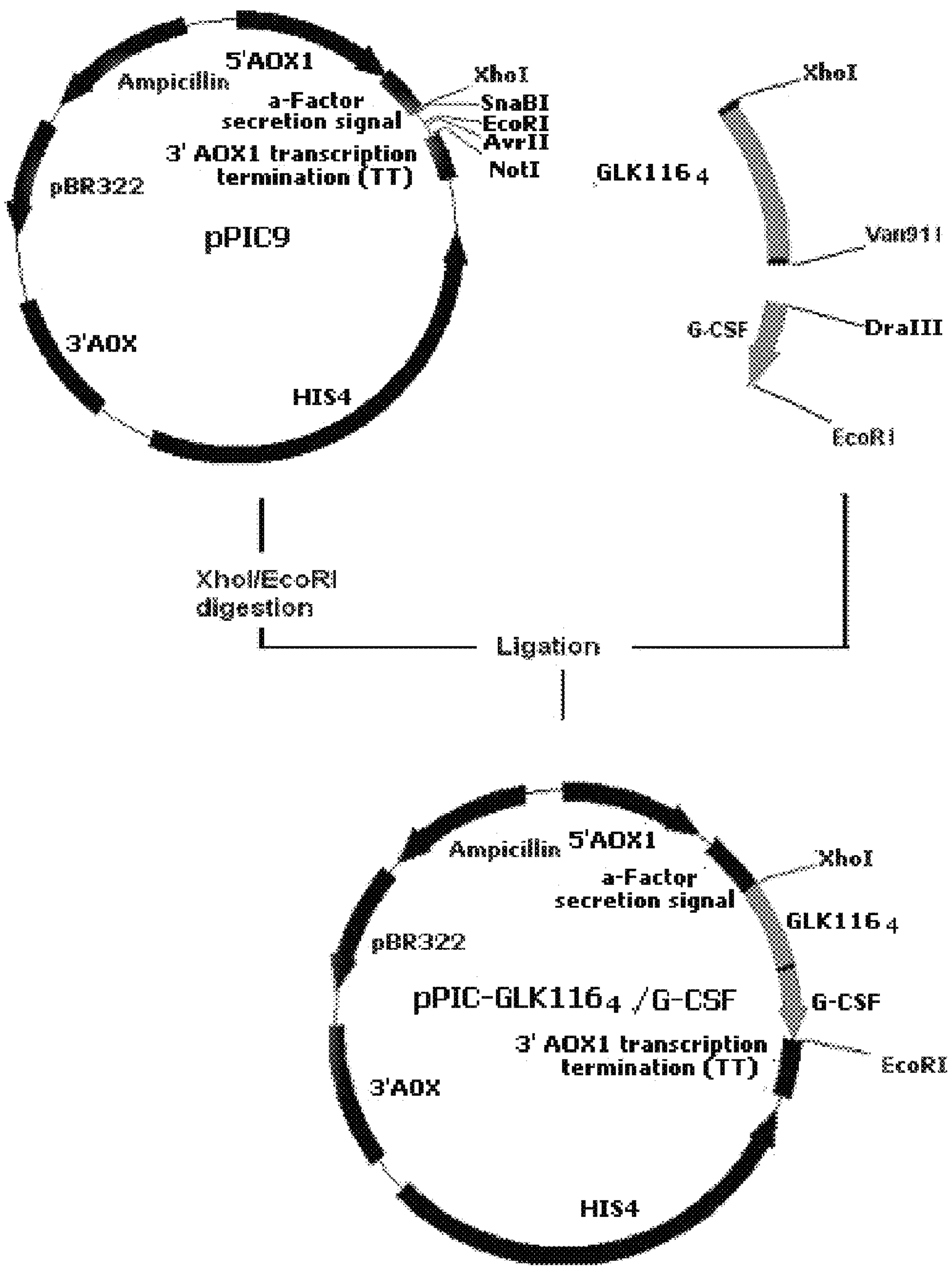
FIG. 3 shows the flow diagram showing the construction of the expression plasmid of pPIC-GLK116$_4$/G-CSF.

The process of construction was the same as Example 1 in principle and shown in FIG. 3. The DNA sequence encoding $GLK116_4$/G-CSF and mature amino acid sequence of the fusion protein $GLK116_4$/G-CSF were referred to SEQ ID NO: 5 and SEQ ID NO: 6 respectively.

3. Construction of *P. pastoris* Strains Expressing the Fusion Protein $rGLK116_4$/G-CSF Plasmid pPIC-GLK1164/G-CSF was transformed into the methylotrophic yeast *Pichia pastor* GS115 (His-). The plasmid linearization, GS115 competent cell preparation and the electroporation method were referred to Example 1.

4. Expression of $rGLK116_4$/ G-CSF Fusion Protein

A single colony from the transformation plate was inoculated 10 ml BMGY and the process of expression was referred to Example 1.

5. Purification of $rGLK116_4$/G-CSF Fusion Protein

Refer to Example 1 for fermentation. Fermentation broth was clarified by centrifugation and 1 L of the supernatant filtered through 0.45 μm filter after centrifugation was adjusted to pH 3.0 and diluted with deionized water to a final conductivity <5 ms/cm. The pretreated supernatant was loaded onto a SP Sepharose FF column (GE Healthcare, XK26/20, column volume 50 ml) which was pre-equilibrated with buffer A (20 mM NaAc, pH3.0). The SP column was washed with 2 column volumes of buffer A to remove the unbound protein and then washed with buffer B (20 mM NaAc, 0.3M NaCl, pH3.0) to collect the elution peak.

Eluted $rGLK116_4$/G-CSF was desalted by Sephadex G25 column (GE Healthcare, XK50/30; column volume 600 ml) with 20 mM Tris, pH8.5 and then loaded onto a Q Sepharose FF column (GE Healthcare, XK16/20, column volume 20 ml) which was pre-equilibrated with buffer C (20 mM Tris, pH8.5). The Q column was washed with 2 column volumes of buffer C to elute the unbound protein and then GLK1164/G-CSF was eluted by a linear gradient from 0 to 100% buffer D (20 mM Tris, 0.5M NaCl, pH8.5) over 10 column volumes.

Eluted $GLK116_4$/G-CSF was concentrated to a final protein concentration of 10 mg/ml by ultrafiltration (Millipore, MWCO 10 KD), desalted by Sephadex G25 column (GE Healthcare, XK26/20; column volume 50 ml) with 10 mM PB, pH7.0 and freeze-dried.

Protein concentration was determined by Bradford method. The $rGLK116_4$/G-CSF could be obtained 30 mg per liter fermentation broth and the purification yield was about 28%. The results were shown in Table 4.

Example 3

Analysis and Identification of $rGLK116_4$/G-CSF

1. SDS-PAGE

Figure 4:
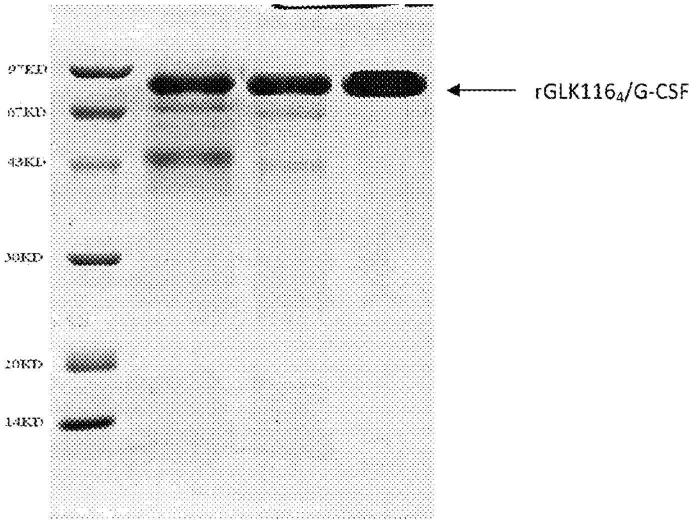
FIG. 4 shows the SDS-PAGE (8%) analysis results of purified rGLK116$_4$/G-CSF. The final purified one results a single band and its apparent molecular weight ranges between 66 KD-97 KD. From left to right: Lane 1. Low molecular weight protein marker; Lane 2. fermentation supernatant; 3. SP column elution peak; 4. Q column elution peak.

The purity of $rGLK116_4$/G-CSF was analyzed by 8% SDS-PAGE, showing a single band, the apparent molecular weight range between 66 KD-97 KD (see FIG. 4).

2. Size Exclusion Chromatography—High-performance Liquid Chromatography (SEC-HPLC)

Figure 5:
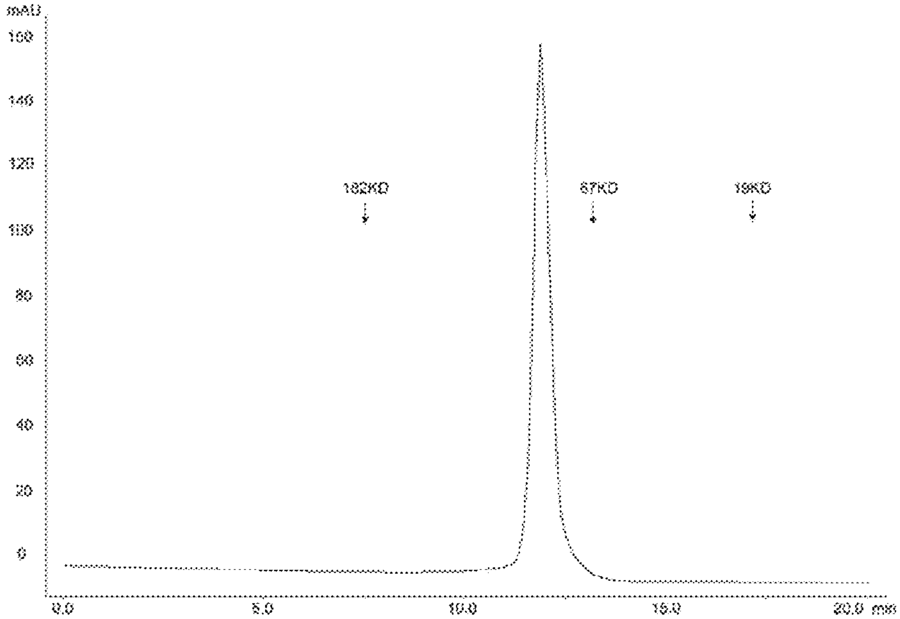
FIG. 5 shows the SEC-HPLC analysis result of purified rGLK116$_4$/G-CSF. The analysis was performed with TSK Gel G3000 Swxl column, 50 mM PB buffer(pH 7.0) including 0.25M NaCl, detection wavelength of 214 nm, and flow rate of 0.8 ml/min.

The result of SEC-HPLC on TSK Gel G3000 Swxl column with 50 mM PB, 0.25M NaCl, pH7.0 was shown in FIG. 5, showing the apparent molecular weight of about 154 KD (apparent molecular weight: Theory MW=2.8).

3. Reversed-Phase Chromatography—High-performance Liquid Chromatography (RP-HPLC)

Figure 6:
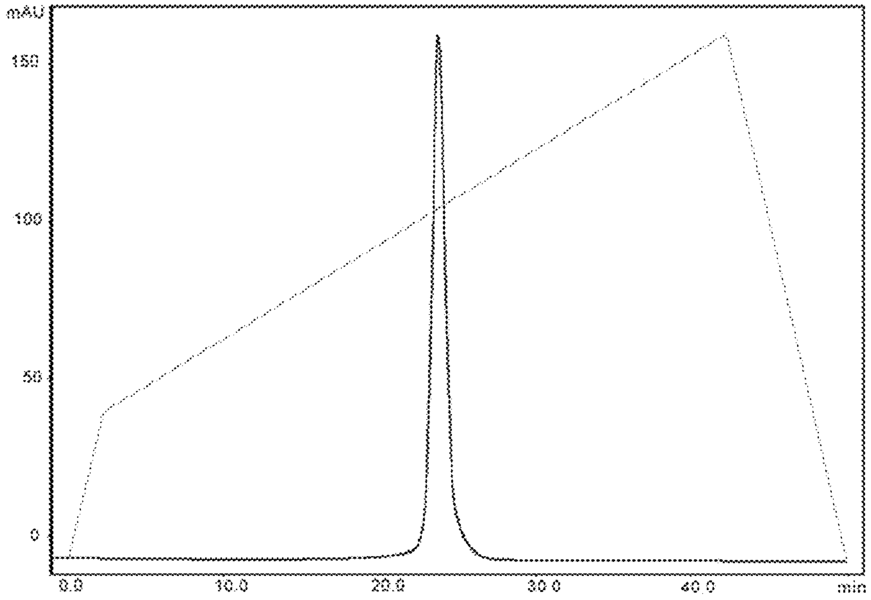
FIG. 6 shows the RP-HPLC analysis result of purified rGLK116$_4$/G-CSF. The analysis was performed with VYDAC protein C4 column, mobile phase A: 0.1% TFA aqueous solution, mobile phase B: 90% acetonitrile aqueous solution including 0.1% TFA, detection wavelength was 214 nm, and flow rate was 0.8 ml/min.

RP-HPLC was applied on VYDAC protein C4 TP5415 column with the mobile phase A of aqueous solution containing 0.1% TFA and mobile phase B of 90% acetonitrile solution containing 0.1%TFA. The result was shown in FIG. 6.

4. Western Blot Analysis

Figure 7:
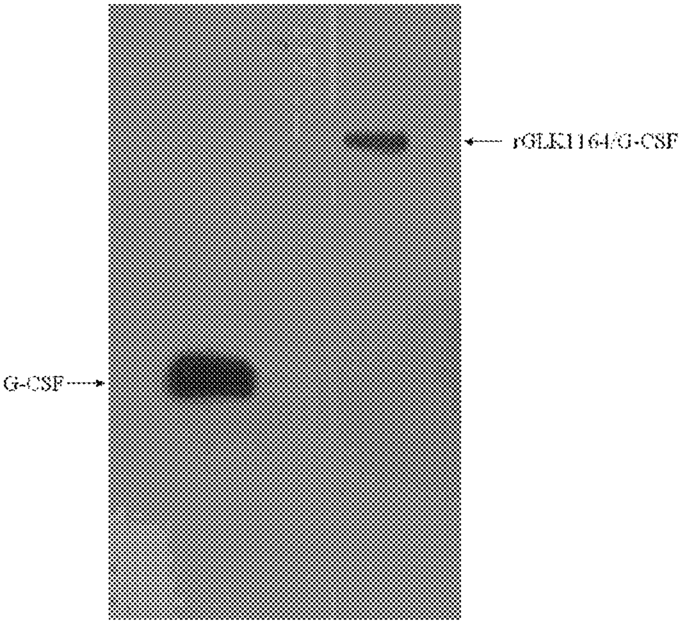
FIG. 7 shows the Western blot analysis result of rGLK116$_4$/G-CSF, with murine anti-G-CSF polyclonal antibody as the primary antibody.

Western blot analysis of $GLK116_4$1G-CSF was carried out by using the anti-mouse polyclonal antibody (ANTIGENIX) as an anti-G-CSF antibody and G-CSF as a positive control. The result was showing a positive band around 90 KD (FIG. 7).

5. In vitro Bioactivity Assay

Figure 8:
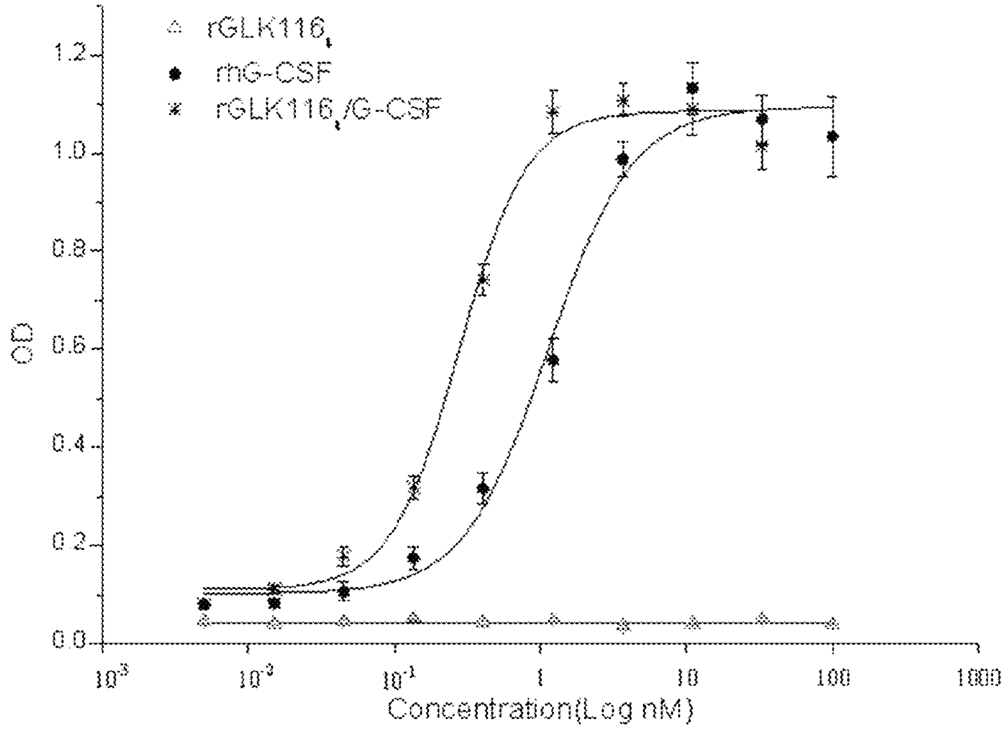
FIG. 8 shows the bioactivities of rGLK116$_4$/G-CSF in vitro analyzed by the rhG-CSF dependent strain NSF60.

In vitro bioactivity of the rGLK1164/G-CSF fusion protein was measured in G-CSF-dependent cell line NFS60 by MTT assay (Chinese Pharmacopoeia, 2005 edition, three sections). One of the representative assay results was shown in FIG. 8.

The activity of rGLK1164/G-CSF was about $3.3\times10^7$ IU/mg, equivalent to about 146% of the biological activity of G-CSF calculated on a molar basis.

6. In vitro Stability

Figure 9:
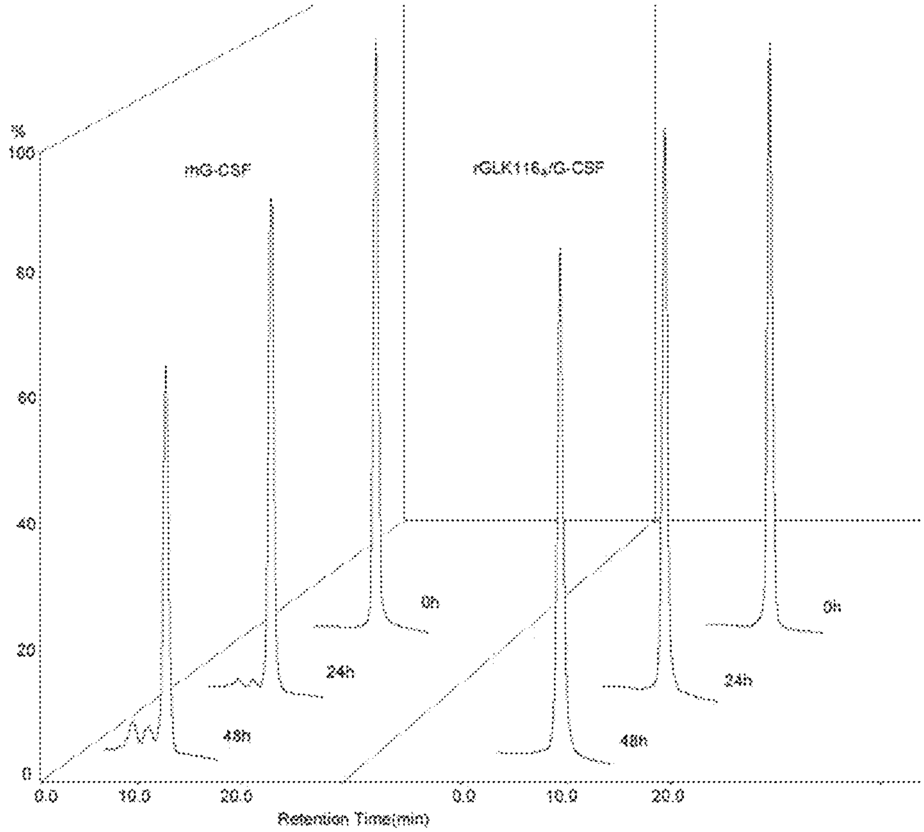
FIG. 9 shows the result of the in vitro stability studies of rGLK116$_4$/G-CSF and rhG-CSF through SEC-HPLC analysis.

Reference rhG-CSF and $rGLK116_4$/G-CSF were dissolved in 20 mM PB, pH6.0 to the protein concentration of 1 mg/ml. samples were sterile filtered and distributed to penicillin bottles. The residual protein content and monomeric proteins were analyzed by SEC-HPLC afte shock 48 hours at 40° C. The results showed that a large number of polymeric aggregates were formed and the total protein content was also decreased significantly in rhG-CSF, while $rGLK116_4$/G-CSF fusion protein was changed little in these indicators (see Table 2 and FIG. 9). This indicated that in vitro stability of the bioactive protein was significantly improved after fusion with the GLK.

TABLE 2

SEC-HPLC analysis results of different structures G-CSF accelerated test

| | Purity (%) (SEC-HPLC analysis) | | | protein content after incubation (%) | | |
|---|---|---|---|---|---|---|
| | 0 h | 24 h | 48 h | 0 h | 24 h | 48 h |
| rhG-CSF | 99.8 | 94.3 | 85.2 | 100 | 91.2 | 68.9 |
| rGLK116$_4$/G-CSF | 99.5 | 98.7 | 97.5 | 100 | 97.8 | 96.7 |

Example 4

The Immunogenicity Study of rGLK116$_4$ and rGLK116$_4$/G-CSF in Mice

Animal Immunization

Balc/C mice (n=12) with a average weight of about 25 g were evenly divided into 4 groups. 2.5 nmol rGLK116$_4$, 2.5 nmol rGLK116$_4$/G-CSF, and the same volume of saline were administered to a corresponding group respectively by subcutaneous injection once a week. Serum samples were collected in week 4 and week 9(a week after the eighth immunization) and were saved separately at −70° C.

Serum Antibody Detection rGLK116$_4$ or G-CSF was diluted with 0.2M carbonate buffer (pH9.6) to 1 μg/ml. Each well of the ELISA microplate was filled with 100 μl dilution and coated overnight at 4° C., and then the wells were washed with PBST for 3 times(5 minutes each time). The washed wells were sealed by 5% nonfat dry milk for 1 hour, and then washed three times with PBST (5 minutes each time). The preserved serum of each group was added to the well at a rate of 1:50,1:200,1:800, and then the microplate was incubated at 37° C. for 1 hour, and for one increased hour after the secondary antibody, HRP-conjugated goat anti-mouse antibody was added. After the microplate was shook to dry and washed by PBST, it was colored with TMB-HCL and detected under the illumination of 450 nm. Meanwhile, 200 ng/ml of rabbit anti-human G-CSF antibody was used as a positive control.

Figure 10:
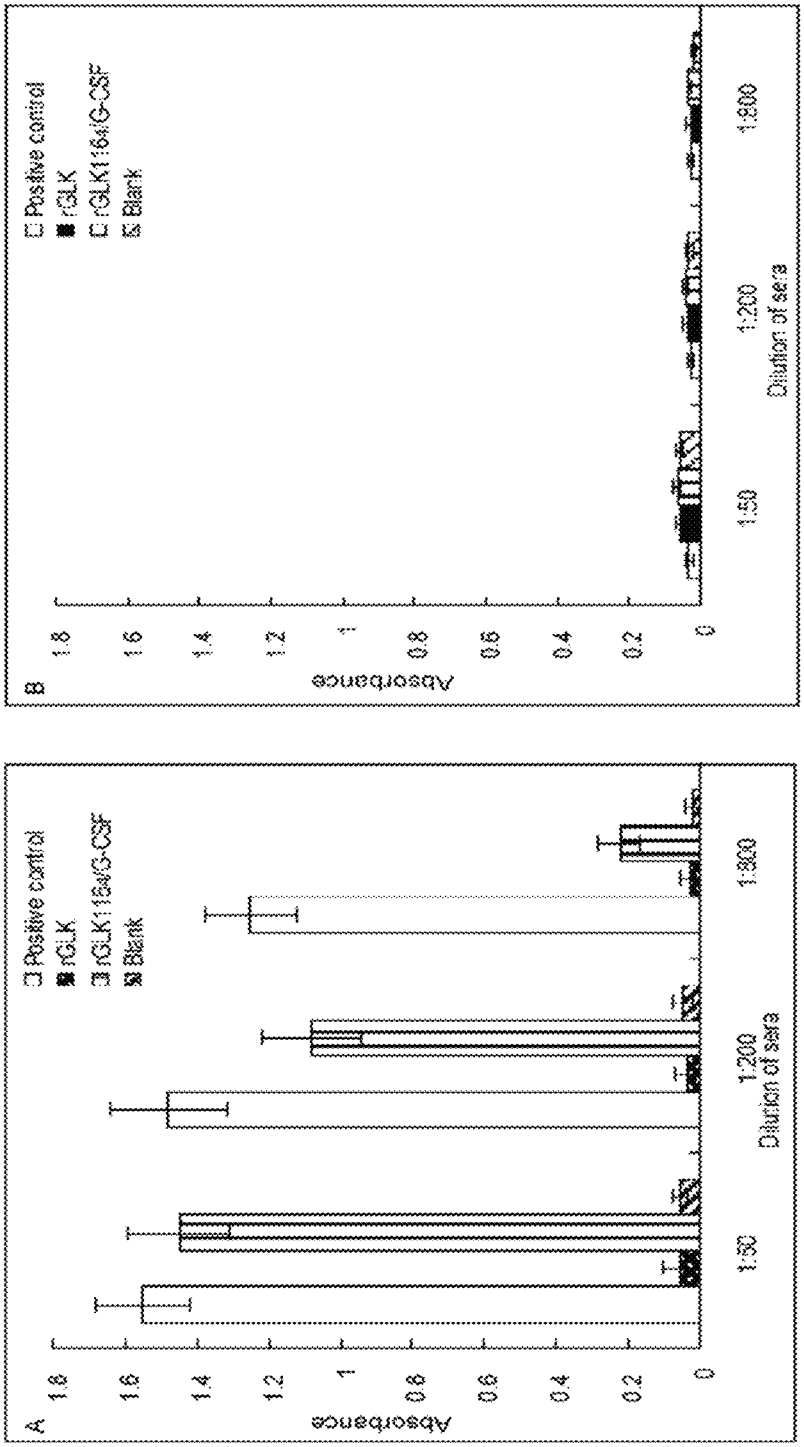
FIG. 10 shows the result of the serum antibody evaluation in mice which had been administered rGLK116$_4$ or rGLK116$_4$/G-CSF continuously for a period of time. For A, G-CSF is used for coating. For B, rGLK116$_4$ is used for coating.

The result is showed in FIG. 10. In the group coated by G-CSF, only the wells containing the serum collected from the mice administered rGLK116$_4$/G-CSF and the positive control had a higher absorption value, while in the group coated by rGLK116$_4$, absorption value of all serum samples is very low, which demonstrated that anti-G-CSF antibody is produced after the mice were administered for 4 weeks and there is no anti-rGLK116$_4$ antibody produced. This suggests that the gelatin-like units provided in the present invention are non-immunogenic.

Example 5

The Pharmacodynamic Study and Pharmacokinetic Study of rGLK116$_4$/G-CSF

The pharmacokinetic parameters and pharmacodynamic properties of rhG-CSF (Filgrastim, Amgen, USA), rHSA/G-CSF (prepared according to U.S. Pat. No. 5,876,969), rGLK116$_4$/G-CSF and rGLK116$_4$ in SD rats were compared.

Adult SPF SD rats (approximately 300-350 g) from the Center of Experimental Animals of Chinese Academy of Sciences in Shanghai were divided into 8 groups and administered according to Table 3. Blood samples were collected from the caudal veins of rats. The number of white blood cells were counted, and serum was saved at −20° C. after separated by centrifugation (3000rpm for 5 minutes).

Determination of Pharmacokinetics

The plasma concentration detection of rhG-CSF, rGLK116$_4$/G-CSF and rHSA/G-CSF was carried out using ELISA (for the specific operations, refer to the operating manual of Human G-CSF DuoSet kit Human G-CSF ELISA Construction Kit (ANTIGENIX)). The MicroCal Origin software was used to draw standard curve according to four-parameter logistic fitting method, and calculate related statistical parameters by regression analysis. The 3P87 software was used to calculate the PK parameters.

TABLE3

The schedule of grouping, administration, and sampling in the PK measurements

| Group | Number of Animals | Dose Level (mg/kg) | Route | Time of Administration | Time of sampling (hour) |
|---|---|---|---|---|---|
| rGLK116$_4$/G-CSF | 3 | 3 | Sc | D1 | 0, 2, 6, 12, 24, 48, 72, 96 |
| rGLK116$_4$/G-CSF | 3 | 1 | Sc | D1 | 0, 2, 6, 12, 24, 48, 72, 96 |
| rGLK116$_4$/G-CSF | 3 | 0.3 | Sc | D1 | 0, 2, 6, 12, 24, 48, 72, 96 |
| rGLK116$_4$/G-CSF | 3 | 1 | Iv | D1 | 0, 0.5, 4, 12, 24, 48, 72 |
| rHSA/G-CSF | 3 | 1 | Sc | D1 | 0, 2, 6, 12, 24, 48, 72, 96 |
| rHSA/G-CSF | 3 | 1 | Iv | D1 | 0, 0.5, 4, 12, 24, 48, 72 |
| rhG-CSF | 3 | 0.2 | Sc | D1 | 0, 0.5, 4, 6, 12, 24, 48 |
| rGLK116$_4$ | 3 | 1 | Sc | D1 | 0, 2, 6, 12, 24, 48, 72, 96 |

Figure 11:
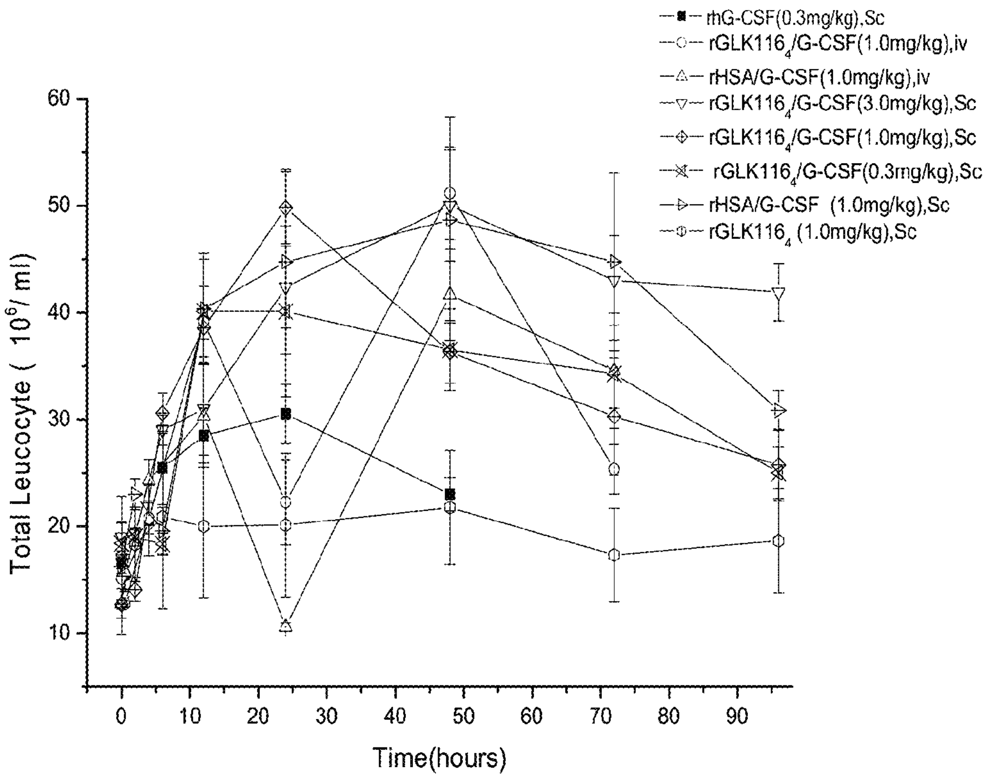
FIG. 11 shows the result of pharmacodynamics studies of rGLK116$_4$/G-CSF, rhG-CSF, rHSA/G-CSF and rGLK116$_4$ in normal adult SD rats.

The result of pharmacodynamic properties is showed in FIG. 11. The number of white blood cells increased significantly 48 hours after an injection of rHSA/G-CSF or rGLK116$_4$/G-CSF, compared to a single injection of rHSA/G-CSF, and the extent and duration of the increase was higher and longer. The extent and duration of the increase of the number of white blood cells grew with the dose of rGLK116$_4$/G-CSF administered. There is no significant difference between the extent and duration of the increase of the number of white blood cells after an injection of rGLK116$_4$/G-CSF and rHSA/G-CSF in the same dosage.

Figure 12:
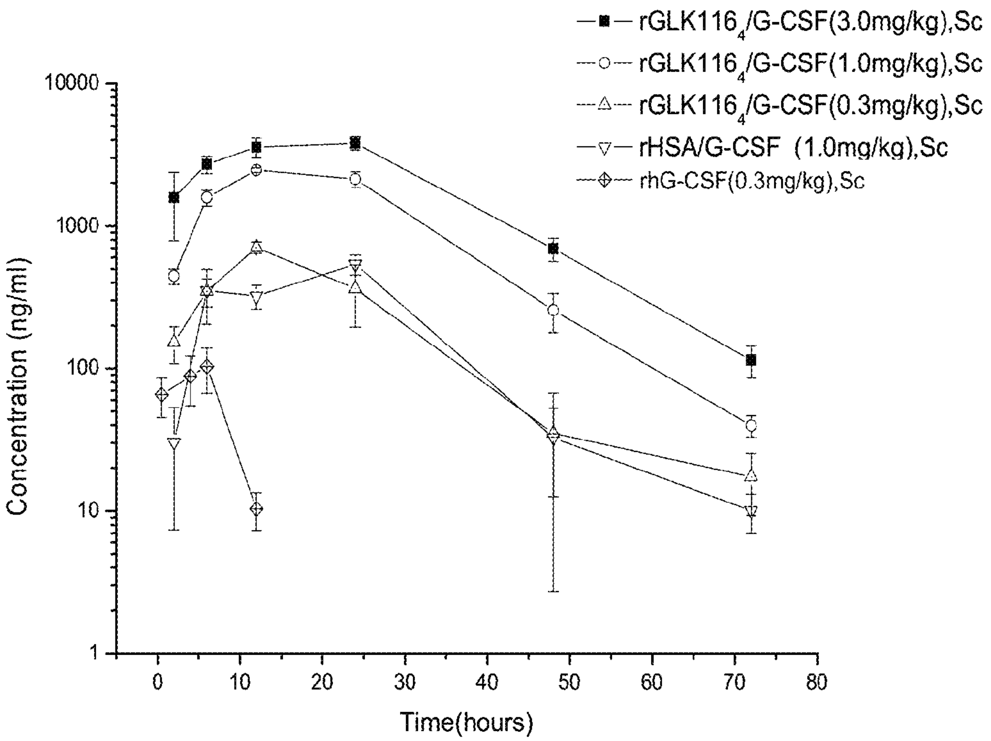
FIG. 12 shows pharmacokinetics studies of different dosage of rGLK116$_4$/G-CSF, rhG-CSF, and rHSA/G-CSF in normal adult SD rats.

The result of Pharmacokinetic study is showed in FIG. 12. According to the blood concentration—time curve, rhG-CSF is degraded rapidly after subcutaneous injection and it couldn't be detected 24 hours later, while rGLK116$_4$/G-CSF and rHSA/G-CSF could still be detected at 72 hours. The terminal half-life of rGLK116$_4$/G-CSF administered subcutaneously in rats is 10 hours, which is slightly longer than that of rHSA/G-CSF.

Example 6

A Comparison of the Properties of GLK/G-CSFs with Different Structures

GLK/G-CSFs with different structures were prepared in a similar way, and their activity, half-life in SD rats and other relevant parameters were compared.

TABLE 4

| the properties of GLK/G-CSFs with different structures | | | | |
|---|---|---|---|---|
| | Molecular weight (KD) | Bioactivity (IU/mg) | Relative activity (in molar basis)(%) | Half-life (hour) |
| G-CSF | 18.7 | $0.7 \times 10^8$ | 100 | 1.7 |
| $rGLK116_4$/G-CSF | 59.3 | $0.33 \times 10^8$ | 146 | >7 |
| $rGLK116_3$/G-CSF | 49.2 | $0.47 \times 10^8$ | 173 | >6 |
| $rGLK116_2$/G-CSF/$GLK116_2$ | 59.8 | $0.34 \times 10^8$ | 151 | >8 |
| rG-CSF/$GLK116_3$/G-CSF | 67.9 | $0.55 \times 10^8$ | 281 | >6 |
| $rGLK_{420}$/G-CSF | 57.0 | $0.28 \times 10^8$ | 129 | >7 |

Wherein, $GLK_{420}$ is selected from 1150-1569 bit of the sequence derived from the human COL5A1 collagen. The complete sequences are showed as SEQ ID NO: 7, SEQ ID NO: 8, and the DNA sequence and amino acid sequence of $GLK_{420}$/G-CSF is showed as SEQ ID NO: 9, SEQ ID NO: 10.

Example 7

Expression and Purification of $rGLK116_4$/IFNα

1. Gene Synthesis of Interferon α 2b (IFNα)

Gene of IFNα was synthesized by the Heyzer Bio Co., Ltd. (sequence see SEQ ID NO: 11), of which the 5 'end is a Dra III recognition site and the 3' end is a EcoRI recognition site. And then, it was cloned and inserted into pMD18-T vector to construct a plasmid pIFNα-T.

2. Construction of the Expression Plasmid of pPIC-$GLK116_4$/IFNα

Figure 13:
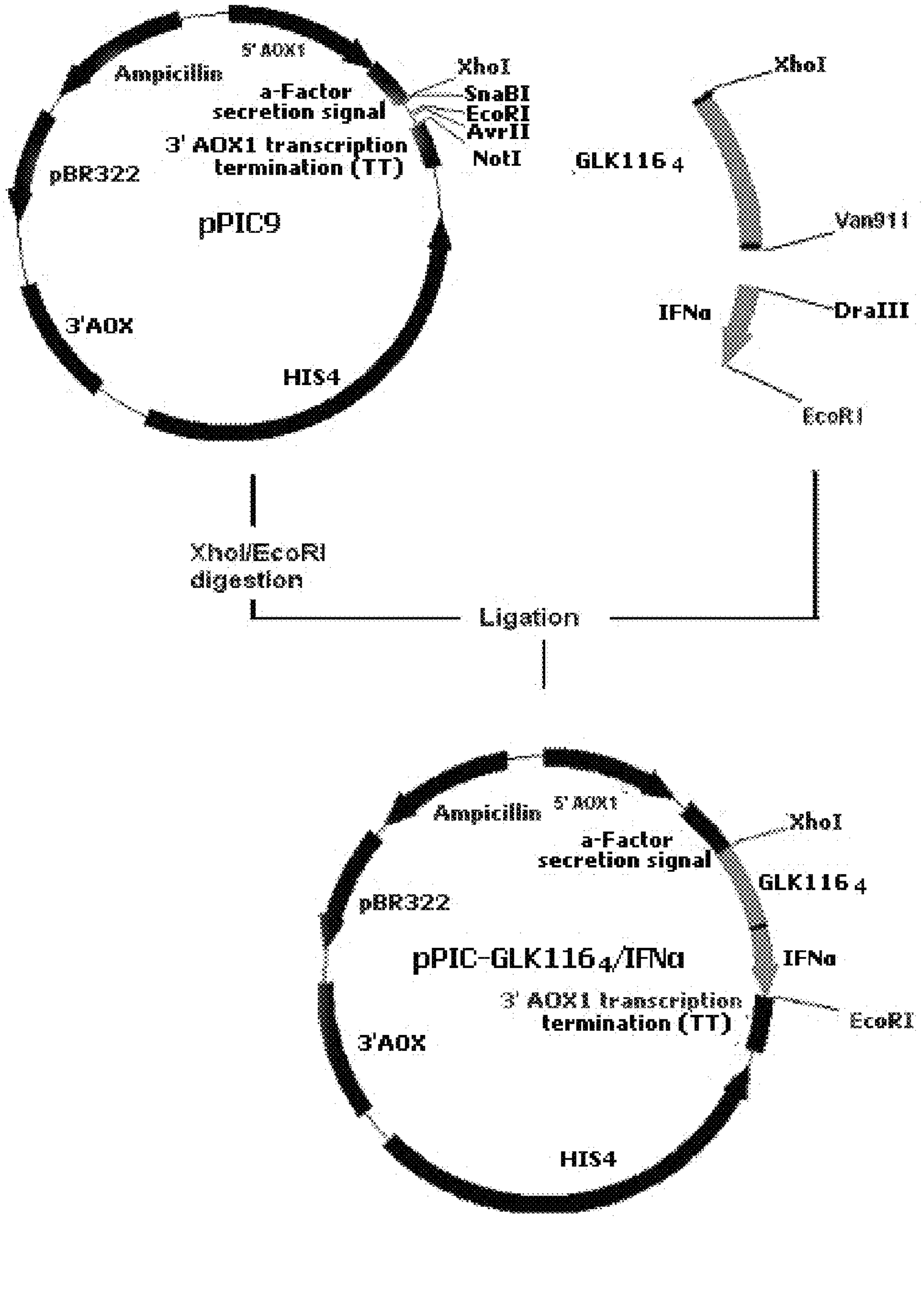
FIG. 13 shows the flow chart showing the construction of the expression plasmid of pPIC-GLK116$_4$/IFNα.

The flow chart of construction is showed in FIG. 13. The complete DNA sequence and the mature amino acid sequence of $GLK116_4$/IFNα is showed as SEQ ID NO: 12 and SEQ ID NO: 13.

3. Construction and Screening of Engineering Yeast Expressing $rGLK116_4$/IFNα

With the method as described in Example 1.

4. Expression and Purification of $rGLK116_4$/IFNα in *Pichia pastoris* GS 115

Figure 14:
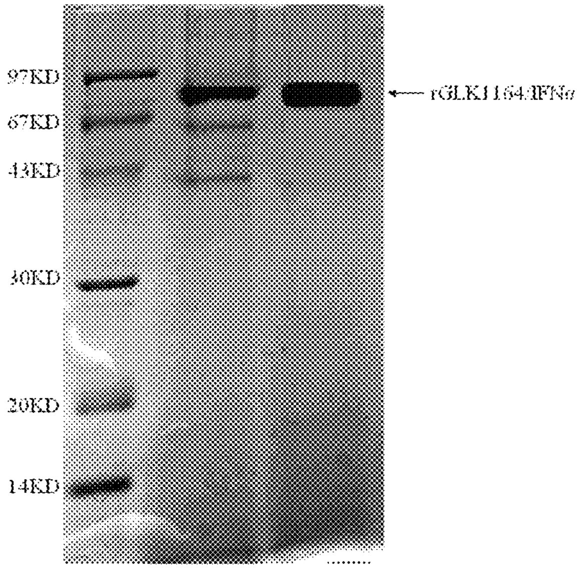
FIG. 14 shows the SDS-PAGE (8%) analysis results of purified rGLK116$_4$/IFNα. The final purified one results a single band and its apparent molecular weight ranges between 66 KD-97 KD. From left to right: Lane 1. Low molecular weight protein Marker, Lane 2. fermentation supernatant, 3. SP column elution peak, 4. Q column elution peak.

With the method as described in Example 1. The purified product was analysed by using 8% SDS-PAGE and the result is showed in FIG. 14.

5. Activity Analysis in vitro

The biological activity of $rGLK116_4$/IFNα in vitro was measured by conventional cytopathic effect (CPE) reduction assay (WISH cells) (Chinese Pharmacopoeia, 2005 edition, third section).

It was measured that the bioactivity of $rGLK116_4$/IFNα in vitro was about $2.2\times10^7$ IU/mg, which is about 11% of the bioactivity of equimolar INFα and 7 times of that of equimolar HAS/IFNα (only remain 1.4% of the bioactivity of INFα) .

6. Pharmacodynamic Evaluation

Rhesus monkeys.(n=15; including female and male; age range: 3-4; weight range: 4.2-4.8 kg), were purchased from Animal Center of Chinese Academy of Military Medicine and divided into five groups (3 in each group). Samples were diluted with PBS, wherein $rGLK116_4$/IFNα was diluted respectively to 0.36, 1.0 and 3.6 pmol/kg, IFNα (positive control) was diluted to 0.36 pmol/kg, and $rGLK116_4$ (blank control) was diluted to 0.36 pmol/kg. The diluted samples were administered to rhesus monkeys subcutaneously and the serum samples were collected at 0, 1, 2, 4, 8, 10, 14 hours after injection respectively. The activity of 2', 5'-OAS in serum was measured with 2',5'-OAS radioimmunoassay kit (Eiken Chemical Co., Tokyo, Japan).

Figure 15:
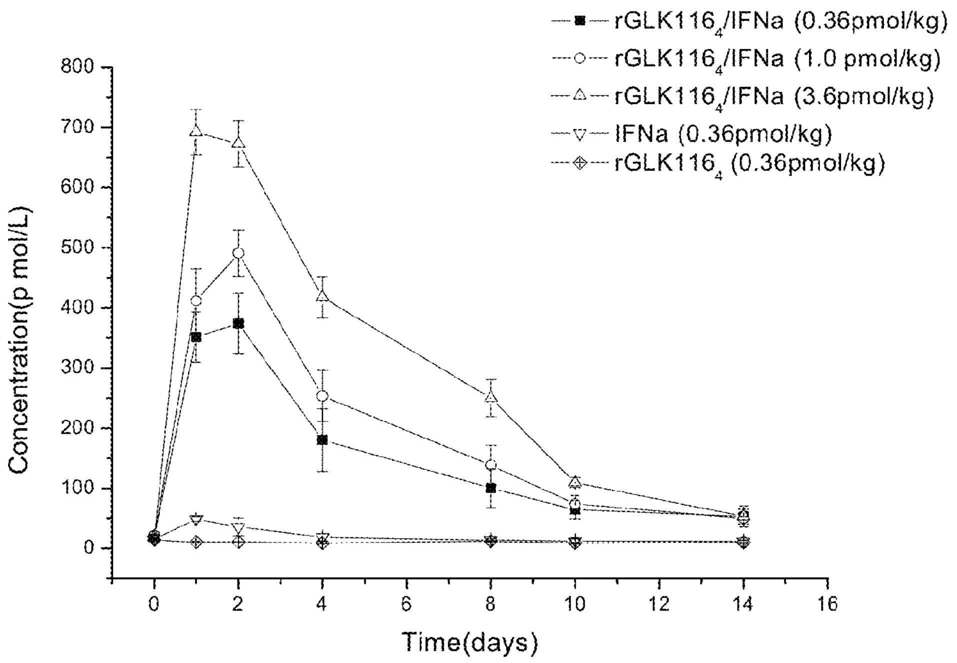
FIG. 15 shows the result of pharmacokinetic study of rGLK116$_4$/IFNα in the macaque monkey.

As showed in FIG. 15, the concentration of 2',5'-OAS of the tested serum was significantly dose-dependent. The activity of 2',5'-OAS in vivo rose to peak 2 days later after the administration. $rGLK116_4$/IFNα still could be detected in vivo 14 days later, while IFNα in vivo could hardly be detected 6 days later. And the activity of 2',5'-OAS of the serum of monkeys administered $rGLK116_4$/IFNα was significantly higher than that of the monkeys administered the same dose of IFNα which demonstrated that the half-life of fusion protein was significantly prolonged.

The structure characteristics and half-life in SD rats of the different GLK/IFNαs, which was constructed by fusion to different GLK, was compared in Table 5.

TABLE 5

| Compare of the property of IFNα that fused with different GLK | | | | | | | |
|---|---|---|---|---|---|---|---|
| | molecular weight (kd) | percent of hydrophilic amino acid residues of GLK(%) | Gravy value of GLK | isoelectric point of GLK | $s_{gly}/n$ | $s_{(pro+hyp)}/n$ | half-life (hours) |
| $GLK116_2$/IFNα | 39.8 | 64.7 | −1.789 | 5.06 | 1.04 | 0.65 | 25.6 |
| $GLK116_2$P-/IFNα | 39.4 | 64.7 | −1.618 | 5.06 | 1.04 | 0 | 17.8 |
| GLK302/IFNα | 39.5 | 33.1 | −0.532 | 5.52 | 2.02 | 0 | 14.4 |
| $GLK116_2$N-/IFNα | 40.2 | 64.7 | −1.789 | 3.93 | 1.04 | 0.65 | 31.2 |

It is similar in the length of the sequences of the four GLK as described above. However, the half-life of the resulting recombinant fusion proteins linked to them is diverse:

The Pro and Hyp in the sequence of $GLK116_2$P- are replaced by Ser compared with $GLK116_2$, which does not affect the hydrophilia much but does significantly decrease its half-life in vivo.

The basic sequence of GLK302 is a repeated sequence of "GGSGGS" and containing neither Pro nor Hyp. Compared with $GLK116_2$P-, there are more Gly residues in the sequence of GLK302 (the ratio for sum amount of Gly residues compaired to n is 2.02). Both of the molecular weight and the isoelectric point of $GLK116_2$P- and GLK302 is similar. However GLK302 is more hydrophobic (with larger GRAVY value) and has a shorter half-life in vivo, compared to $GLK116_2$P-. This suggests that, the ratio for sum amount of Gly residues compared to n should be ≤1.5,which would be better to be ≤1.15 and much better to be ≤1.05;

The Glu residues in the sequence of $GLK116_2$ are instead of Asn residues in the sequence of $GLK116_2$N—, which doesn't affect the hydrophilia much, but does significantly decrease its isoelectric point and extend its half-life in vivo.

The approaches to construct GLK116$_2$/IFNα, GLK116$_2$P-/IFNα, GLK302/IFNα and GLK1162N-/IFNα are similar with that of example 1 and example 2. The amino acid sequences (mature ones) of these four proteins are showed as SEQ ID NO : 14-17.

Example 8

Expression and Purification of rExendin-4/rGLK

The GLK104$_6$ gene is composed of six identical monomers (SEQ ID NO: 18), and the monomer was named as GLK104$_1$ encoding 104 amino acids (SEQ ID NO: 19); The GLK107$_6$ gene was composed of six identical monomers (SEQ ID NO: 20), and the monomer was named as GLK107$_1$ encoding 107 amino acids (SEQ ID NO: 21). The sequences of the two genes were both synthesized by Invitrogen Technology Co., Ltd. The process of the construction was similar to example 1: the GLK104$_2$ and GLK107$_2$ were ligated to the vector pGLK1044-T and pGLK1074-T respectively, to form the plasmid pGLK104$_6$-T and pGLK107$_4$-T containing six monomers GLK104$_1$ and GLK107$_1$.

1. Cloning of Gene Exendin-4

Exendin-4 gene was synthesized by shanghai Zeheng Biotechnology Co., Ltd., and the DNA sequence refers to SEQ ID NO: 22:

The sequence was cloned into pMD18-T vector after synthesis to form the plasmid pExendin-4-T. Exendin-4 was composed of a partial gene of yeast α-factor prepro secretory signal peptide at the 5' end (with Xho I sites) and the Dra III recognition site at the 3' end.

Figure 16:
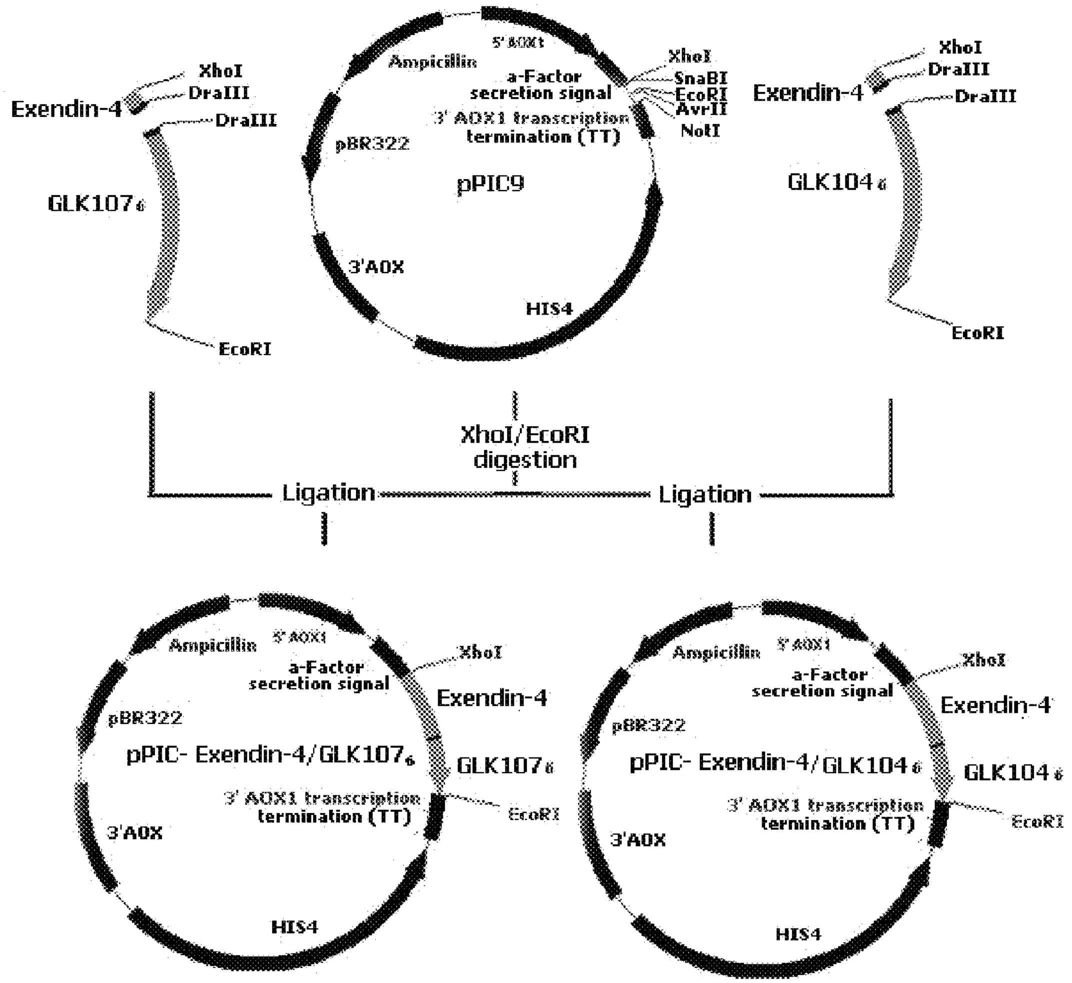
FIG. 16 shows the flow chat showing the construction of the expression plasmid of pPIC-Exendin-4/GLK104$_6$ and pPIC-Exendin-4/GLK107$_6$. Exendin-4 refers to exenatide.

2. Construction of Expression Plasmid pPIC-Exendin-4/GLK104$_6$ and pPIC-Exendin-4/GLK107$_6$ refers to FIG. 16

SEQ ID NO: 23-26 was the DNA sequences of Exendin-4/GLK1046 and Exendin-4/GLK1076, and mature amino acid sequence of the fusion protein, respectively.

3. Construction and Screening of the Engineering Yeast Expressing rExendin-4/GLK104$_6$ and rExendin-4/GLK107$_6$ Fusion Protein The process was similar to Example 1.

Figure 17:
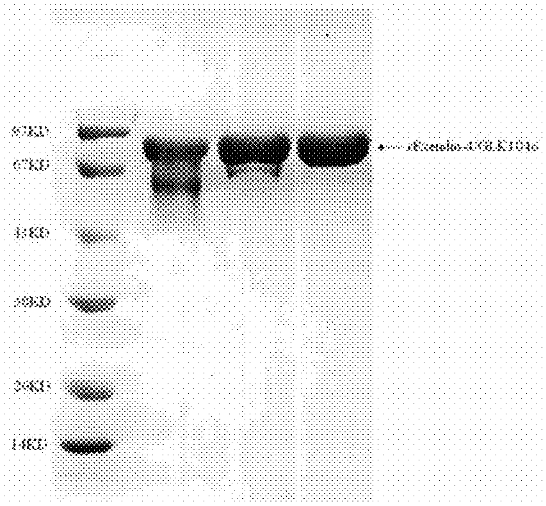
FIG. 17 shows the SDS-PAGE (8%) analysis results of purified rExendin-4/GLK104$_6$. The final purified one results a single band and its apparent molecular weight ranges between 66 KD-97 KD. From left to right: Lane 1. Low molecular weight protein Marker, Lane 2. fermentation supernatant, 3. SP column elution peak, 4. Q column elution peak.

4. Fermentation and Purification of rExendin-4/GLK104$_6$ and rExendin-4/GLK107$_6$ Fusion Proteins The method of fermentation and purification were similar to Example 1. The concentration of purified fusion proteins (rExendin-4/GLK107$_6$ and rExendin-4/GLK104$_6$) was up to 10 mg/mL by ultrafiltration (Millipore, MWCO 10 KD). Then, the fusion protein concentrates were desalted by Sephadex G25 column (GE Healthcare, XK26/20; column volume 50 ml) with 10 mM PB, pH7.0, and freeze-dried. The result of the electrophoresis analysis was shown in FIG. 17.

Example 9

Biological Activity of the rExendin-4/GLK104$_6$ and rExendin-4/GLK107$_6$ Fusion Protein BHK cells stably transfected with GLP-1R (baby hamster kidney cell) can receive the signal derived from GLP-1 and its agonist, resulting in the increasing of the intracellular cAMP levels. Thus, the release amount of cAMP can indirectly reflect the biological activity of rExendin-4 fusion protein. The culture method of BHK-GLP-1R cell refers to the method described earlier by Li Y, etc. (Li Y et al., J Biol Chem., 278:471-478,2003).

Figure 18:
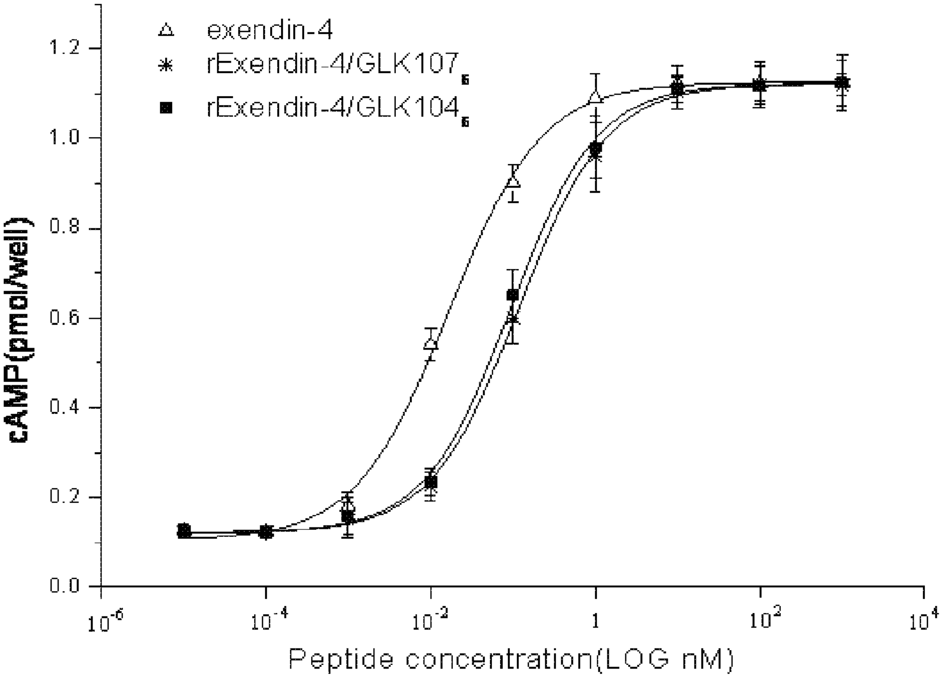
FIG. 18 shows the bioactivities of rExendin-4/GLK104$_6$ and rExendin-4/GLK107$_6$ in vitro analysed by the stable BHK cells that transfected with GLP-1R.

The results showed that rExendin-4/GLK in BHK-GLP-1R can stimulate the production of intracellular cAMP in a dose-dependent manner; and the in vitro receptor binding activity of the fusion protein is similar to standard Exendin-4 (FIG. 18; Exendin-4 $EC_{50}$=0.017 nM, rExendin-4/GLK104$_6$ $EC_{50}$=0.095 nM, rExendin-4/GLK107$_6$, $EC_{50}$=0.113 nM).

Example 10

Pharmacokinetic of rExendin-4/GLK104$_6$ and rExendin-4/GLK107$_6$

Pharmacokinetics of the fusion protein was performed in monkeys. Six monkeys, including three male and three female (ages 3-4, weight 4.2-4.8 kg), were purchased from Animal Center of Chinese Academy of Military Medicine. Animals were fed according to the routine feeding (Experimental Animal Center of Zhejiang University). 3 per group, received subcutaneous injection, samples diluted with PBS to the concentration of 4 mg/kg. Blood samples were collected at 0.5, 1, 4, 8, 12, 24, 48, 72, 96, 120, 144, 192, 240, 288, and 336 hours in a collection tubes containing EDTA. The concentration of fusion protein in the plasma was measured by ultra-sensitive Ex-4 RIA kit (Phoenix pharmaceuticals, Inc., USA). The blank plasma was used for dilution and calibration in above experiments.

Figure 19:
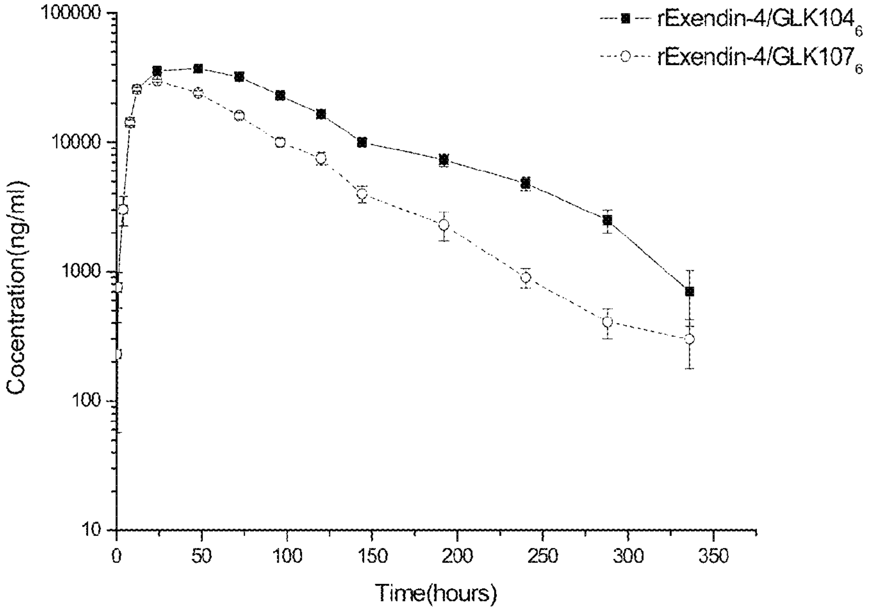
FIG. 19 shows the result of pharmacokinetic studies of rExendin-4/GLK104$_6$ and rExendin-4/GLK107$_6$ in macaque monkeys.

The results were shown in FIG. 19 and indicated that the terminal half-lives of rExendin-4/GLK1046 and rExendin-4/GLK1076 were 70.4 hours and 45.4 hours respectively in the monkeys after subcutaneous injection. rExendin-4/rGLK1046 reached the maximum concentration of 36980 ng/ml at 48 hours after subcutaneous injection. Half-life was increased by 15 times (Note: half-life of Exendin-4 is only 2.4 hours.)

Example 11

Expression and Purification of rEPO/GLK1074 Fusion Protein

1. Cloning of EPO Gene

The EPO gene was synthesized by shanghai Zeheng Biotechnology Co., Ltd. The DNA sequence refers to SEQ ID NO: 27.

The EPO gene was cloned into pMD18-T after synthesis to form the plasmid pEPO-T. The Nhe I recognition site and Kozak sequence were at 5'end of EPO and Dra III recognition site was at 3' end. The italics stands for the sequence of EPO signal peptide.

2. Cloning of GLK107$_4$ Gene

According GLK107$_4$ gene sequences, primers GLK107$_4$/P1 (SEQ ID NO: 28) with DraIII recognition site and GLK107$_4$/P2 (SEQ ID NO: 29) with NotI recognition site were synthesized. GLK107$_4$ was obtained by conventional PCR amplification using pGLK107$_4$-T as a template.

3. Construction of Expression Plasmid pCEP4-EPO/GLK107$_4$

Figure 20:
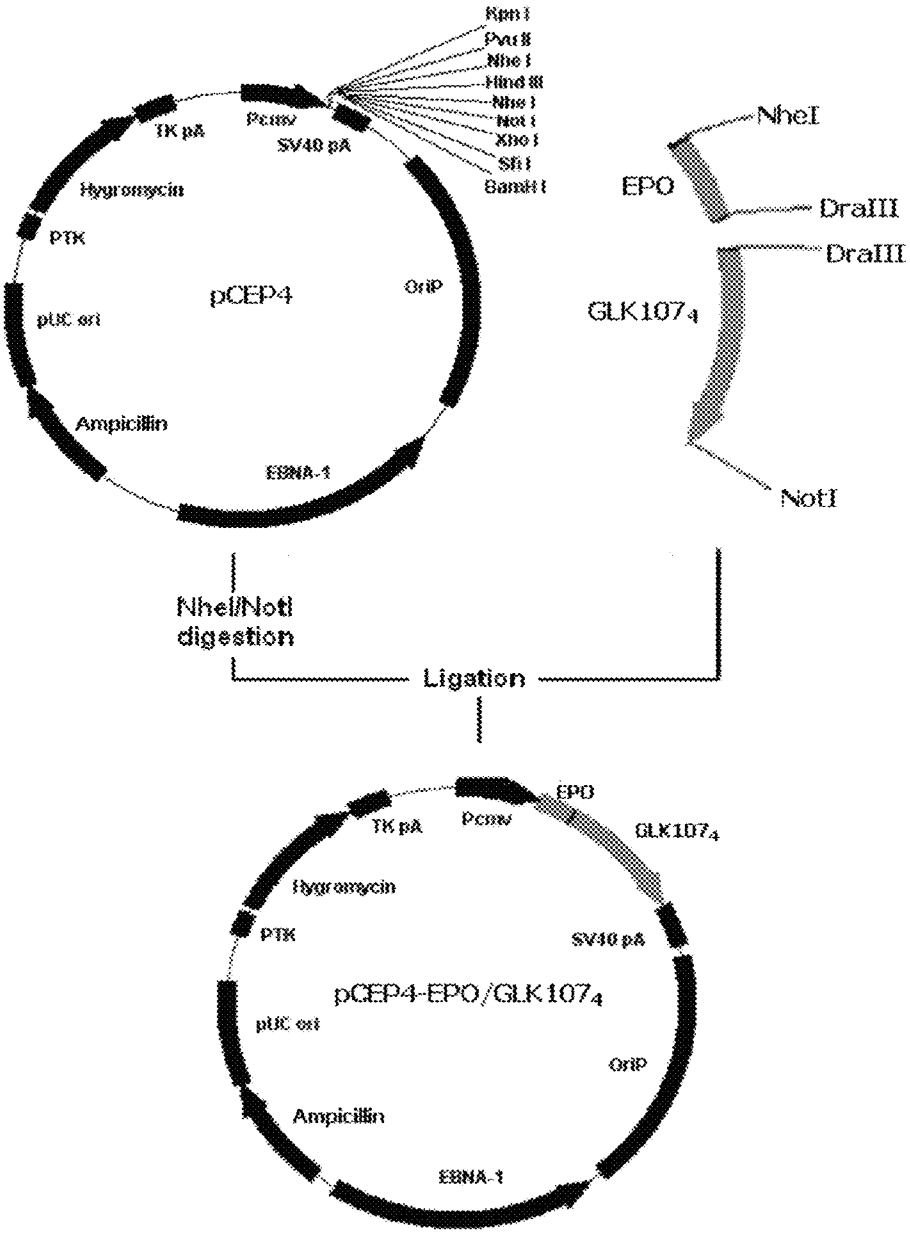
FIG. 20 shows the flow diagram showing the construction of the expression plasmid of pCEP4-EPO/GLK107$_4$.

The process of construction refers to FIG. 20. DNA sequence and mature amino acid sequence of the fusion protein rEPO/GLK107$_4$ refer to SEQ ID NO: 30 and SEQ ID NO: 31 respectively.

4. Construction of Cell Lines Expressing rEPO/GLK107$_4$ Recombinant Protein

The plasmid pCEP4-EPO/GLK107$_4$ was extracted by ultra-pure plasmid extraction kit (purchased from Marligen company). Activity of EPO was detected by ELISA after conventional transfection by liposome using Chinese hamster ovary cells (CHO) as the host cells. Positive clones were screened out with methotrexate (MTX) selective pressure.

One positive cell line was selected to culture with CD CHO serum-free medium (purchased from GIBCO company) gradually (Debeljak N et al., Anal Biochem., 359:216-223, 2006).

5.rEPO/GLK1074 Recombinant Protein Expression

Cell lines obtained in step 4 were recovered in serum-free medium, expanded sequential through 125 ml, 500 ml, 1000 ml rotating cell culture bottles, and then inoculated in B. Braun Biostart culture tank. The cells were supplemented with 10% 10-fold concentrated culture medium daily when the living cell density was above $1.5\times10^6$/ml, and cultured for 15 days. Sampling cell density was counted daily and amount of expression protein was detected with the Lowry method. After fermentation, the recombinant cell was harvested, 6000 r/min, centrifugation for 5 minutes and the supernatant was collected and analyzed by 8% SDS-PAGE electrophoresis.

6.Recombinant Protein rEPO/GLK$107_4$ Purification

Purification method was similar to Example 1.

Example 12

Role of rEPO/GLK$107_4$ Fusion Protein in Erythropoiesis in Normal Mice rEPO/GLK$107_4$ fusion protein was compared with standard rEPO (EPOGEN®, AMGEN Inc.) in erythropoiesis activity in mice. BALB/c mice (male, 6-8 weeks old, 18~20 g/only) from the Shanghai Institute of animal testing center were used in the experiments. Grouping, injection, and tail vein blood samples collecting were performed according to the following table. Hemoglobin (Hb) content was determined by colorimetric.

TABLE 6

The groups and dosage of different structure EPO pharmaceutical efficacy

| group | Animal number | dose (μg/kg) | route of adminis-tration | time for adminis-tration | blood sampling time(days) |
|---|---|---|---|---|---|
| rEPO/GLK$107_4$ | 3 | 50 | Sc | 1 times/week | 0, 4, 7, 11, 14, 18, 21, 25, 28, 32 |
| rEPO/GLK$107_4$ | 3 | 5 | Sc | 1 times/week | 0, 4, 7, 11, 14, 18, 21, 25, 28, 32 |
| rEPO/GLK$107_4$ | 3 | 0.5 | Sc | 1 times/week | 0, 4, 7, 11, 14, 18, 21, 25, 28, 32 |
| rEPO | 3 | 1.5 | Sc | 1 times/week | 0, 4, 7, 11, 14, 18, 21, 25, 28, 32 |
| rGLK$107_4$ | 3 | 1.5 | Sc | 1 times/week | 0, 4, 7, 11, 14, 18, 21, 25, 28, 32 |

Figure 21:
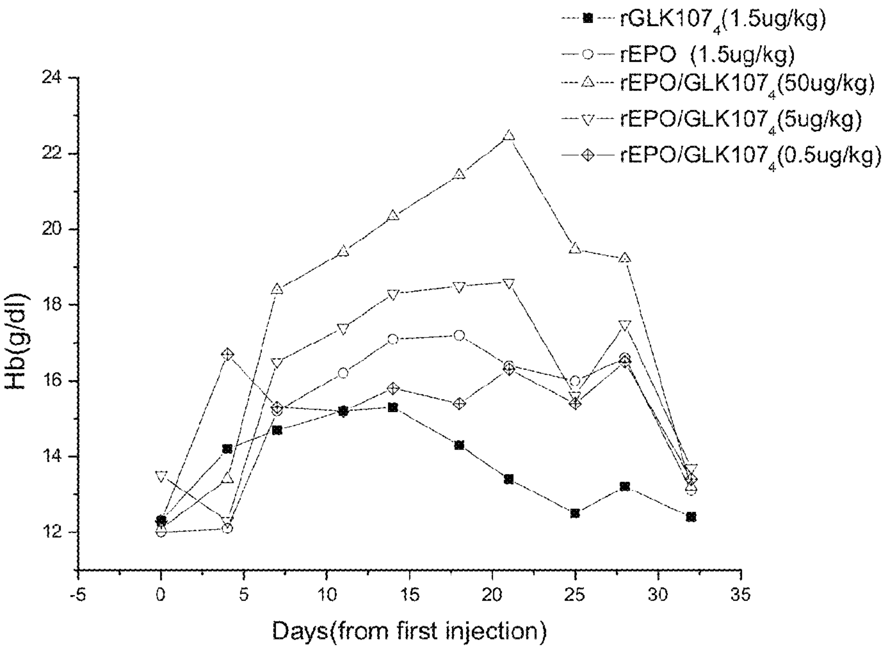
FIG. 21 shows the effectiveness evaluation result of pharmacodynamic studies of rEPO/GLK107$_4$ and rhEPO in normal BALB/c mice.

The results of weekly subcutaneous administration of rEPO/GLK$107_4$ in erythropoiesis were shown in FIG. 21. In different rEPO/GLK$107_4$ dose groups, with the dose increased, Hb levels increase accordingly. rEPO also possesses the activity of erythropoiesis, but the activity was significantly lower than rEPO/GLK$107_4$ in the similar moles. Therefore, compared to rEPO, rEPO/GLK$107_4$ not only extends the delivery period, but also augments the activity of erythropoiesis.

Example 13

Pharmaceutical Compositions

Preparation of injectable solution containing fusion proteins rGLK1164/G-CSF as follows: 200 ml rGLK1164/G-CSF fusion protein stock solution (15.5 mg/mL) containing 10 mmol/L phosphate buffer (pH 6.5) was taken, and 7.13 g of glycine was added, then 2.2 ml 0.5 mol/L phosphate buffer (pH 6.5) was added after glycine was completely dissolved. pH was adjusted to 6.5 with 10% NaOH, and finally the water for injection was added to 310 ml. After mixing, the preparation was sterile filtered with a 0.22 micron filter membranes and distributed to penicillin bottles. Final preparation composition: rGLK1164/G-CSF fusion protein concentration of 10 mg/mL, phosphate buffer concentration of 10 mmol/L, pH 6.5, glycine content of 2.3% (w/v).

TABLE 7

Sequence statement

| SEQ ID NO: | STATEMENT |
|---|---|
| 1 | Complementary DNA sequence that encodes GLK$116_1$ monomer(CDS: 1-372, of which 1-24 encoding α signal peptide, it's the same as followed) |
| 2 | Amino acid sequence of rGLK$116_1$ |
| 3 | Complementary DNA sequence(CDS: 1-1344) that encodes GLK$116_4$ |
| 4 | Complementary DNA sequence(CDS: 22-543) that encodes hG-CSF |
| 5 | Complementary DNA sequence(CDS: 1-1866) that encodes GLK$116_4$/G-CSF |
| 6 | Amino acid sequence of rGLK$116_4$/G-CSF |
| 7 | Complementary DNA sequence(CDS: 1-1284) that encodes GLK$_{420}$ |
| 8 | Amino acid sequence of rGLK$_{420}$ |
| 9 | Complementary DNA sequence(CDS: 1-1806) that encodes GLK$_{420}$/G-CSF |
| 10 | Amino acid sequence of rGLK$_{420}$/G-CSF |
| 11 | Complementary DNA sequence(CDS: 22-516) that encodes Interferon α2b |
| 12 | Complementary DNA sequence(CDS: 1-1839) that encodes GLK$116_4$/IFNα |
| 13 | Amino acid sequence of rGLK$116_4$/IFNα |
| 14 | Amino acid sequence of rGLK$116_2$/IFNα |
| 15 | Amino acid sequence of rGLK$116_2$P-/IFNα |
| 16 | Amino acid sequence of rGLK302S/IFNα |
| 17 | Amino acid sequence of rGLK$116_2$N-/IFNα |
| 18 | Complementary DNA sequence(CDS: 1-336) that encodesGLK$104_1$ monomer |
| 19 | Amino acid sequence of rGLK$104_1$ monomer |
| 20 | Complementary DNA sequence(CDS: 1-345) that encodes GLK$107_1$ monomer |
| 21 | Amino acid sequence of rGLK$107_1$ monomer |
| 22 | Complementary DNA sequence(CDS: 1-141) that encodes Exendin-4 |
| 23 | Complementary DNA sequence(CDS: 1-1938) that encodes Exendin-4/GLK$104_6$ |
| 24 | Amino acid sequence of rExendin-4/GLK$104_6$ |
| 25 | Complementary DNA sequence(CDS: 1-1992) that encodes Exendin-4/GLK$107_6$ |
| 26 | Amino acid sequence of Exendin-4/GLK$107_6$ |
| 27 | Complementary DNA sequence(CDS: 13-591) that encodes EPO |
| 28 | Forward primer of GLK$107_4$ |
| 29 | Reverse primer of GLK$107_4$ |
| 30 | Complementary DNA sequence(CDS: 13-1830) that encodes EPO/GLK$107_4$ |
| 31 | Amino acid sequence of rEPO/GLK$107_4$ |

All the literatures mentioned in the present invention were cited in this application as references, just as each one is a separate reference to literature. Besides, after reading the contents described above of the present invention, it should be understood that all the changes, modifications or other equivalent forms of the invention made by technicians in this area are ranged in the claims attached to the application.

What is claimed is:

1. A method for extending half-life of bioactive peptides or proteins in vivo, comprising steps of:

providing a gelatin-like protein as fusion carrier; and fusing the gelatin-like protein with the bioactive peptides or proteins to obtain a recombinant fusion protein;

wherein, the gelatin-like protein has a structure characterized as follows:

(Gly-X-Y) n;

wherein, the Gly is glycine residues; the X and Y are selected from a group of 20 natural amino acid residues except cysteine respectively, n=20-300; wherein the gelatin-like protein is defined by:

(a) a sum of Asn, Asp, Gln, Glu, Lys, Pro, Ser, Hyp and Arg residues is from 40% to ⅔ (66.7%) of the total amino acid sequence of the gelatin-like protein;

(b) total number of Pro and Hyp residues is larger than 60% of the value of n;

(c) total number of Gly residues is less than 1.15-fold value of n;

(d) according to a ProtParam computational formula, a value of the hydrophilic index GRAVY is less than −1.5;

(e) the gelatin-like protein as described excludes natural gelatin; wherein the gelatin-like protein comprises the amino acid sequence as set for the in SEQ ID NO:2 or the amino acid sequence encoded by an isolated polynucleotide molecule that has a nucleotide sequence as set forth in SEQ ID NO:3.

2. The method for extending half-life of bioactive peptides or proteins in vivo as described in claim 1, wherein the gelatin-like protein is further defined by:

(f) an isoelectric point is between pH 3 and 7;

(g) according to a Kolaskar-Tongaonkar algorithm, an average antigenic propensity is less than 0.98.

3. The method for extending half-life of bioactive peptides or proteins in vivo as described in claim 1, wherein a molecular weight of the Gelatin-like units is 10-100 kDa.

4. A recombinant fusion protein, which is composed of a biologically active protein or peptide fused with a gelatin-like protein, wherein the gelatin-like protein has a structure characterized as follows:

(Gly-X-Y) n;

wherein, the Gly is glycine residues; the X and Y are selected from a group of 20 natural amino acid residues except cysteine respectively, n=20-300; wherein the gelatin-like protein is defined by:

(a) a sum of Asn, Asp, Gln, Glu, Lys, Pro, Ser, Hyp and Arg residues is from 40% to ⅔ (66.7%) of the total amino acid sequence of the gelatin-like protein;

(b) total number of Pro and Hyp residues is larger than 60% of the value of n;

(c) total number of Gly residues is less than 1.15-fold value of n;

(d) according to a ProtParam computational formula, a value of the hydrophilic index GRAVY is less than −1.5;

(e) gelatin-like protein as described excludes natural gelatin;

wherein the gelatin-like protein comprises the amino acid sequence as set for the in SEQ ID NO:2 or the amino acid sequence encoded by an isolated polynucleotide molecule that has a nucleotide sequence as set forth in SEQ ID NO:3.

5. The recombinant fusion proteins as described in claim 4, wherein the recombinant fusion proteins has an enhanced pharmacokinetic property which means an increase in terminal half-life in vivo of at least two-fold longer compared to a corresponding biologically active protein or peptide not fused with the gelatin-like protein.

6. The recombinant fusion proteins as described in claim 4, wherein the fusion protein characterized in that: the gelatin-like protein as described are fused in N terminal, C terminal or both N and C terminal.

7. The recombinant fusion proteins as described in claim 4, which is monovalent or multivalent unit of formula (I), {GLK} p-R-{GLK} q (I)

Wherein, gelatin-like protein refers to the gelatin-like protein as described in claim 1;

p and q is independently 0 or 1, and p and q should not both be 0;

R represents biologically active protein except gelatin or gelatin-like protein as described above ; and "-" represents the peptide bond.

8. The recombinant fusion proteins as described in claim 7, wherein the recombinant fusion protein is multivalent unit of formula (I) wherein each R and gelatin-like protein may either be the same or be different.

9. An isolated polynucleotide molecule encoding recombinant fusion proteins of claim 4.

10. An expression vector containing the isolated polynucleotide molecule of claim 9.

11. A recombinant host cell comprising the expression vector of claim 10.

12. A method for preparing a recombinant fusion protein comprising following steps:

(a) cultivating the host cells of claim 11 and to express the recombinant fusion protein; and (b) purifying the recombinant fusion protein.

13. A recombinant host cell comprising a chromosome that is integrated with the polynucleotide of claim 9.

14. The method for extending half-life of bioactive peptides or proteins in vivo as described in claim 1, wherein the ratio of the apparent molecular weight (gel filtration analysis) of the recombinant fusion protein as described to the theoretical molecular weight is no less than 1.25.

15. The method for extending half-life of bioactive peptides or proteins in vivo as described in claim 1, wherein the molecular weight of the bioactive peptides or proteins as described is between 0.5 to 70 Kda.

16. The method for extending half-life of bioactive peptides or proteins in vivo as described in claim 1, wherein the gelatin-like protein as described are located beside either or both, or between an amino terminal and a C-terminus of the fusion proteins.

17. The method for extending half-life of bioactive peptides or proteins in vivo as described in claim 1, wherein the recombinant fusion protein as described is monomer or multi-polymer.

18. The method for extending half-life of bioactive peptides or proteins in vivo as described in claim 17, wherein the recombinant fusion protein as described is monomer or multi-polymer of formula (I), {GLK}p-R-{GLK} q (I)

wherein,

GLK refers to the gelatin-like protein as described;

p and q is independently 0 or 1, and p and q should not both be 0;

R represents bioactive peptides or proteins; and

"-" represents the peptide bond.

19. The method for extending half-life of bioactive peptides or proteins in vivo as described in claim 1, wherein the molecular weight of the recombinant fusion proteins as described is between 20 to 500 Kda.

20. The method for extending half-life of bioactive peptides or proteins in vivo as described in claim 18, wherein the recombinant fusion protein as described in formula (I) are multi-polymers, wherein each R may either be the same or be different, and each GLK may either be the same or be different.

21. A gelatin-like protein that can be used to extend half-life of peptides or proteins in vivo, having a structure of (Gly-X-Y) n;

wherein, the Gly is glycine residues; the X and Y are selected from a group of 20 natural amino acid residues except cysteine respectively, n=20-300; wherein the gelatin-like protein is defined by:

(a) a sum of Asn, Asp, Gln, Glu, Lys, Pro, Ser, Hyp and Arg residues is from 40% to ⅔ (66.7%) of the total amino acid sequence of the gelatin-like protein;

(b) total number of Pro and Hyp residues is larger than 60% of the value of n;

(c) total number of Gly residues is less than 1.15-fold value of n;

(d) according to a ProtParam computational formula, a value of the hydrophilic index GRAVY is less than −1.5;

(e) the gelatin-like protein as described excludes natural gelatin;

wherein the gelatin-like protein comprises the amino acid sequence as set for the in SEQ ID NO:2 or the amino acid sequence encoded by an isolated polynucleotide molecule that has a nucleotide sequence as set forth in SEQ ID NO:3.

* * * * *